US011203744B2

(12) United States Patent
Lynch et al.

(10) Patent No.: US 11,203,744 B2

(45) Date of Patent: Dec. 21, 2021

(54) COMPOSITIONS AND METHODS FOR THE PRODUCTION OF PYRUVIC ACID AND RELATED PRODUCTS USING DYNAMIC METABOLIC CONTROL

(71) Applicant: DUKE UNIVERSITY, Durham, NC (US)

(72) Inventors: Michael David Lynch, Durham, NC (US); Zhixia Ye, Raleigh, NC (US)

(73) Assignee: DUKE UNIVERSITY, Durham, NC (US)

(*) Notice: Subject to any disclaimer, the term of this patent is extended or adjusted under 35 U.S.C. 154(b) by 0 days.

(21) Appl. No.: 16/448,292

(22) Filed: Jun. 21, 2019

(65) Prior Publication Data

US 2019/0390232 A1 Dec. 26, 2019

Related U.S. Application Data

(60) Provisional application No. 62/687,874, filed on Jun. 21, 2018.

(51) Int. Cl.

| | |
|---|---|
| ***C12N 9/12*** | (2006.01) |
| ***C12N 9/04*** | (2006.01) |
| ***C12P 7/00*** | (2006.01) |
| ***C12N 1/20*** | (2006.01) |
| ***C12P 7/40*** | (2006.01) |

(Continued)

(52) U.S. Cl.

CPC ......... *C12N 9/1205* (2013.01); *C12N 9/0006* (2013.01); *C12N 9/0036* (2013.01); *C12N 9/0051* (2013.01); *C12N 9/1025* (2013.01); *C12P 7/40* (2013.01); *C12Y 101/01049* (2013.01); *C12Y 106/03001* (2013.01); *C12Y 108/01004* (2013.01); *C12Y 203/03001* (2013.01); *C12Y 207/0104* (2013.01)

(58) Field of Classification Search

CPC ........ C12N 9/1205; C12N 9/0006; C12P 7/40

See application file for complete search history.

(56) References Cited

U.S. PATENT DOCUMENTS

| | | | |
|---|---|---|---|
| 8,916,358 | B2 | 12/2014 | Swartz |
| 10,036,001 | B2 | 7/2018 | Swartz |

(Continued)

FOREIGN PATENT DOCUMENTS

| | | | |
|---|---|---|---|
| EP | 2562249 | A1 | 2/2013 |
| EP | 2842542 | A1 | 3/2015 |

(Continued)

OTHER PUBLICATIONS

Lynch. Into new territory: improved microbial synthesis through engineering of the essential metabolic network. Curr Opin Biotechnol. Apr. 2016;38:106-11.*

(Continued)

*Primary Examiner* — Yong D Pak

(74) *Attorney, Agent, or Firm* — Benesch, Friedlander, Coplan & Aronoff LLP

(57) ABSTRACT

The present disclosure is related to genetically engineered microbial strains and related bioprocesses for the production of pyruvate and related products. Specifically, the use of dynamically controlled synthetic metabolic valves to reduce the activity of enzymes known to contribute to pyruvate synthesis, leads to increased pyruvate production in a two-stage process rather than a decrease in production.

10 Claims, 2 Drawing Sheets

Specification includes a Sequence Listing.

(51) Int. Cl.
*C12N 9/10* (2006.01)
*C12N 9/02* (2006.01)

(56) References Cited

U.S. PATENT DOCUMENTS

| | | | | |
|---|---|---|---|---|
| 10,662,426 | B2 * | 5/2020 | Lynch | C12N 15/63 |
| 2010/0297736 | A1 | 11/2010 | Duhring et al. | |
| 2011/0125118 | A1 | 5/2011 | Lynch | |
| 2011/0244575 | A1 | 10/2011 | Lipscomb | |
| 2012/0052547 | A1 | 3/2012 | Swartz | |
| 2012/0107892 | A1 | 5/2012 | Agbogbo et al. | |
| 2012/0214170 | A1 | 8/2012 | Moore | |
| 2015/0072399 | A1 | 3/2015 | Lynch et al. | |
| 2017/0121707 | A1 * | 5/2017 | Lynch | C12N 15/70 |
| 2020/0056211 | A1 * | 2/2020 | Lynch | C12N 9/0051 |
| 2020/0149075 | A1 * | 5/2020 | Lynch | C12N 9/0036 |
| 2020/0248211 | A1 * | 8/2020 | Lynch | C12P 13/06 |
| 2020/0248212 | A1 * | 8/2020 | Lynch | C07K 14/245 |
| 2020/0299687 | A1 * | 9/2020 | Lynch | C12P 7/18 |
| 2020/0325501 | A1 * | 10/2020 | Lynch | C12N 15/746 |
| 2020/0347388 | A1 * | 11/2020 | Lynch | C12P 13/06 |

FOREIGN PATENT DOCUMENTS

| | | | |
|---|---|---|---|
| WO | 2001068883 | A1 | 9/2001 |
| WO | 2003054140 | A9 | 2/2004 |
| WO | 2008141174 | A2 | 11/2008 |
| WO | 2010141468 | A1 | 12/2010 |
| WO | 2012129450 | A1 | 9/2012 |
| WO | 2013176772 | A1 | 11/2013 |
| WO | 2014160025 | A2 | 10/2014 |
| WO | 2015191638 | A1 | 12/2015 |
| WO | 2018156646 | A1 | 8/2018 |

OTHER PUBLICATIONS

Shimizu. Global metabolic response of *Escherichia coli* to gnd or zwf gene-knockout, based on 13C-labeling experiments and the measurement of enzyme activities. Appl Microbiol Biotechnol (2004) 64: 91-98.*

Lynch (Standardized two-stage bioprocess development using synthetic metabolic valves and dynamic metabolic control, Abstract of Papers: ACS National Meeting & Exposition; 249th National Meeting and Exposition of the American-Chemical-Society (ACS), vol. 249, p. BIOT418. Mar. 22-26, 2015.*

Fang. Codon-Optimized NADH Oxidase Gene Expression and Gene Fusion with Glycerol Dehydrogenase for Bienzyme System with Cofactor Regeneration. PLOS ONE. Jun. 26, 2015.*

Ponce. Effect of Growth Rate Reduction and Genetic Modifications on Acetate Accumulation and Biomass Yields in *Escherichia coli*. Journal of Bioscikince and Bioengineering. vol. 81, No. 6, 775-780. 1999.*

Siddiquee. Effect of a pyruvate kinase (pykF-gene) knockout mutation on the control of gene expression and metabolic fluxes in *Escherichia coli*. FEMS Microbiology Letters 235 (2004) 25-33.*

International Search Report and Written Opinion dated Apr. 27, 2016 from related International Application No. PCT/US2015/035306.

Fang, Shi-Ming et al., "A Practical Strategy to Discover New Antitumor Compounds by Activating Silent Metabolite Production in Fungi by Diethyl Sulphate Mutagenesis," Marine Drugs, vol. 12, pp. 1788-1814, 2014.

International Preliminary Report on Patentability dated Dec. 15, 2016 from related International App. No. PCT/US2015/035306.

UK Combined Examination and Search Report dated Dec. 8, 2016, from related UK Application No. GB1511937.3.

Torella, et al., Tailored fatty acid synthesis via dynamic control of fatty acid elongation. Proc. Natl. Acad. Sci. USA. Jul. 9, 2013; 110(28): 11290-5. doi: 10.1073/pnas.1307129110. Epub 2013.

Office Action issued in European patent application No. 15845669.9, dated Dec. 3, 2018, 6 pages.

Extended European search report issued in patent application No. 15845669.9, dated Jan. 3, 2018, 10 pages.

Yuki Soma et al.: "Matabolic flux redirection from a central metabolic pathway toward a synthetic pathway using a metabolic toggle switch", Metabolic Engineering, vol. 23, May 1, 2014, pp. 175-184.

Kathleen E. McGinness et al.: "Engineering Controllable Protein Degradation", Molecular Cell., vol. 22, No. 5, Jun. 1, 2006, pp. 701-707.

Levchenko Igor et al: "A specificity-enhancing factor for the ClpXP degradation machine", Science, vol. 289, No. 5488, Sep. 29, 2000, pp. 2354-2356.

UK Examination Report dated Apr. 1, 2019 from related UK application No. GB1511937.3.

English Translation of Mar. 12, 2019 Office Action related to Japanese application JP2016-572578.

Kim et al., "A genetic strategy to identify targets for the development of drugs that prevent bacterial persistance", Proc. Natl. Acad. Sci. USA (2013); vol. 110, pp. 19095-19100.

Qi et al. "Repurposing CRISPR as an RNA-guided platform for sequence-specific control of gene expression," Cell (2013); vol. 152, pp. 1173-1183.

Lynch et al., "Standardized two-stage bioprocess development using synthetic metabolic valves and dynamic metabolic control", Abstracts of Papers; ACS National Meeting & Exposition; Mar. 22-26, 2015, 249th National Meeting and Exposition of he American-Chemical-Society {ACS), vol. 249, p. BIOT418.

Brockman et al., "Dynamic knockdown of *E. coli* central metabolism for redirecting fluxes of primary metabolites", Metabolic Engineering, Mar. 2015, vol. 28, pp. 104-113.

B. J. Reed et al., "Dynamic two-stage metabolic control in S. cerevisiae for rapid strain engineering", Department of Biomedical Engineering, Duke University, American Chemical Society National Meeting, Mar. 14, 2016.

* cited by examiner

```
SEQUENCE LISTING

<160> NUMBER OF SEQ ID NOS: 103

<210> SEQ ID NO 1
<211> LENGTH: 76
<212> TYPE: DNA
<213> ORGANISM: Artificial Sequence
<220> FEATURE:
<223> OTHER INFORMATION: Oligonucleotide:  ilcR_tetA_F

<400> SEQUENCE: 1

taacaataaa aatgaaaatg atttccacga tacagaaaaa agagactgtc atcctaattt     60

ttgttgacac tctatc                                                     76


<210> SEQ ID NO 2
<211> LENGTH: 75
<212> TYPE: DNA
<213> ORGANISM: Artificial Sequence
<220> FEATURE:
<223> OTHER INFORMATION: Oligonucleotide:  ilcR_sacB_R

<400> SEQUENCE: 2

tgccactcag gtatgatggg cagaatattg cctctgcccg ccagaaaaag atcaaaggga     60

aaactgtcca tatgc                                                      75


<210> SEQ ID NO 3
<211> LENGTH: 19
<212> TYPE: DNA
<213> ORGANISM: Artificial Sequence
<220> FEATURE:
<223> OTHER INFORMATION: Oligonucleotide: iclR_500up

<400> SEQUENCE: 3

ccgacaggga ttccatctg                                                  19


<210> SEQ ID NO 4
<211> LENGTH: 26
<212> TYPE: DNA
<213> ORGANISM: Artificial Sequence
<220> FEATURE:
<223> OTHER INFORMATION: Oligonucleotide:  iclR_500dn

<400> SEQUENCE: 4

tatgacgacc attttgtcta cagttc                                          26


<210> SEQ ID NO 5
<211> LENGTH: 75
<212> TYPE: DNA
<213> ORGANISM: Artificial Sequence
<220> FEATURE:
<223> OTHER INFORMATION: Oligonucleotide: arcA_tetA_F

<400> SEQUENCE: 5

ggacttttgt acttcctgtt tcgatttagt tggcaattta ggtagcaaac tcctaatttt     60

tgttgacact ctatc                                                      75
```

<210> SEQ ID NO 6
<211> LENGTH: 75
<212> TYPE: DNA
<213> ORGANISM: Artificial Sequence
<220> FEATURE:
<223> OTHER INFORMATION: Oligonucleotide: arcA_sacB_R

<400> SEQUENCE: 6
ataaaaacgg cgctaaaaag cgccgttttt tttgacggtg gtaaagccga atcaaaggga 60
aaactgtcca tatgc 75

<210> SEQ ID NO 7
<211> LENGTH: 22
<212> TYPE: DNA
<213> ORGANISM: Artificial Sequence
<220> FEATURE:
<223> OTHER INFORMATION: Oligonucleotide: arcA_500up

<400> SEQUENCE: 7
cctgactgta ctaacggttg ag 22

<210> SEQ ID NO 8
<211> LENGTH: 27
<212> TYPE: DNA
<213> ORGANISM: Artificial Sequence
<220> FEATURE:
<223> OTHER INFORMATION: Oligonucleotide: arcA_500dn

<400> SEQUENCE: 8
tgacttttat ggcgttcttt gtttttg 27

<210> SEQ ID NO 9
<211> LENGTH: 22
<212> TYPE: DNA
<213> ORGANISM: Artificial Sequence
<220> FEATURE:
<223> OTHER INFORMATION: Oligonucleotide: sspB_kan_F

<400> SEQUENCE: 9
ctggtacacg ctgatgaaca cc 22

<210> SEQ ID NO 10
<211> LENGTH: 21
<212> TYPE: DNA
<213> ORGANISM: Artificial Sequence
<220> FEATURE:
<223> OTHER INFORMATION: Oligonucleotide: sspB_kan_R

<400> SEQUENCE: 10
ctggtcattg ccatttgtgc c 21

<210> SEQ ID NO 11
<211> LENGTH: 20
<212> TYPE: DNA
<213> ORGANISM: Artificial Sequence
<220> FEATURE:
<223> OTHER INFORMATION: Oligonucleotide: sspB_conf_F

<400> SEQUENCE: 11
gaatcagagc gttccgaccc 20

<210> SEQ ID NO 12
<211> LENGTH: 20
<212> TYPE: DNA

<213> ORGANISM: Artificial Sequence
<220> FEATURE:
<223> OTHER INFORMATION: Oligonucleotide:sspB_conf_R

<400> SEQUENCE: 12
gtacgcagtt tgccaacgtg 20

<210> SEQ ID NO 13
<211> LENGTH: 75
<212> TYPE: DNA
<213> ORGANISM: Artificial Sequence
<220> FEATURE:
<223> OTHER INFORMATION: Oligonucleotide:cas3_tetA_F

<400> SEQUENCE: 13
aatagcccgc tgatatcatc gataatacta aaaaaacagg gaggctatta tcctaatttt 60
tgttgacact ctatc 75

<210> SEQ ID NO 14
<211> LENGTH: 75
<212> TYPE: DNA
<213> ORGANISM: Artificial Sequence
<220> FEATURE:
<223> OTHER INFORMATION: Oligonucleotide: cas3_sacB_R

<400> SEQUENCE: 14
tacagggatc cagttatcaa taagcaaatt catttgttct ccttcatatg atcaaaggga 60
aaactgtcca tatgc 75

<210> SEQ ID NO 15
<211> LENGTH: 27
<212> TYPE: DNA
<213> ORGANISM: Artificial Sequence
<220> FEATURE:
<223> OTHER INFORMATION: Oligonucleotide: cas3_conf_F

<400> SEQUENCE: 15
caagacatgt gtatatcact gtaattc 27

<210> SEQ ID NO 16
<211> LENGTH: 23
<212> TYPE: DNA
<213> ORGANISM: Artificial Sequence
<220> FEATURE:
<223> OTHER INFORMATION: Oligonucleotide: cas3_500dn

<400> SEQUENCE: 16
gcgattgcag atttatgatt tgg 23

<210> SEQ ID NO 17
<211> LENGTH: 20
<212> TYPE: DNA
<213> ORGANISM: Artificial Sequence
<220> FEATURE:
<223> OTHER INFORMATION: Oligonucleotide: gltA_conf_F

<400> SEQUENCE: 17
tatcatcctg aaagcgatgg 20

<210> SEQ ID NO 18
<211> LENGTH: 18
<212> TYPE: DNA
<213> ORGANISM: Artificial Sequence
<220> FEATURE:
<223> OTHER INFORMATION: Oligonucleotide: lpd_conf_F

<400> SEQUENCE: 18
atctcaccgt gtgatcgg 18

<210> SEQ ID NO 19
<211> LENGTH: 24
<212> TYPE: DNA
<213> ORGANISM: Artificial Sequence
<220> FEATURE:
<223> OTHER INFORMATION: Oligonucleotide: udhA_conf_F

<400> SEQUENCE: 19
caaaagagat tctgggtatt cact 24

<210> SEQ ID NO 20
<211> LENGTH: 17
<212> TYPE: DNA
<213> ORGANISM: Artificial Sequence
<220> FEATURE:
<223> OTHER INFORMATION: Oligonucleotide: zwf_conf_F

<400> SEQUENCE: 20
ctgctggaaa ccatgcg 17

<210> SEQ ID NO 21
<211> LENGTH: 25
<212> TYPE: DNA
<213> ORGANISM: Artificial Sequence
<220> FEATURE:
<223> OTHER INFORMATION: Oligonucleotide: zwf_500dn

<400> SEQUENCE: 21
agagcatgtc gttataggag gtgat 25

<210> SEQ ID NO 22
<211> LENGTH: 22
<212> TYPE: DNA
<213> ORGANISM: Artificial Sequence
<220> FEATURE:
<223> OTHER INFORMATION: Oligonucleotide: ampR_intR

<400> SEQUENCE: 22
agtactcaac caagtcattc tg 22

<210> SEQ ID NO 23
<211> LENGTH: 21
<212> TYPE: DNA
<213> ORGANISM: Artificial Sequence
<220> FEATURE:
<223> OTHER INFORMATION: Oligonucleotide: bsdR_intR

<400> SEQUENCE: 23
gagcatggtg atcttctcag t 21

<210> SEQ ID NO 24
<211> LENGTH: 22
<212> TYPE: DNA
<213> ORGANISM: Artificial Sequence
<220> FEATURE:
<223> OTHER INFORMATION: Oligonucleotide: gentR_intR

<400> SEQUENCE: 24
gcgatgaatg tcttactacg ga 22

<210> SEQ ID NO 25

<211> LENGTH: 19
<212> TYPE: DNA
<213> ORGANISM: Artificial Sequence
<220> FEATURE:
<223> OTHER INFORMATION: Oligonucleotide: purR_intR

<400> SEQUENCE: 25
gtcgctgggt aatctgcaa 19

<210> SEQ ID NO 26
<211> LENGTH: 23
<212> TYPE: DNA
<213> ORGANISM: Artificial Sequence
<220> FEATURE:
<223> OTHER INFORMATION: Oligonucleotide: tetA_intR

<400> SEQUENCE: 26
atcaacgcat atagcgctag cag 23

<210> SEQ ID NO 27
<211> LENGTH: 18
<212> TYPE: DNA
<213> ORGANISM: Artificial Sequence
<220> FEATURE:
<223> OTHER INFORMATION: Oligonucleotide: zeoR_intR

<400> SEQUENCE: 27
actgaagccc agacgatc 18

<210> SEQ ID NO 28
<211> LENGTH: 23
<212> TYPE: DNA
<213> ORGANISM: Artificial Sequence
<220> FEATURE:
<223> OTHER INFORMATION: Oligonucleotide: tetR_intR

<400> SEQUENCE: 28
atcaacgcat atagcgctag cag 23

<210> SEQ ID NO 29
<211> LENGTH: 18
<212> TYPE: DNA
<213> ORGANISM: Artificial Sequence
<220> FEATURE:
<223> OTHER INFORMATION: Oligonucleotide: specR_intR

<400> SEQUENCE: 29
cactgtgtgg cttcaggc 18

<210> SEQ ID NO 30
<211> LENGTH: 22
<212> TYPE: DNA
<213> ORGANISM: Artificial Sequence
<220> FEATURE:
<223> OTHER INFORMATION: Oligonucleotide: ampR_intR

<400> SEQUENCE: 30
agtactcaac caagtcattc tg 22

<210> SEQ ID NO 31
<211> LENGTH: 19
<212> TYPE: DNA
<213> ORGANISM: Artificial Sequence
<220> FEATURE:
<223> OTHER INFORMATION: Oligonucleotide: purR_intR

<400> SEQUENCE: 31
gtcgctgggt aatctgcaa 19

<210> SEQ ID NO 32
<211> LENGTH: 18
<212> TYPE: DNA
<213> ORGANISM: Artificial Sequence
<220> FEATURE:
<223> OTHER INFORMATION: Oligonucleotide: PykA-FOR1

<400> SEQUENCE: 32
cctgactgct ctctatcg 18

<210> SEQ ID NO 33
<211> LENGTH: 19
<212> TYPE: DNA
<213> ORGANISM: Artificial Sequence
<220> FEATURE:
<223> OTHER INFORMATION: Oligonucleotide: PykA-FOR2

<400> SEQUENCE: 33
cgaagcggtt aatctgctg 19

<210> SEQ ID NO 34
<211> LENGTH: 20
<212> TYPE: DNA
<213> ORGANISM: Artificial Sequence
<220> FEATURE:
<223> OTHER INFORMATION: Oligonucleotide: PykF-FOR1

<400> SEQUENCE: 34
cggctcatca gttggtactg 20

<210> SEQ ID NO 35
<211> LENGTH: 20
<212> TYPE: DNA
<213> ORGANISM: Artificial Sequence
<220> FEATURE:
<223> OTHER INFORMATION: Oligonucleotide: PykF-FOR2

<400> SEQUENCE: 35
gggtaaagaa ctggctctgc 20

<210> SEQ ID NO 36
<211> LENGTH: 3527
<212> TYPE: DNA
<213> ORGANISM: Artificial Sequence
<220> FEATURE:
<223> OTHER INFORMATION: tetA-sacB Cassette

<400> SEQUENCE: 36
tcctaatttt tgttgacact ctatcattga tagagttatt ttaccactcc ctatcagtga 60
tagagaaaag tgaaatgaat agttcgacaa agatcgcatt ggtaattacg ttactcgatg 120
ccatggggat tggccttatc atgccagtct tgccaacgtt attacgtgaa tttattgctt 180
cggaagatat cgctaaccac tttggcgtat tgcttgcact ttatgcgtta atgcaggtta 240
tctttgctcc ttggcttgga aaaatgtctg accgatttgg tcggcgccca gtgctgttgt 300
tgtcattaat aggcgcatcg ctggattact tattgctggc tttttcaagt gcgctttgga 360
tgctgtattt aggccgtttg ctttcaggga tcacaggagc tactggggct gtcgcggcat 420
cggtcattgc cgataccacc tcagcttctc aacgcgtgaa gtggttcggt tggttagggg 480
caagttttgg gcttggttta atagcggggc ctattattgg tggttttgca ggagagattt 540

```
caccgcatag tccctttttt atcgctgcgt tgctaaatat tgtcactttc cttgtggtta    600

tgttttggtt ccgtgaaacc aaaaatacac gtgataatac agataccgaa gtaggggttg    660

agacgcaatc gaattcggta tacatcactt tatttaaaac gatgcccatt ttgttgatta    720

tttatttttc agcgcaattg ataggccaaa ttcccgcaac ggtgtgggtg ctatttaccg    780

aaaatcgttt tggatggaat agcatgatgg ttggcttttc attagcgggt cttggtcttt    840

tacactcagt attccaagcc tttgtggcag gaagaatagc cactaaatgg ggcgaaaaaa    900

cggcagtact gctcggattt attgcagata gtagtgcatt tgccttttta gcgtttatat    960

ctgaaggttg gttagttttc cctgttttaa ttttattggc tggtggtggg atcgctttac   1020

ctgcattaca gggagtgatg tctatccaaa caaagagtca tcagcaaggt gctttacagg   1080

gattattggt gagccttacc aatgcaaccg gtgttattgg cccattactg tttgctgtta   1140

tttataatca ttcactacca atttgggatg gctggatttg gattattggt ttagcgtttt   1200

actgtattat tatcctgcta tcgatgacct tcatgttaac ccctcaagct caggggagta   1260

aacaggagac aagtgcttag ttatttcgtc accaaatgat gttattccgc gaaatataat   1320

gaccctcttg ataacccaag agcatcacat atacctgccg ttcactatta tttagtgaaa   1380

tgagatatta tgatattttc tgaattgtga ttaaaaaggc aactttatgc ccatgcaaca   1440

gaaactataa aaaatacaga gaatgaaaag aaacagatag atttttttagt tctttaggcc   1500

cgtagtctgc aaatcctttt atgattttct atcaaacaaa agaggaaaat agaccagttg   1560

caatccaaac gagagtctaa tagaatgagg tcgaaaagta aatcgcgcgg gtttgttact   1620

gataaagcag gcaagaccta aaatgtgtaa agggcaaagt gtatactttg gcgtcacccc   1680

ttacatattt taggtctttt tttattgtgc gtaactaact tgccatcttc aaacaggagg   1740

gctggaagaa gcagaccgct aacacagtac ataaaaaagg agacatgaac gatgaacatc   1800

aaaaagtttg caaaacaagc aacagtatta acctttacta ccgcactgct ggcaggaggc   1860

gcaactcaag cgtttgcgaa agaaacgaac caaaagccat ataaggaaac atacggcatt   1920

tcccatatta cacgccatga tatgctgcaa atccctgaac agcaaaaaaa tgaaaaatat   1980

caagttcctg agttcgattc gtccacaatt aaaaatatct cttctgcaaa aggcctggac   2040

gtttgggaca gctggccatt acaaaacgct gacggcactg tcgcaaacta tcacggctac   2100

cacatcgtct ttgcattagc cggagatcct aaaaatgcgg atgacacatc gatttacatg   2160

ttctatcaaa aagtcggcga aacttctatt gacagctgga aaaacgctgg ccgcgtcttt   2220

aaagacagcg acaaattcga tgcaaatgat tctatcctaa aagaccaaac acaagaatgg   2280

tcaggttcag ccacatttac atctgacgga aaaatccgtt tattctacac tgatttctcc   2340

ggtaaacatt acggcaaaca aacactgaca actgcacaag ttaacgtatc agcatcagac   2400

agctctttga acatcaacgg tgtagaggat tataaatcaa tctttgacgg tgacggaaaa   2460

acgtatcaaa atgtacagca gttcatcgat gaaggcaact acagctcagg cgacaaccat   2520

acgctgagag atcctcacta cgtagaagat aaaggccaca aatacttagt atttgaagca   2580

aacactggaa ctgaagatgg ctaccaaggc gaagaatctt tatttaacaa agcatactat   2640

ggcaaaagca catcattctt ccgtcaagaa agtcaaaaac ttctgcaaag cgataaaaaa   2700

cgcacggctg agttagcaaa cggcgctctc ggtatgattg agctaaacga tgattacaca   2760

ctgaaaaaag tgatgaaacc gctgattgca tctaacacag taacagatga aattgaacgc   2820

gcgaacgtct ttaaaatgaa cggcaaatgg tacctgttca ctgactcccg cggatcaaaa   2880

atgacgattg acggcattac gtctaacgat atttacatgc ttggttatgt ttctaattct   2940
```

```
ttaactggcc catacaagcc gctgaacaaa actggccttg tgttaaaaat ggatcttgat   3000

cctaacgatg taacctttac ttactcacac ttcgctgtac ctcaagcgaa aggaaacaat   3060

gtcgtgatta caagctatat gacaaacaga ggattctacg cagacaaaca atcaacgttt   3120

gcgccaagct tcctgctgaa catcaaaggc aagaaaacat ctgttgtcaa agacagcatc   3180

cttgaacaag gacaattaac agttaacaaa taaaaacgca aaagaaaatg ccgatattga   3240

ctaccggaag cagtgtgacc gtgtgcttct caaatgcctg attcaggctg tctatgtgtg   3300

actgttgagc tgtaacaagt tgtctcaggt gttcaatttc atgttctagt tgctttgttt   3360

tactggtttc acctgttcta ttaggtgtta catgctgttc atctgttaca ttgtcgatct   3420

gttcatggtg aacagcttta aatgcaccaa aaactcgtaa aagctctgat gtatctatct   3480

tttttacacc gttttcatct gtgcatatgg acagttttcc ctttgat                 3527
```

<210> SEQ ID NO 37
<211> LENGTH: 70
<212> TYPE: DNA
<213> ORGANISM: Artificial Sequence
<220> FEATURE:
<223> OTHER INFORMATION: delta-iclR-cure

<400> SEQUENCE: 37

```
aaatgatttc cacgatacag aaaaaagaga ctgtcatggg cagaatattg cctctgcccg     60

ccagaaaaag                                                             70
```

<210> SEQ ID NO 38
<211> LENGTH: 70
<212> TYPE: DNA
<213> ORGANISM: Artificial Sequence
<220> FEATURE:
<223> OTHER INFORMATION: delta-arcA-cure

<400> SEQUENCE: 38

```
ctgtttcgat ttagttggca atttaggtag caaactcggc tttaccaccg tcaaaaaaaa     60

cggcgctttt                                                             70
```

<210> SEQ ID NO 39
<211> LENGTH: 974
<212> TYPE: DNA
<213> ORGANISM: Artificial Sequence
<220> FEATURE:
<223> OTHER INFORMATION: delta-cas3::ugBp-sspB-pro-casA

<400> SEQUENCE: 39

```
caagacatgt gtatatcact gtaattcgat atttatgagc agcatcgaaa aatagcccgc     60

tgatatcatc gataatacta aaaaaacagg gaggctatta ccaggcatca aataaaacga    120

aaggctcagt cgaaagactg ggcctttcgt tttatctgtt gtttgtcggt gaacgctctc    180

tactagagtc acactggctc accttcgggt gggcctttct gcgtttatat ctttctgaca    240

ccttactatc ttacaaatgt aacaaaaaag ttatttttct gtaattcgag catgtcatgt    300

taccccgcga gcataaaacg cgtgtgtagg aggataatct atggatttgt cacagctaac    360

accacgtcgt ccctatctgc tgcgtgcatt ctatgagtgg ttgctggata accagctcac    420

gccgcacctg gtggtggatg tgacgctccc tggcgtgcag gttcctatgg aatatgcgcg    480

tgacgggcaa atcgtactca acattgcgcc gcgtgctgtc ggcaatctgg aactggcgaa    540

tgatgaggtg cgctttaacg cgcgctttgg tggcattccg cgtcaggttt ctgtgccgct    600
```

```
ggctgccgtg ctggctatct acgcccgtga aaatggcgca ggcacgatgt ttgagcctga    660

agctgcctac gatgaagata ccagcatcat gaatgatgaa gaggcatcgg cagacaacga    720

aaccgttatg tcggttattg atggcgacaa gccagatcac gatgatgaca ctcatcctga    780

cgatgaacct ccgcagccac cacgcggtgg tcgaccggca ttacgcgttg tgaagtaatt    840

gacggctagc tcagtcctag gtacagtgct agccatatga aggagaacaa atgaatttgc    900

ttattgataa ctggatccct gtacgcccgc gaaacggggg gaaagtccaa atcataaatc    960

tgcaatcgct atac                                                      974
```

<210> SEQ ID NO 40
<211> LENGTH: 1421
<212> TYPE: DNA
<213> ORGANISM: Artificial Sequence
<220> FEATURE:
<223> OTHER INFORMATION: gltA-DAS+4-ampR

<400> SEQUENCE: 40

```
gtattccgtc ttccatgttc accgtcattt tcgcaatggc acgtaccgtt ggctggatcg     60

cccactggag cgaaatgcac agtgacggta tgaagattgc ccgtccgcgt cagctgtata    120

caggatatga aaaacgcgac tttaaaagcg atatcaagcg tgcggccaac gatgaaaact    180

attctgaaaa ctatgcggat gcgtcttaat agtcctgacg gatggccttt ttgcgtttct    240

acaaactctt tttgtttatt tttctaaata cattcaaata tgtatccgct catgagacaa    300

taaccctgat aaatgcttca ataatattga aaaaggaaga gtatgagtat tcaacatttc    360

cgtgtcgccc ttattccctt ttttgcggca ttttgccttc ctgtttttgc tcacccagaa    420

acgctggtga aagtaaaaga tgctgaagat cagttgggtg cacgagtggg ttacatcgaa    480

ctggatctca acagcggtaa gatccttgag agttttcgcc ccgaagaacg ttttccaatg    540

atgagcactt ttaaagttct gctatgtggc gcggtattat cccgtgttga cgccgggcaa    600

gagcaactcg gtcgccgcat acactattct cagaatgact tggttgagta ctcaccagtc    660

acagaaaagc atcttacgga tggcatgaca gtaagagaat tatgcagtgc tgccataacc    720

atgagtgata acactgcggc caacttactt ctgacaacga tcggaggacc gaaggagcta    780

accgcttttt tgcacaacat gggggatcat gtaactcgcc ttgatcgttg ggaaccggag    840

ctgaatgaag ccataccaaa cgacgagcgt gacaccacga tgcctacagc aatggcaaca    900

acgttgcgca aactattaac tggcgaacta cttactctag cttcccggca acaattaata    960

gactggatgg aggcggataa agttgcagga ccacttctgc gctcggccct tccggctggc   1020

tggtttattg ctgataaatc tggagccggt gagcgtgggt ctcgcggtat cattgcagca   1080

ctggggccag atggtaagcc ctcccgtatc gtagttatct acacgacggg gagtcaggca   1140

actatggatg aacgaaatag acagatcgct gagataggtg cctcactgat taagcattgg   1200

taactgtcag actaatggtt gattgctaag ttgtaaatat tttaacccgc cgttcatatg   1260

gcgggttgat tttatatgc ctaaacacaa aaaattgtaa aaataaaatc cattaacaga   1320

cctatataga tatttaaaaa gaatagaaca gctcaaatta tcagcaaccc aatactttca   1380

attaaaaact tcatggtagt cgcatttata accctatgaa a                       1421
```

<210> SEQ ID NO 41
<211> LENGTH: 1078
<212> TYPE: DNA
<213> ORGANISM: Artificial Sequence
<220> FEATURE:
<223> OTHER INFORMATION: gltA-DAS+4-purR

<400> SEQUENCE: 41

```
accgtcattt tcgcaatggc acgtaccgtt ggctggatcg cccactggag cgaaatgcac     60
agtgacggta tgaagattgc ccgtccgcgt cagctgtata caggatatga aaaacgcgac    120
tttaaaagcg atatcaagcg tgcggccaac gatgaaaact attctgaaaa ctatgcggat    180
gcgtcttaat cctgacggat ggcctttttg cgtttctaca aactcttttt gtttattttt    240
ctaaatacat tcaaatatgt atccgctcat gagacaataa ccctgataaa tgcttcaata    300
atattgaaaa aggaagagta tgactgaata caagcccacg gtacgcttgg cgacgcgcga    360
cgatgttccc cgcgctgttc gtacattagc tgcggccttt gcagattacc cagcgacgcg    420
ccatacggtc gatccggacc gccatatcga gcgtgtcaca gaattgcagg aacttttctt    480
aactcgcgtg ggccttgaca tcggaaaggt ctgggtggct gacgatggcg ctgcagtggc    540
tgtttggacc actccggaga gtgtagaggc tggtgcagtg ttcgccgaaa ttggtcctcg    600
tatggccgaa ttaagtggaa gtcgtctggc agcccaacaa caaatggaag ggttgcttgc    660
gccccaccgt ccgaaagaac ccgcgtggtt ccttgccacc gttggagtaa gcccagatca    720
ccaggggaag ggtttaggat ctgccgtagt tttaccaggt gtggaggcag cagaacgtgc    780
gggagttccg gccttccttg agacgtcggc gccgcgcaat ttaccgtttt acgaacgtct    840
tggattcacc gttacggcgg acgtggaggt gccggaggga ccccgtactt ggtgtatgac    900
tcgtaaaccg ggagcctgat aatggttgat tgctaagttg taaatatttt aacccgccgt    960
tcatatggcg ggttgatttt tatatgccta aacacaaaaa attgtaaaaa taaaatccat   1020
taacagacct atatagatat ttaaaaagaa tagaacagct caaattatca gcaaccca     1078
```

<210> SEQ ID NO 42
<211> LENGTH: 869
<212> TYPE: DNA
<213> ORGANISM: Artificial Sequence
<220> FEATURE:
<223> OTHER INFORMATION: gltA-DAS+4-zeoR

<400> SEQUENCE: 42

```
gtattccgtc ttccatgttc accgtcattt tcgcaatggc acgtaccgtt ggctggatcg     60
cccactggag cgaaatgcac agtgacggta tgaagattgc ccgtccgcgt cagctgtata    120
caggatatga aaaacgcgac tttaaaagcg atatcaagcg tgcggccaac gatgaaaact    180
attctgaaaa ctatgcggat gcgtcttaat agttgacaat taatcatcgg catagtatat    240
cggcatagta taatacgact cactatagga gggccatcat ggccaagttg accagtgccg    300
ttccggtgct caccgcgcgc gacgtcgccg gagcggtcga gttctggacc gaccggctcg    360
ggttctcccg ggacttcgtg gaggacgact tcgccggtgt ggtccgggac gacgtgaccc    420
tgttcatcag cgcggtccag gaccaggtgg tgccggacaa caccctggcc tgggtgtggg    480
tgcgcggcct ggacgagctg tacgccgagt ggtcggaggt cgtgtccacg aacttccggg    540
acgcctccgg gccggccatg accgagatcg gcgagcagcc gtgggggcgg gagttcgccc    600
tgcgcgaccc ggccggcaac tgcgtgcact ttgtggcaga ggagcaggac tgaggataag    660
taatggttga ttgctaagtt gtaaatattt taacccgccg ttcatatggc gggttgattt    720
ttatatgcct aaacacaaaa aattgtaaaa ataaaatcca ttaacagacc tatatagata    780
tttaaaaaga atagaacagc tcaaattatc agcaacccaa tactttcaat taaaaacttc    840
atggtagtcg catttataac cctatgaaa                                      869
```

<210> SEQ ID NO 43
<211> LENGTH: 1000
<212> TYPE: DNA
<213> ORGANISM: Artificial Sequence
<220> FEATURE:
<223> OTHER INFORMATION: lpd-DAS+4-gentR

<400> SEQUENCE: 43

```
gcggcgagct gctgggtgaa atcggcctgg caatcgaaat gggttgtgat gctgaagaca     60
tcgcactgac catccacgcg cacccgactc tgcacgagtc tgtgggcctg gcggcagaag    120
tgttcgaagg tagcattacc gacctgccga acccgaaagc gaagaagaag gcggccaacg    180
atgaaaacta ttctgaaaac tatgcggatg cgtcttaata gcgaatccat gtgggagttt    240
attcttgaca cagatattta tgatataata actgagtaag cttaacataa ggaggaaaaa    300
catatgttac gcagcagcaa cgatgttacg cagcagggca gtcgccctaa aacaaagtta    360
ggtggctcaa gtatgggcat cattcgcaca tgtaggctcg gccctgacca agtcaaatcc    420
atgcgggctg ctcttgatct tttcggtcgt gagttcggag acgtagccac ctactcccaa    480
catcagccgg actccgatta cctcgggaac ttgctccgta gtaagacatt catcgcgctt    540
gctgccttcg accaagaagc ggttgttggc gctctcgcgg cttacgttct gcccaagttt    600
gagcagccgc gtagtgagat ctatatctat gatctcgcag tctccggcga gcaccggagg    660
cagggcattg ccaccgcgct catcaatctc ctcaagcatg aggccaacgc gcttggtgct    720
tatgtgatct acgtgcaagc agattacggt gacgatcccg cagtggctct ctatacaaag    780
ttgggcatac gggaagaagt gatgcacttt gatatcgacc caagtaccgc cacctaattt    840
ttcgtttgcc ggaacatccg gcaattaaaa aagcggctaa ccacgccgct ttttttacgt    900
ctgcaattta cctttccagt cttcttgctc cacgttcaga gagacgttcg catactgctg    960
accgttgctc gttattcagc ctgacagtat ggttactgtc                          1000
```

<210> SEQ ID NO 44
<211> LENGTH: 898
<212> TYPE: DNA
<213> ORGANISM: Artificial Sequence
<220> FEATURE:
<223> OTHER INFORMATION: zwf-DAS+4-bsdR

<400> SEQUENCE: 44

```
gaagtggaag aagcctggaa atgggtagac tccattactg aggcgtgggc gatggacaat     60
gatgcgccga aaccgtatca ggccggaacc tggggacccg ttgcctcggt ggcgatgatt    120
acccgtgatg gtcgttcctg gaatgagttt gaggcggcca acgatgaaaa ctattctgaa    180
aactatgcgg atgcgtctta atagttgaca attaatcatc ggcatagtat atcggcatag    240
tataatacga ctcactatag gagggccatc atgaagacct tcaacatctc tcagcaggat    300
ctggagctgg tggaggtcgc cactgagaag atcaccatgc tctatgagga caacaagcac    360
catgtcgggg cggccatcag gaccaagact ggggagatca tctctgctgt ccacattgag    420
gcctacattg gcagggtcac tgtctgtgct gaagccattg ccattgggtc tgctgtgagc    480
aacgggcaga aggactttga caccattgtg gctgtcaggc acccctactc tgatgaggtg    540
gacagatcca tcagggtggt cagcccctgt ggcatgtgca gagagctcat ctctgactat    600
gctcctgact gctttgtgct cattgagatg aatggcaagc tggtcaaaac caccattgag    660
gaactcatcc ccctcaagta caccaggaac taaagtaata tctgcgctta tcctttatgg    720
ttattttacc ggtaacatga tcttgcgcag attgtagaac aatttttaca ctttcaggcc    780
```

```
tcgtgcggat tcacccacga ggcttttttt attacactga ctgaaacgtt tttgccctat    840

gagctccggt tacaggcgtt tcagtcataa atcctctgaa tgaaacgcgt tgtgaatc      898
```

<210> SEQ ID NO 45
<211> LENGTH: 1454
<212> TYPE: DNA
<213> ORGANISM: Artificial Sequence
<220> FEATURE:
<223> OTHER INFORMATION: pykA-DAS+4:ampR

<400> SEQUENCE: 45

```
tgaacctgac tgctctctat cgtggcgtta cgccggtgca ctttgatagc gctaatgacg     60

gcgtagcagc tgccagcgaa gcggttaatc tgctgcgcga taaaggttac ttgatgtctg    120

gtgacctggt gattgtcacc cagggcgacg tgatgagtac cgtgggttct actaatacca    180

cgcgtatttt aacggtagag gcggccaacg atgaaaacta ttctgaaaac tatgcggatg    240

cgtcttaata gtcctgacgg atggcctttt tgcgtttcta caaactcttt ttgtttattt    300

ttctaaatac attcaaatat gtatccgctc atgagacaat aaccctgata aatgcttcaa    360

taatattgaa aaaggaagag tatgagtatt caacatttcc gtgtcgccct tattcccttt    420

tttgcggcat tttgccttcc tgtttttgct cacccagaaa cgctggtgaa agtaaaagat    480

gctgaagatc agttgggtgc acgagtgggt tacatcgaac tggatctcaa cagcggtaag    540

atccttgaga gttttcgccc cgaagaacgt tttccaatga tgagcacttt taaagttctg    600

ctatgtggcg cggtattatc ccgtgttgac gccgggcaag agcaactcgg tcgccgcata    660

cactattctc agaatgactt ggttgagtac tcaccagtca cagaaaagca tcttacggat    720

ggcatgacag taagagaatt atgcagtgct gccataacca tgagtgataa cactgcggcc    780

aacttacttc tgacaacgat cggaggaccg aaggagctaa ccgctttttt gcacaacatg    840

ggggatcatg taactcgcct tgatcgttgg gaaccggagc tgaatgaagc cataccaaac    900

gacgagcgtg acaccacgat gcctacagca atggcaacaa cgttgcgcaa actattaact    960

ggcgaactac ttactctagc ttcccggcaa caattaatag actggatgga ggcggataaa   1020

gttgcaggac cacttctgcg ctcggccctt ccggctggct ggtttattgc tgataaatct   1080

ggagccggtg agcgtgggtc tcgcggtatc attgcagcac tggggccaga tggtaagccc   1140

tcccgtatcg tagttatcta cacgacgggg agtcaggcaa ctatggatga acgaaataga   1200

cagatcgctg agataggtgc ctcactgatt aagcattggt aactgtcaga ctaagtacgt   1260

tgccggatgc ggcgaaaacg ccacatccgg cctacagttc aatgatagtt caacagattt   1320

cgaatattct gaagcaaact tgaacttatc atcaggcgaa ggcctctcct cgcgagaggc   1380

tttttattt gatgggataa agatctttgc gcttatacgg ctggatttcg cccggtttgc    1440

gagttttcag caat                                                     1454
```

<210> SEQ ID NO 46
<211> LENGTH: 1310
<212> TYPE: DNA
<213> ORGANISM: Artificial Sequence
<220> FEATURE:
<223> OTHER INFORMATION: pykF-DAS+4:purr

<400> SEQUENCE: 46

```
aaacggctca tcagttggta ctgagcaaag gcgttgtgcc gcagcttgtt aaagagatca     60

cttctactga tgatttctac cgtctgggta aagaactggc tctgcagagc ggtctggcac    120
```

```
acaaaggtga cgttgtagtt atggtttctg gtgcactggt accgagcggc actactaaca    180

ccgcatctgt tcacgtcctg gcggccaacg atgaaaacta ttctgaaaac tatgcggatg    240

cgtcttaatc ctgacggatg gcctttttgc gtttctacaa actctttttg tttatttttc    300

taaatacatt caaatatgta tccgctcatg agacaataac cctgataaat gcttcaataa    360

tattgaaaaa ggaagagtat gactgaatac aagcccacgg tacgcttggc gacgcgcgac    420

gatgttcccc gcgctgttcg tacattagct gcggcctttg cagattaccc agcgacgcgc    480

catacggtcg atccggaccg ccatatcgag cgtgtcacag aattgcagga acttttctta    540

actcgcgtgg gccttgacat cggaaaggtc tgggtggctg acgatggcgc tgcagtggct    600

gtttggacca ctccggagag tgtagaggct ggtgcagtgt tcgccgaaat tggtcctcgt    660

atggccgaat taagtggaag tcgtctggca gcccaacaac aaatggaagg gttgcttgcg    720

ccccaccgtc cgaaagaacc cgcgtggttc cttgccaccg ttggagtaag cccagatcac    780

caggggaagg gtttaggatc tgccgtagtt ttaccaggtg tggaggcagc agaacgtgcg    840

ggagttccgg ccttccttga gacgtcggcg ccgcgcaatt taccgtttta cgaacgtctt    900

ggattcaccg ttacggcgga cgtggaggtg ccggagggac cccgtacttg gtgtatgact    960

cgtaaaccgg gagcctgata atattgcttt tgtgaattaa tttgtatatc gaagcgccct   1020

gatgggcgct ttttttattt aatcgataac cagaagcaat aaaaaatcaa atcggatttc   1080

actatataat ctcactttat ctaagatgaa tccgatggaa gcatcctgtt ttctctcaat   1140

ttttttatct aaaacccagc gttcgatgct tctttgagcg aacgatcaaa aataagtgcc   1200

ttcccatcaa aaaaatattc tcaacataaa aactttgtg taatacttgt aacgctacat   1260

ggagattaac tcaatctaga gggtattaat aatgaaagct actaaactgg              1310


<210> SEQ ID NO 47
<211> LENGTH: 43
<212> TYPE: DNA
<213> ORGANISM: Artificial Sequence
<220> FEATURE:
<223> OTHER INFORMATION: Primer:  AM512_gRNAmgsA

<400> SEQUENCE: 47

ctgtatgcaa caggcactac gttttagagc tagaaatagc aag                        43


<210> SEQ ID NO 48
<211> LENGTH: 23
<212> TYPE: DNA
<213> ORGANISM: Artificial Sequence
<220> FEATURE:
<223> OTHER INFORMATION: Primer: AM225_sgRNA_F3

<400> SEQUENCE: 48

gtgctcagta tctctatcac tga                                              23


<210> SEQ ID NO 49
<211> LENGTH: 43
<212> TYPE: DNA
<213> ORGANISM: Artificial Sequence
<220> FEATURE:
<223> OTHER INFORMATION: Primer: AM514_gRNAptsA

<400> SEQUENCE: 49

atgtgttctg atttgctgtg gttttagagc tagaaatagc aag                        43


<210> SEQ ID NO 50
<211> LENGTH: 23
```

<212> TYPE: DNA
<213> ORGANISM: Artificial Sequence
<220> FEATURE:
<223> OTHER INFORMATION: Primer: AM225_sgRNA_F3

<400> SEQUENCE: 50
gtgctcagta tctctatcac tga 23

<210> SEQ ID NO 51
<211> LENGTH: 43
<212> TYPE: DNA
<213> ORGANISM: Artificial Sequence
<220> FEATURE:
<223> OTHER INFORMATION: Primer: AM536_gRNAepd

<400> SEQUENCE: 51
taaatggctt cggtcgcatc gttttagagc tagaaatagc aag 43

<210> SEQ ID NO 52
<211> LENGTH: 23
<212> TYPE: DNA
<213> ORGANISM: Artificial Sequence
<220> FEATURE:
<223> OTHER INFORMATION: Primer: AM225_sgRNA_F3

<400> SEQUENCE: 52
gtgctcagta tctctatcac tga 23

<210> SEQ ID NO 53
<211> LENGTH: 43
<212> TYPE: DNA
<213> ORGANISM: Artificial Sequence
<220> FEATURE:
<223> OTHER INFORMATION: AM537_gRNAdhaL

<400> SEQUENCE: 53
ctttatcaga tgttccgcga gttttagagc tagaaatagc aag 43

<210> SEQ ID NO 54
<211> LENGTH: 23
<212> TYPE: DNA
<213> ORGANISM: Artificial Sequence
<220> FEATURE:
<223> OTHER INFORMATION: Primer: AM225_sgRNA_F3

<400> SEQUENCE: 54
gtgctcagta tctctatcac tga 23

<210> SEQ ID NO 55
<211> LENGTH: 43
<212> TYPE: DNA
<213> ORGANISM: Artificial Sequence
<220> FEATURE:
<223> OTHER INFORMATION: Primer: AM550_gRNAeda

<400> SEQUENCE: 55
ggtgctgaat ccacagcagc gttttagagc tagaaatagc aag 43

<210> SEQ ID NO 56
<211> LENGTH: 23
<212> TYPE: DNA
<213> ORGANISM: Artificial Sequence
<220> FEATURE:
<223> OTHER INFORMATION: Primer: AM225_sgRNA_F3

<400> SEQUENCE: 56

```
gtgctcagta tctctatcac tga                                           23


<210> SEQ ID NO 57
<211> LENGTH: 86
<212> TYPE: DNA
<213> ORGANISM: Artificial Sequence
<220> FEATURE:
<223> OTHER INFORMATION: AM519_D ONmgsA

<400> SEQUENCE: 57

gcagcataag tgcttacagt aatctgtagg aaagttaact acggatcccc gattatcagc   60

gttatctcgc ggaccgtctg aagtaa                                        86


<210> SEQ ID NO 58
<211> LENGTH: 90
<212> TYPE: DNA
<213> ORGANISM: Artificial Sequence
<220> FEATURE:
<223> OTHER INFORMATION: AM549_D ONPtsA2

<400> SEQUENCE: 58

ccttttacag ttccagttca tgttgcagca ggctggcgat agcgttttgc ggcatgcttc   60

cggtttatcg caagttatga ggcggatcgc                                    90


<210> SEQ ID NO 59
<211> LENGTH: 90
<212> TYPE: DNA
<213> ORGANISM: Artificial Sequence
<220> FEATURE:
<223> OTHER INFORMATION: AM538_D ONepd

<400> SEQUENCE: 59

ccttttacag ttccagttca tgttgcagca ggctggcgat agcgttttgc ggcatgcttc   60

cggtttatcg caagttatga ggcggatcgc                                    90


<210> SEQ ID NO 60
<211> LENGTH: 90
<212> TYPE: DNA
<213> ORGANISM: Artificial Sequence
<220> FEATURE:
<223> OTHER INFORMATION: AM539_D ONdhaL

<400> SEQUENCE: 60

gattgactat cgaacgtaat ttaattggcg cgtactgcac ctcacgactg ggagaaggtg   60

tcggtgaatt agcccgtcag atgttaatga                                    90


<210> SEQ ID NO 61
<211> LENGTH: 90
<212> TYPE: DNA
<213> ORGANISM: Artificial Sequence
<220> FEATURE:
<223> OTHER INFORMATION: AM551_D ONeda

<400> SEQUENCE: 61

gccttctaca gcttcacgcg ccagcttagt aatgcggtcg taatcgcctg attacaaatt   60

tgtcgtctta aaaagtgata caggttgcgc                                    90


<210> SEQ ID NO 62
<211> LENGTH: 20
<212> TYPE: DNA
<213> ORGANISM: Artificial Sequence
<220> FEATURE:
<223> OTHER INFORMATION: Primer: AM525_byemgsA_F
```

<400> SEQUENCE: 62
ctgacccaca aacgcgaaat 20

<210> SEQ ID NO 63
<211> LENGTH: 20
<212> TYPE: DNA
<213> ORGANISM: Artificial Sequence
<220> FEATURE:
<223> OTHER INFORMATION: Primer: AM526_byemgsA_R

<400> SEQUENCE: 63
ggtggcgaga aaaccgtaag 20

<210> SEQ ID NO 64
<211> LENGTH: 20
<212> TYPE: DNA
<213> ORGANISM: Artificial Sequence
<220> FEATURE:
<223> OTHER INFORMATION: Primer: AM547_byeptsA_F2

<400> SEQUENCE: 64
cgcccgtcat taaatgctga 20

<210> SEQ ID NO 65
<211> LENGTH: 20
<212> TYPE: DNA
<213> ORGANISM: Artificial Sequence
<220> FEATURE:
<223> OTHER INFORMATION: Primer: AM548_byeptsA_R2

<400> SEQUENCE: 65
ggctaataac ccttgtgcgg 20

<210> SEQ ID NO 66
<211> LENGTH: 20
<212> TYPE: DNA
<213> ORGANISM: Artificial Sequence
<220> FEATURE:
<223> OTHER INFORMATION: Primer: AM540_byeEpd_F

<400> SEQUENCE: 66
ttcggctgga caaacattcc 20

<210> SEQ ID NO 67
<211> LENGTH: 20
<212> TYPE: DNA
<213> ORGANISM: Artificial Sequence
<220> FEATURE:
<223> OTHER INFORMATION: AM541_byeEpd_R

<400> SEQUENCE: 67
aacctgttga tcgtgcatgg 20

<210> SEQ ID NO 68
<211> LENGTH: 20
<212> TYPE: DNA
<213> ORGANISM: Artificial Sequence
<220> FEATURE:
<223> OTHER INFORMATION: Primer: AM542_byeDhaL_F

<400> SEQUENCE: 68
cgtctataac cgcctgacca 20

<210> SEQ ID NO 69

<211> LENGTH: 20
<212> TYPE: DNA
<213> ORGANISM: Artificial Sequence
<220> FEATURE:
<223> OTHER INFORMATION: Primer: AM543_byeDhaL_R

<400> SEQUENCE: 69
ttgtggatcg tcaattcccg 20

<210> SEQ ID NO 70
<211> LENGTH: 20
<212> TYPE: DNA
<213> ORGANISM: Artificial Sequence
<220> FEATURE:
<223> OTHER INFORMATION: Primer: AM552_byeEda_F

<400> SEQUENCE: 70
ctggtagacg aagcggaact 20

<210> SEQ ID NO 71
<211> LENGTH: 20
<212> TYPE: DNA
<213> ORGANISM: Artificial Sequence
<220> FEATURE:
<223> OTHER INFORMATION: Primer: AM553_byeEda_R

<400> SEQUENCE: 71
cctcgatcgg gcattttgac 20

<210> SEQ ID NO 72
<211> LENGTH: 92
<212> TYPE: DNA
<213> ORGANISM: Artificial Sequence
<220> FEATURE:
<223> OTHER INFORMATION: sgRNA/Primer name: pykA

<400> SEQUENCE: 72
tcgagttccc cgcgccagcg gggataaacc gtgacgatcg ctaaaaacga ctgtcactgt 60
ctcgagttcc ccgcgccagc ggggataaac cg 92

<210> SEQ ID NO 73
<211> LENGTH: 59
<212> TYPE: DNA
<213> ORGANISM: Artificial Sequence
<220> FEATURE:
<223> OTHER INFORMATION: sgRNA/Primer name: pykA-sgRNA-FOR

<400> SEQUENCE: 73
acgactgtca ctgtctcgag ttccccgcgc cagcggggat aaaccgaaaa aaaaaacccc 59

<210> SEQ ID NO 74
<211> LENGTH: 60
<212> TYPE: DNA
<213> ORGANISM: Artificial Sequence
<220> FEATURE:
<223> OTHER INFORMATION: sgRNA/Primer name: pykA-sgRNA-REV

<400> SEQUENCE: 74
ttttagcgat cgtcacggtt tatccccgct ggcgcgggga actcgaggtg gtaccagatc 60

<210> SEQ ID NO 75
<211> LENGTH: 92
<212> TYPE: DNA
<213> ORGANISM: Artificial Sequence
<220> FEATURE:
<223> OTHER INFORMATION: sgRNA/Primer name: pykF

<400> SEQUENCE: 75
tcgagttccc cgcgccagcg gggataaacc gcaccaccac tttcgtaata ccggattcgc 60
ttcgagttcc ccgcgccagc ggggataaac cg 92

<210> SEQ ID NO 76
<211> LENGTH: 59
<212> TYPE: DNA
<213> ORGANISM: Artificial Sequence
<220> FEATURE:
<223> OTHER INFORMATION: sgRNA/Primer name: pykF-sgRNA-FOR

<400> SEQUENCE: 76
aataccggat tcgcttcgag ttccccgcgc cagcggggat aaaccgaaaa aaaaaacccc 59

<210> SEQ ID NO 77
<211> LENGTH: 60
<212> TYPE: DNA
<213> ORGANISM: Artificial Sequence
<220> FEATURE:
<223> OTHER INFORMATION: sgRNA/Primer name: pykF-sgRNA-REV

<400> SEQUENCE: 77
acgaaagtgg tggtgcggtt tatccccgct ggcgcgggga actcgaggtg gtaccagatc 60

<210> SEQ ID NO 78
<211> LENGTH: 153
<212> TYPE: DNA
<213> ORGANISM: Artificial Sequence
<220> FEATURE:
<223> OTHER INFORMATION: sgRNA/Primer name: pykA-pykF

<400> SEQUENCE: 78
tcgagttccc cgcgccagcg gggataaacc gtgacgatcg ctaaaaacga ctgtcactgt 60
ctcgagttcc ccgcgccagc ggggataaac cgcaccacca ctttcgtaat accggattcg 120
cttcgagttc cccgcgccag cggggataaa ccg 153

<210> SEQ ID NO 79
<211> LENGTH: 59
<212> TYPE: DNA
<213> ORGANISM: Artificial Sequence
<220> FEATURE:
<223> OTHER INFORMATION: sgRNA/Primer name: pykF-FOR

<400> SEQUENCE: 79
aataccggat tcgcttcgag ttccccgcgc cagcggggat aaaccgaaaa aaaaaacccc 59

<210> SEQ ID NO 80
<211> LENGTH: 28
<212> TYPE: DNA
<213> ORGANISM: Artificial Sequence
<220> FEATURE:
<223> OTHER INFORMATION: sgRNA/Primer name: pCASCADE-REV

<400> SEQUENCE: 80
cttgcccgcc tgatgaatgc tcatccgg 28

<210> SEQ ID NO 81
<211> LENGTH: 28
<212> TYPE: DNA
<213> ORGANISM: Artificial Sequence
<220> FEATURE:
<223> OTHER INFORMATION: sgRNA/Primer name: pCASCADE-FOR

<400> SEQUENCE: 81
ccggatgagc attcatcagg cgggcaag 28

<210> SEQ ID NO 82
<211> LENGTH: 60
<212> TYPE: DNA
<213> ORGANISM: Artificial Sequence
<220> FEATURE:
<223> OTHER INFORMATION: sgRNA/Primer name: pykA-REV

<400> SEQUENCE: 82
acgaaagtgg tggtgcggtt tatccccgct ggcgcgggga actcgaggtg gtaccagatc 60

<210> SEQ ID NO 83
<211> LENGTH: 215
<212> TYPE: DNA
<213> ORGANISM: Artificial Sequence
<220> FEATURE:
<223> OTHER INFORMATION: sgRNA/Primer name: gltA1-pykA-pykF

<400> SEQUENCE: 83
tcgagttccc cgcgccagcg gggataaacc gaaaagcata taatgcgtaa aagttatgaa 60
gttcgagttc cccgcgccag cggggataaa ccgtgacgat cgctaaaaac gactgtcact 120
gtctcgagtt ccccgcgcca gcggggataa accgcaccac cactttcgta ataccggatt 180
cgcttcgagt tccccgcgcc agcggggata aaccg 215

<210> SEQ ID NO 84
<211> LENGTH: 37
<212> TYPE: DNA
<213> ORGANISM: Artificial Sequence
<220> FEATURE:
<223> OTHER INFORMATION: sgRNA/Primer name: pykA-FOR

<400> SEQUENCE: 84
gcgccagcgg ggataaaccg tgacgatcgc taaaaac 37

<210> SEQ ID NO 85
<211> LENGTH: 47
<212> TYPE: DNA
<213> ORGANISM: Artificial Sequence
<220> FEATURE:
<223> OTHER INFORMATION: sgRNA/Primer name: gltA1-REV

<400> SEQUENCE: 85
cggtttatcc ccgctggcgc ggggaactcg aacttcataa cttttac 47

<210> SEQ ID NO 86
<211> LENGTH: 216
<212> TYPE: DNA
<213> ORGANISM: Artificial Sequence
<220> FEATURE:
<223> OTHER INFORMATION: sgRNA/Primer name: gltA2-pykA-pykF

<400> SEQUENCE: 86
tcgagttccc cgcgccagcg gggataaacc gtattgacca attcattcgg gacagttatt 60
agttcgagtt ccccgcgcca gcggggataa accgtgacga tcgctaaaaa cgactgtcac 120
tgtctcgagt tccccgcgcc agcggggata aaccgcacca ccactttcgt aataccggat 180
tcgcttcgag ttccccgcgc cagcggggat aaaccg 216

<210> SEQ ID NO 87
<211> LENGTH: 37

<212> TYPE: DNA
<213> ORGANISM: Artificial Sequence
<220> FEATURE:
<223> OTHER INFORMATION: sgRNA/Primer name:pykA-FOR

<400> SEQUENCE: 87
gcgccagcgg ggataaaccg tgacgatcgc taaaaac 37

<210> SEQ ID NO 88
<211> LENGTH: 44
<212> TYPE: DNA
<213> ORGANISM: Artificial Sequence
<220> FEATURE:
<223> OTHER INFORMATION: sgRNA/Primer name:gltA2-REV

<400> SEQUENCE: 88
cggtttatcc ccgctggcgc ggggaactcg aactaataac tgtc 44

<210> SEQ ID NO 89
<211> LENGTH: 214
<212> TYPE: DNA
<213> ORGANISM: Artificial Sequence
<220> FEATURE:
<223> OTHER INFORMATION: sgRNA/Primer name: zwf-pykA-pykF

<400> SEQUENCE: 89
tcgagttccc cgcgccagcg gggataaacc gctcgtaaaa gcagtacagt gcaccgtaag 60
atcgagttcc ccgcgccagc ggggataaac cgtgacgatc gctaaaaacg actgtcactg 120
tctcgagttc cccgcgccag cggggataaa ccgcaccacc actttcgtaa taccggattc 180
gcttcgagtt ccccgcgcca gcggggataa accg 214

<210> SEQ ID NO 90
<211> LENGTH: 37
<212> TYPE: DNA
<213> ORGANISM: Artificial Sequence
<220> FEATURE:
<223> OTHER INFORMATION: sgRNA/Primer name: pykA-FOR

<400> SEQUENCE: 90
gcgccagcgg ggataaaccg tgacgatcgc taaaaac 37

<210> SEQ ID NO 91
<211> LENGTH: 49
<212> TYPE: DNA
<213> ORGANISM: Artificial Sequence
<220> FEATURE:
<223> OTHER INFORMATION: sgRNA/Primer name: zwf-REV

<400> SEQUENCE: 91
cggtttatcc ccgctggcgc ggggaactcg atcttacggt gcactgtac 49

<210> SEQ ID NO 92
<211> LENGTH: 278
<212> TYPE: DNA
<213> ORGANISM: Artificial Sequence
<220> FEATURE:
<223> OTHER INFORMATION: sgRNA/Primer name: gltA1-gltA2-pykA-pykF

<400> SEQUENCE: 92
tcgagttccc cgcgccagcg gggataaacc gaaaagcata taatgcgtaa aagttatgaa 60
gttcgagttc cccgcgccag cggggataaa ccgtattgac caattcattc gggacagtta 120
ttagttcgag ttccccgcgc cagcggggat aaaccgtgac gatcgctaaa aacgactgtc 180

```
actgtctcga gttccccgcg ccagcgggga taaaccgcac caccactttc gtaataccgg    240

attcgcttcg agttccccgc gccagcgggg ataaaccg                            278


<210> SEQ ID NO 93
<211> LENGTH: 37
<212> TYPE: DNA
<213> ORGANISM: Artificial Sequence
<220> FEATURE:
<223> OTHER INFORMATION: sgRNA/Primer name:  pykA-FOR

<400> SEQUENCE: 93

gcgccagcgg ggataaaccg tgacgatcgc taaaaac                              37


<210> SEQ ID NO 94
<211> LENGTH: 44
<212> TYPE: DNA
<213> ORGANISM: Artificial Sequence
<220> FEATURE:
<223> OTHER INFORMATION: sgRNA/Primer name: gltA2-REV

<400> SEQUENCE: 94

cggtttatcc ccgctggcgc ggggaactcg aactaataac tgtc                      44


<210> SEQ ID NO 95
<211> LENGTH: 276
<212> TYPE: DNA
<213> ORGANISM: Artificial Sequence
<220> FEATURE:
<223> OTHER INFORMATION: sgRNA/Primer name: gltA1-zwf-pykA-pykF

<400> SEQUENCE: 95

tcgagttccc cgcgccagcg gggataaacc gaaaagcata taatgcgtaa aagttatgaa     60

gttcgagttc cccgcgccag cggggataaa ccgctcgtaa aagcagtaca gtgcaccgta    120

agatcgagtt ccccgcgcca gcggggataa accgtgacga tcgctaaaaa cgactgtcac    180

tgtctcgagt tccccgcgcc agcggggata aaccgcacca ccactttcgt aataccggat    240

tcgcttcgag ttccccgcgc cagcggggat aaaccg                              276


<210> SEQ ID NO 96
<211> LENGTH: 37
<212> TYPE: DNA
<213> ORGANISM: Artificial Sequence
<220> FEATURE:
<223> OTHER INFORMATION: sgRNA/Primer name: pykA-FOR

<400> SEQUENCE: 96

gcgccagcgg ggataaaccg tgacgatcgc taaaaac                              37


<210> SEQ ID NO 97
<211> LENGTH: 49
<212> TYPE: DNA
<213> ORGANISM: Artificial Sequence
<220> FEATURE:
<223> OTHER INFORMATION: sgRNA/Primer name:zwf-REV

<400> SEQUENCE: 97

cggtttatcc ccgctggcgc ggggaactcg atcttacggt gcactgtac                 49


<210> SEQ ID NO 98
<211> LENGTH: 277
<212> TYPE: DNA
<213> ORGANISM: Artificial Sequence
<220> FEATURE:
<223> OTHER INFORMATION: sgRNA/Primer name: gltA2-zwf-pykA-pykF
```

<400> SEQUENCE: 98
tcgagttccc cgcgccagcg gggataaacc gtattgacca attcattcgg gacagttatt 60
agttcgagtt ccccgcgcca gcggggataa accgctcgta aaagcagtac agtgcaccgt 120
aagatcgagt tccccgcgcc agcggggata aaccgtgacg atcgctaaaa acgactgtca 180
ctgtctcgag ttccccgcgc cagcggggat aaaccgcacc accactttcg taataccgga 240
ttcgcttcga gttccccgcg ccagcgggga taaaccg 277

<210> SEQ ID NO 99
<211> LENGTH: 37
<212> TYPE: DNA
<213> ORGANISM: Artificial Sequence
<220> FEATURE:
<223> OTHER INFORMATION: sgRNA/Primer name:pykA-FOR

<400> SEQUENCE: 99
gcgccagcgg ggataaaccg tgacgatcgc taaaaac 37

<210> SEQ ID NO 100
<211> LENGTH: 49
<212> TYPE: DNA
<213> ORGANISM: Artificial Sequence
<220> FEATURE:
<223> OTHER INFORMATION: sgRNA/Primer name: zwf-REV

<400> SEQUENCE: 100
cggtttatcc ccgctggcgc ggggaactcg atcttacggt gcactgtac 49

<210> SEQ ID NO 101
<211> LENGTH: 339
<212> TYPE: DNA
<213> ORGANISM: Artificial Sequence
<220> FEATURE:
<223> OTHER INFORMATION: sgRNA/Primer name:gltA1-gltA2-zwf-pykA-pykF

<400> SEQUENCE: 101
tcgagttccc cgcgccagcg gggataaacc gaaaagcata taatgcgtaa aagttatgaa 60
gttcgagttc cccgcgccag cggggataaa ccgtattgac caattcattc gggacagtta 120
ttagttcgag ttccccgcgc cagcggggat aaaccgctcg taaaagcagt acagtgcacc 180
gtaagatcga gttccccgcg ccagcgggga taaaccgtga cgatcgctaa aaacgactgt 240
cactgtctcg agttccccgc gccagcgggg ataaaccgca ccaccacttt cgtaataccg 300
gattcgcttc gagttccccg cgccagcggg gataaaccg 339

<210> SEQ ID NO 102
<211> LENGTH: 37
<212> TYPE: DNA
<213> ORGANISM: Artificial Sequence
<220> FEATURE:
<223> OTHER INFORMATION: sgRNA/Primer name: pykA-FOR

<400> SEQUENCE: 102
gcgccagcgg ggataaaccg tgacgatcgc taaaaac 37

<210> SEQ ID NO 103
<211> LENGTH: 49
<212> TYPE: DNA
<213> ORGANISM: Artificial Sequence -continued

```
<220> FEATURE:
<223> OTHER INFORMATION: sgRNA/Primer name: zwf-REV

<400> SEQUENCE: 103

cggtttatcc ccgctggcgc ggggaactcg atcttacggt gcactgtac              49
```

COMPOSITIONS AND METHODS FOR THE PRODUCTION OF PYRUVIC ACID AND RELATED PRODUCTS USING DYNAMIC METABOLIC CONTROL

CROSS-REFERENCE TO RELATED APPLICATIONS

This application claims priority to U.S. Provisional Patent Application No. 62/687,874, filed Jun. 21, 2018, which is incorporated by reference herein in its entirety.

FEDERALLY SPONSORED RESEARCH OR DEVELOPMENT

This invention was made with government support under Federal Grant No. MCB-1445726 awarded by the National Science Foundation and Federal Contract No. HR0011-14-C-0075 awarded by the United States Department of Defense and Federal Grant No. ONR YIP 12043956 awarded by the United States Department of Defense, and N00014-16-1-2558 awarded by NAVY/ONR. The government has certain rights in the invention.

FIELD OF THE INVENTION

This invention relates to metabolically engineered microorganisms, such as bacterial strains, and bioprocesses utilizing such strains. These strains provide dynamic control of metabolic pathways resulting in the production of pyruvic acid or pyruvate and pyruvate derived products.

BACKGROUND OF THE INVENTION

Petroleum is the primary feedstock, not only for the fuels we use but the majority of the chemicals we consume as well. The chemical industry is heavily reliant on this non-renewable resource. Replacement of petroleum with renewable feedstocks ensures longer-term viability and environmental sustainability. Novel fermentation based processes to make chemicals have been a contributing technology, enabling the change to renewable feedstocks (Werpy & Peterson, Top Value Added Chemicals from Biomass. Volume I—Results of Screening for Potential Candidates from Sugars and Synthesis Gas., Yixiang et al. "Green" Chemicals from Renewable Agricultural Biomass—A Mini Review. The Open Agriculture Journal, 2008). These fermentation processes have made rapid advancements in recent years due to technology developments in the fields of fermentation science, synthetic biology, as well as metabolic and enzyme engineering (Jarboe, L. R., et al., Metabolic engineering for production of biorenewable fuels and chemicals: contributions of synthetic biology. J Biomed Biotechnol, 2010 and Lee, J. W., et al., Systems metabolic engineering of microorganisms for natural and non-natural chemicals. Nat Chem Biol, 2012). Despite these substantial advances, most successful examples of rational directed engineering approaches have also greatly relied on numerous cycles of trial and error. The field of metabolic engineering has historically been limited in predicting the behavior of complex biological systems in-vivo, from simplified models and basic in-vitro biochemical principles. Such rational approaches have required significant a priori knowledge of microbial physiology that in many cases is incomplete. This is particularly true for complex phenotypes that require an intricate balance between the activities of many seemingly unrelated gene products. In many cases, it has proven much more difficult than expected to integrate a possibly well characterized production pathway into a living host and balance the complex requirements of both biomass growth and production.

Pyruvic acid (pyruvate at neutral pH) is a three carbon oxo-monocarboxylic acid, also known as 2-oxopropanoic acid, 2-ketopropionic acid or acetylformic acid. Having both a keto and carboxylic groups, pyruvate is a potential precursor for many chemicals, pharmaceuticals, food additives, and polymers, useful in the synthesis of its esters such as ethyl pyruvate as well as L-DOPA, N-acetyl-D-neuraminic acid, and (R)-phenylacetylcarbinol. In addition, pyruvate is a central metabolite with significant potential as precursor to numerous additional commercial products that can be produced via subsequent biochemical conversions either in vitro or in vivo.

SUMMARY OF THE INVENTION

Provided herein are microbial strains for scalable biofermentation processes vie the use of synthetic metabolic valves (SMVs) that can decouple growth from product formation. The described strains provide dynamic control of metabolic pathways, including pathways that when altered have negative effects on microorganism growth.

Also provided are methods to construct microbial strains using controllable synthetic metabolic valves for the production of pyruvate or pyruvic acid as well as derivatives and further metabolic products of pyruvate or pyruvic acid. Synthetic metabolic valves are used to controllably reduce or eliminate flux through one more metabolic pathways known to produce pyruvic acid, resulting in strains unexpectedly producing high rates of pyruvic acid through alternative pathways. Flux is reduced or eliminated through one or more metabolic pathways, the enzymes of which may be essential for microbial growth in a given environment. The genetically modified microorganisms described herein use one or more synthetic metabolic valves alone or in combination thereby enabling dynamic control over metabolic pathways resulting in pyruvate production. Additional genetic modifications including gene deletions may be added to a microorganism to provide improved pyruvate production.

Provided herein are multi-stage bioprocesses that use the described genetically modified microorganism containing one or more synthetic metabolic valves that provide dynamic flux control. In certain embodiments, carbon feedstocks can include, but are not limited to the sugars: glucose, sucrose xylose, arabinose, mannose, lactose, or alternatively carbon dioxide, carbon monoxide, methane, methanol, formaldehyde, or oils. Additional genetic modifications may be added to a microorganism to provide further conversion of pyruvate to additional chemical or fuel products.

BRIEF DESCRIPTION OF THE DRAWINGS

The novel features of the invention are set forth with particularity in the claims. A better understanding of the features and advantages of the present invention will be obtained by reference to the following detailed description that sets forth illustrative embodiments, in which the principles of the invention are used, and the accompanying drawings of which:

DETAILED DESCRIPTION OF THE INVENTION

Figure 1:
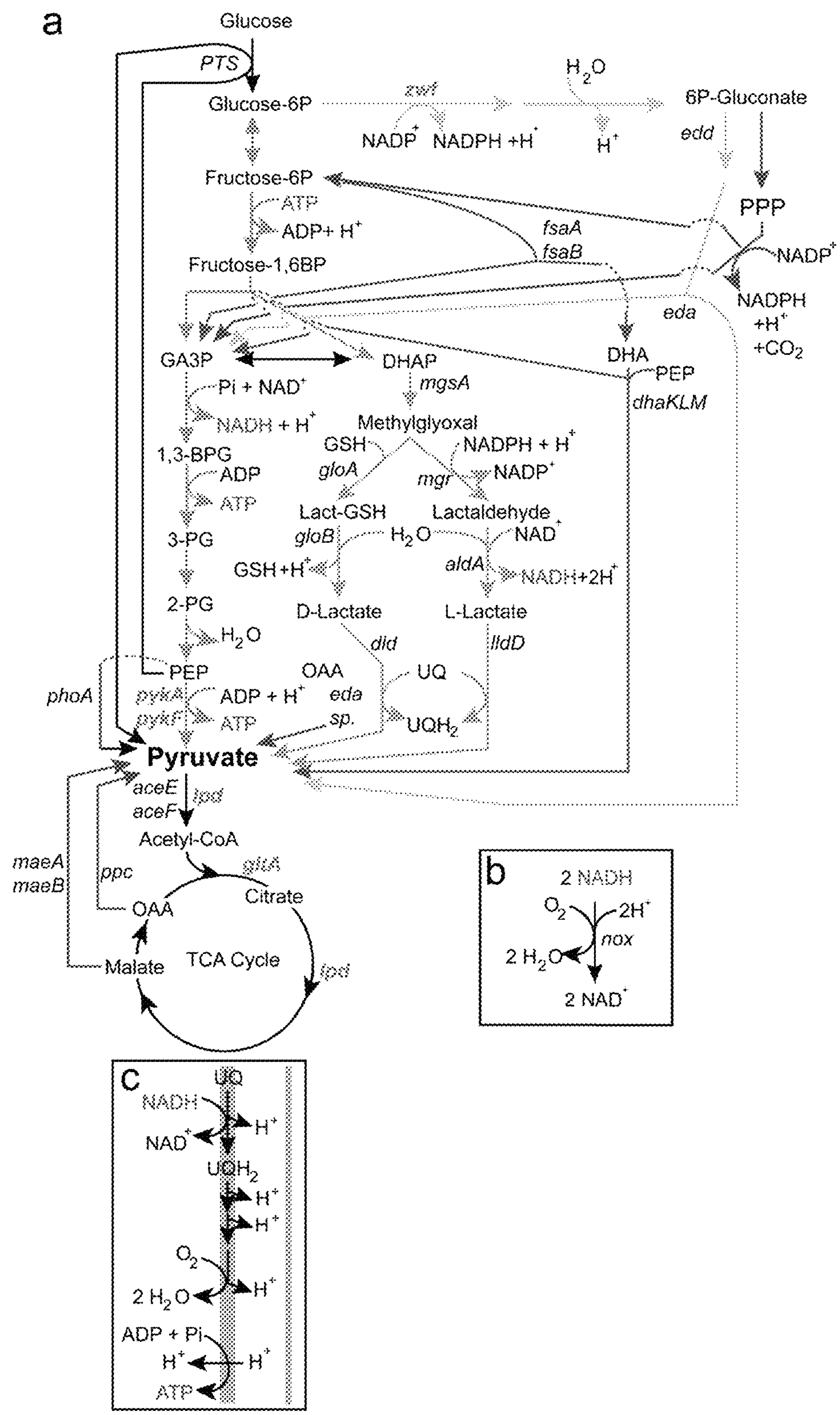
FIG. 1 depicts metabolic pathways involved in the production of pyruvate or pyruvic acid from glucose. The following abbreviations are found in the Figure: PTS—glucose phosphotransferase transport system, P—phosphate, BP—bisphosphate, OAA—oxaloacetate, DHAP—dihydroxyacetone phosphate, GA3P-glyceraldehyde-3-phosphate, 1,3-BPG—1,3 bisphosphoglycerate, 3-PG—3-phosphoglycerate, 2-PG—2-phosphoglycerate, PEP-phosphoenolpyruvate, PPP—pentose phosphate pathway, GSH—glutathione, Lact-lactaldehyde, UQ—oxidized ubiquinone, UQH2—reduced ubiquinone, TCA—tricarboxylic acid.

The present invention is related to various production methods and/or genetically modified microorganisms that have utility for production of pyruvate and or pyruvic acid as well as to related chemical products, to methods of making such chemical products that use populations of these microorganisms in vessels, and to systems for chemical production that employ these microorganisms and methods.

Definitions

As used in the specification and the claims, the singular forms "a," "an," and "the" include plural referents unless the context clearly dictates otherwise. Thus, for example, reference to an "expression vector" includes a single expression vector as well as a plurality of expression vectors, either the same (e.g., the same operon) or different; reference to "microorganism" includes a single microorganism as well as a plurality of microorganisms; and the like.

The term "heterologous DNA," "heterologous nucleic acid sequence," and the like as used herein refers to a nucleic acid sequence wherein at least one of the following is true: (a) the sequence of nucleic acids is foreign to (i.e., not naturally found in) a given host microorganism; (b) the sequence may be naturally found in a given host microorganism, but in an unnatural (e.g., greater than expected) amount; or (c) the sequence of nucleic acids comprises two or more subsequences that are not found in the same relationship to each other in nature. For example, regarding instance (c), a heterologous nucleic acid sequence that is recombinantly produced will have two or more sequences from unrelated genes arranged to make a new functional nucleic acid, such as an nonnative promoter driving gene expression.

The term "synthetic metabolic valve," and the like as used herein refers to either the use of controlled proteolysis, gene silencing or the combination of both proteolysis and gene silencing to alter metabolic fluxes.

The term "heterologous" is intended to include the term "exogenous" as the latter term is generally used in the art. With reference to the host microorganism's genome prior to the introduction of a heterologous nucleic acid sequence, the nucleic acid sequence that codes for the enzyme is heterologous (whether or not the heterologous nucleic acid sequence is introduced into that genome). As used herein, chromosomal and native and endogenous refer to genetic material of the host microorganism.

As used herein, the term "gene disruption," or grammatical equivalents thereof (and including "to disrupt enzymatic function," "disruption of enzymatic function," and the like), is intended to mean a genetic modification to a microorganism that renders the encoded gene product as having a reduced polypeptide activity compared with polypeptide activity in or from a microorganism cell not so modified. The genetic modification can be, for example, deletion of the entire gene, deletion or other modification of a regulatory sequence required for transcription or translation, deletion of a portion of the gene which results in a truncated gene product (e.g., enzyme) or by any of various mutation strategies that reduces activity (including to no detectable activity level) the encoded gene product. A disruption may broadly include a deletion of all or part of the nucleic acid sequence encoding the enzyme, and also includes, but is not limited to other types of genetic modifications, e.g., introduction of stop codons, frame shift mutations, introduction or removal of portions of the gene, and introduction of a degradation signal, those genetic modifications affecting mRNA transcription levels and/or stability, and altering the promoter or repressor upstream of the gene encoding the enzyme.

Bio-production, Micro-fermentation (microfermentation) or Fermentation, as used herein, may be aerobic, microaerobic, or anaerobic.

When the genetic modification of a gene product, i.e., an enzyme, is referred to herein, including the claims, it is understood that the genetic modification is of a nucleic acid sequence, such as or including the gene, that normally encodes the stated gene product, i.e., the enzyme.

As used herein, the term "metabolic flux" and the like refers to changes in metabolism that lead to changes in product and/or byproduct formation, including production rates, production titers and production yields from a given substrate.

Species and other phylogenic identifications are according to the classification known to a person skilled in the art of microbiology.

Enzymes are listed here within, with reference to a UniProt identification number, which would be well known to one skilled in the art. The UniProt database can be accessed at http://www.UniProt.org/. When the genetic modification of a gene product, i.e., an enzyme, is referred to herein, including the claims, it is understood that the genetic modification is of a nucleic acid sequence, such as or including the gene, that normally encodes the stated gene product, i.e., the enzyme.

Where methods and steps described herein indicate certain events occurring in certain order, those of ordinary skill in the art will recognize that the ordering of certain steps may be modified and that such modifications are in accordance with the variations of the invention. Additionally, certain steps may be performed concurrently in a parallel process when possible, as well as performed sequentially.

The meaning of abbreviations is as follows: "C" means Celsius or degrees Celsius, as is clear from its usage, DCW means dry cell weight, "s" means second(s), "min" means minute(s), "h," "hr," or "hrs" means hour(s), "psi" means pounds per square inch, "nm" means nanometers, "d" means day(s), "μL" or "uL" or "ul" means microliter(s), "mL" means milliliter(s), "L" means liter(s), "mm" means millimeter(s), "nm" means nanometers, "mM" means millimolar, "μM" or "uM" means micromolar, "M" means molar, "mmol" means millimole(s), "μmol" or "uMol" means micromole(s)", "g" means gram(s), "μg" or "ug" means microgram(s) and "ng" means nanogram(s), "PCR" means polymerase chain reaction, "OD" means optical density, "$OD_{600}$" means the optical density measured at a photon wavelength of 600 nm, "kDa" means kilodaltons, "g" means the gravitation constant, "bp" means base pair(s), "kbp" means kilobase pair(s), "% w/v" means weight/volume percent, "% v/v" means volume/volume percent, "IPTG" means isopropyl-μ-D-thiogalactopyranoiside, "aTc" means anhydrotetracycline, "RBS" means ribosome binding site, "rpm" means revolutions per minute, "HPLC" means high performance liquid chromatography, and "GC" means gas chromatography.

I. Carbon Sources

Bio-production media, which is used in the present invention with recombinant microorganisms must contain suitable carbon sources or substrates for both growth and production stages. Suitable substrates may include, but are not limited to glucose, sucrose, xylose, mannose, arabinose, oils, carbon dioxide, carbon monoxide, methane, methanol, formaldehyde and glycerol. It is contemplated that all of the above mentioned carbon substrates and mixtures thereof are suitable in the present invention as a carbon source(s).

II. Microorganisms

Features as described and claimed herein may be provided in a microorganism selected from the listing herein, or another suitable microorganism, that also comprises one or more natural, introduced, or enhanced product bio-production pathways. Thus, in some embodiments the microorganism(s) comprise an endogenous product production pathway (which may, in some such embodiments, be enhanced), whereas in other embodiments the microorganism does not comprise an endogenous product production pathway.

More particularly, based on the various criteria described herein, suitable microbial hosts for the bio-production of a chemical product generally may include, but are not limited to the organisms described in the Common Methods Section.

III. Media and Culture Conditions

In addition to an appropriate carbon source, such as selected from one of the herein-disclosed types, bio-production media must contain suitable minerals, salts, cofactors, buffers and other components, known to those skilled in the art, suitable for the growth of the cultures and promotion of chemical product bio-production under the present invention.

Another aspect of the invention regards media and culture conditions that comprise genetically modified microorganisms of the invention and optionally supplements.

Typically cells are grown at a temperature in the range of about 25° C. to about 40° C. in an appropriate medium, as well as up to 70° C. for thermophilic microorganisms. Suitable growth media are well characterized and known in the art. Suitable pH ranges for the bio-production are between pH 2.0 to pH 10.0, where pH 6.0 to pH 8.0 is a typical pH range for the initial condition. However, the actual culture conditions for a particular embodiment are not meant to be limited by these pH ranges. Bio-productions may be performed under aerobic, microaerobic or anaerobic conditions with or without agitation.

IV. Bio-Production Reactors and Systems

Fermentation systems utilizing methods and/or compositions according to the invention are also within the scope of the invention. Any of the recombinant microorganisms as described and/or referred to herein may be introduced into an industrial bio-production system where the microorganisms convert a carbon source into a product in a commercially viable operation. The bio-production system includes the introduction of such a recombinant microorganism into a bioreactor vessel, with a carbon source substrate and bio-production media suitable for growing the recombinant microorganism, and maintaining the bio-production system within a suitable temperature range (and dissolved oxygen concentration range if the reaction is aerobic or microaerobic) for a suitable time to obtain a desired conversion of a portion of the substrate molecules to a selected chemical product. Bio-productions may be performed under aerobic, microaerobic, or anaerobic conditions, with or without agitation. Industrial bio-production systems and their operation are well-known to those skilled in the arts of chemical engineering and bioprocess engineering.

The amount of a product produced in a bio-production media generally can be determined using a number of methods known in the art, for example, high performance liquid chromatography (HPLC), gas chromatography (GC), or GC/Mass Spectroscopy (MS).

V. Genetic Modifications, Nucleotide Sequences, and Amino Acid Sequences

Embodiments of the present invention may result from introduction of an expression vector into a host microorganism, wherein the expression vector contains a nucleic acid sequence coding for an enzyme that is, or is not, normally found in a host microorganism.

The ability to genetically modify a host cell is essential for the production of any genetically modified (recombinant) microorganism. The mode of gene transfer technology may be by electroporation, conjugation, transduction, or natural transformation. A broad range of host conjugative plasmids and drug resistance markers are available. The cloning vectors are tailored to the host organisms based on the nature of antibiotic resistance markers that can function in that host. Also, as disclosed herein, a genetically modified (recombinant) microorganism may comprise modifications other than via plasmid introduction, including modifications to its genomic DNA.

More generally, nucleic acid constructs can be prepared comprising an isolated polynucleotide encoding a polypeptide having enzyme activity operably linked to one or more (several) control sequences that direct the expression of the coding sequence in a microorganism, such as *E. coli*, under conditions compatible with the control sequences. The isolated polynucleotide may be manipulated to provide for expression of the polypeptide. Manipulation of the polynucleotide's sequence prior to its insertion into a vector may be desirable or necessary depending on the expression vector. The techniques for modifying polynucleotide sequences utilizing recombinant DNA methods are well established in the art.

The control sequence may be an appropriate promoter sequence, a nucleotide sequence that is recognized by a host cell for expression of a polynucleotide encoding a polypeptide of the present invention. The promoter sequence may contain transcriptional control sequences that mediate the expression of the polypeptide. The promoter may be any nucleotide sequence that shows transcriptional activity in the host cell of choice including mutant, truncated, and hybrid promoters, and may be obtained from genes encoding extracellular or intracellular polypeptides either homologous or heterologous to the host cell. The techniques for modifying and utilizing recombinant DNA promoter sequences are well established in the art.

For various embodiments of the invention the genetic manipulations may include a manipulation directed to change regulation of, and therefore ultimate activity of, an enzyme or enzymatic activity of an enzyme identified in any of the respective pathways. Such genetic modifications may be directed to transcriptional, translational, and post-translational modifications that result in a change of enzyme activity and/or selectivity under selected culture conditions. Genetic manipulation of nucleic acid sequences may increase copy number and/or comprise use of mutants of an enzyme related to product production. Specific methodologies and approaches to achieve such genetic modification are well known to one skilled in the art.

In various embodiments, to function more efficiently, a microorganism may comprise one or more gene deletions. For example, in *E. coli*, the genes encoding the lactate dehydrogenase (ldhA), phosphate acetyltransferase (pta), pyruvate oxidase (poxB), pyruvate-formate lyase (pflB), methylglyoxal synthase (mgsA), acetate kinase (ackA), alcohol dehydrogenase (adhE), the clpXP protease specificity enhancing factor (sspB), the ATP-dependent Lon protease (lon), the outer membrane protease (ompT), the arcA transcriptional dual regulator (arcA), and the iclR transcriptional regulator (iclR) may be disrupted, including deleted. Such gene disruptions, including deletions, are not meant to be limiting, and may be implemented in various combinations in various embodiments. Gene deletions may be accomplished by numerous strategies well known in the art, as are methods to incorporate foreign DNA into a host chromosome.

In various embodiments, to function more efficiently, a microorganism may comprise one or more synthetic metabolic valves, composed of enzymes targeted for controlled proteolysis, expression silencing or a combination of both controlled proteolysis and expression silencing. For example, one enzyme encoded by one gene or a combination of numerous enzymes encoded by numerous genes in *E. coli* may be designed as synthetic metabolic valves to alter metabolism and improve product formation. Representative genes in *E. coli* may include but are not limited to the following: fabI, zwf, gltA, ppc, udhA, lpd, sucD, aceA, pfkA, ion, rpoS, pykA, pykF, tktA or tktB. It is appreciated that it is well known to one skilled in the art how to identify homologues of these genes and or other genes in additional microbial species.

For all nucleic acid and amino acid sequences provided herein, it is appreciated that conservatively modified variants of these sequences are included, and are within the scope of the invention in its various embodiments. Functionally equivalent nucleic acid and amino acid sequences (functional variants), which may include conservatively modified variants as well as more extensively varied sequences, which are well within the skill of the person of ordinary skill in the art, and microorganisms comprising these, also are within the scope of various embodiments of the invention, as are methods and systems comprising such sequences and/or microorganisms.

Accordingly, as described in various sections above, some compositions, methods and systems of the present invention comprise providing a genetically modified microorganism that comprises both a production pathway to make a desired product from a central intermediate in combination with synthetic metabolic valves to redistribute flux.

Aspects of the invention also regard provision of multiple genetic modifications to improve microorganism overall effectiveness in converting a selected carbon source into a selected product. Particular combinations are shown, such as in the Examples, to increase specific productivity, volumetric productivity, titer and yield substantially over more basic combinations of genetic modifications.

In addition to the above-described genetic modifications, in various embodiments genetic modifications, including synthetic metabolic valves also are provided to increase the pool and availability of the cofactor NADPH and/or NADH which may be consumed in the production of a product.

More generally, and depending on the particular metabolic pathways of a microorganism selected for genetic modification, any subgroup of genetic modifications may be made to decrease cellular production of fermentation product(s) other than the desired fermentation product, selected from the group consisting of acetate, acetoin, acetone, acrylic, malate, fatty acid ethyl esters, isoprenoids, glycerol, ethylene glycol, ethylene, propylene, butylene, isobutylene, ethyl acetate, vinyl acetate, other acetates, 1,4-butanediol, 2,3-butanediol, butanol, isobutanol, sec-butanol, butyrate, isobutyrate, 2-OH-isobutryate, 3-OH-butyrate, ethanol, isopropanol, D-lactate, L-lactate, pyruvate, itaconate, levulinate, glucarate, glutarate, caprolactam, adipic acid, propanol, isopropanol, fusel alcohols, and 1,2-propanediol, 1,3-propanediol, formate, fumaric acid, propionic acid, succinic acid, valeric acid, maleic acid and poly-hydroxybutyrate. Gene deletions may be made as disclosed generally herein, and other approaches may also be used to achieve a desired decreased cellular production of selected fermentation products other than the desired products.

VI. Synthetic Metabolic Valves

Use of synthetic metabolic valves allows for simpler models of metabolic fluxes and physiological demands during a production phase, turning a growing cell into a stationary phase biocatalyst. These synthetic metabolic valves can be used to turn off essential genes and redirect carbon, electrons and energy flux to product formation in a multi-stage fermentation process. One or more of the following provides the described synthetic valves: 1) transcriptional gene silencing or repression technologies in combination with 2) inducible and selective enzyme degradation and 3) nutrient limitation to induce a stationary or non-dividing cellular state. SMVs are generalizable to any pathway and microbial host. These synthetic metabolic valves allow for novel rapid metabolic engineering strategies useful for the production of renewable chemicals and fuels and any product that can be produced via whole cell catalysis.

In particular, the invention describes the construction of synthetic metabolic valves comprising one or more or a combination of the following: controlled gene silencing and controlled proteolysis. It is appreciated that one well skilled in the art is aware of several methodologies for gene silencing and controlled proteolysis.

VI.A Gene Silencing

In particular, the invention describes the use of controlled gene silencing to provide the control over metabolic fluxes in controlled multi-stage fermentation processes. There are several methodologies known in the art for controlled gene silencing, including but not limited to mRNA silencing or RNA interference, silencing via transcriptional repressors and CRISPR interference. Methodologies and mechanisms for RNA interference are taught by Agrawal et al. "RNA Interference: Biology, Mechanism, and Applications" Microbiology and Molecular Biology Reviews, December 2003; 67(4) p 657-685. DOI: 10.1128/MMBR.67.657-685.2003. Methodologies and mechanisms for CRISRPR interference are taught by Qi et al. "Repurposing CRISPR as an RNA-guided platform for sequence-specific control of gene expression" Cell February 2013; 152(5) p 1173-1183. DOI: 10.1016/j.cell.2013.02.022. In addition, methodologies and mechanisms for CRISRPR interference using the native *E. coli* CASCADE system are taught by Luo et al. "Repurposing endogenous type I CRISPR-Cas systems for programmable gene repression" NAR. October 2014; DOI: 10.1093. In additional numerous transcriptional repressor systems are well known in the art and can be used to turn off gene expression.

VI.B Controlled Proteolysis

In particular, the invention describes the use of controlled protein degradation or proteolysis to provide the control over metabolic fluxes in controlled multi-stage fermentation processes. There are several methodologies known in the art for controlled protein degradation, including but not limited to targeted protein cleavage by a specific protease and controlled targeting of proteins for degradation by specific peptide tags. Systems for the use of the *E. coli* clpXP protease for controlled protein degradation are taught by McGinness et al, "Engineering controllable protein degradation", Mol Cell. June 2006; 22(5) p 701-707. This methodology relies upon adding a specific C-terminal peptide tag such as a DAS4 (or DAS+4) tag. Proteins with this tag are not degraded by the clpXP protease until the specificity enhancing chaperone sspB is expressed. sspB induces degradation of DAS4 tagged proteins by the clpXP protease. In additional numerous site specific protease systems are well known in the art. Proteins can be engineered to contain a specific target site of a given protease and then cleaved after the controlled expression of the protease. In some embodiments, the cleavage can be expected lead to protein inactivation or degradation. For example Schmidt et al ("ClpS is the recognition component for *Escherichia coli* substrates of the N-end rule degradation pathway" Molecular Microbiology March 2009. 72(2), 506-517. doi:10.1111), teaches that an N-terminal sequence can be added to a protein of interest in providing clpS dependent clpAP degradation. In addition, this sequence can further be masked by an additional N-terminal sequence, which can be controllable cleaved such as by a ULP hydrolase. This allows for controlled N-rule degradation dependent on hydrolase expression. It is therefore possible to tag proteins for controlled proteolysis either at the N-terminus or C-terminus. The preference of using an N-terminal vs. C-terminal tag will largely depend on whether either tag affects protein function prior to the controlled onset of degradation.

The invention describes the use of controlled protein degradation or proteolysis to provide the control over metabolic fluxes in controlled multi-stage fermentation processes, in *E. coli*. There are several methodologies known in the art for controlled protein degradation in other microbial hosts, including a wide range of gram-negative as well as gram-positive bacteria, yeast and even archaea. In particular, systems for controlled proteolysis can be transferred from a native microbial host and used in a non-native host. For example Grilly et al, "A synthetic gene network for tuning protein degradation in *Saccharomyces cerevisiae*" Molecular Systems Biology 3, Article 127. doi:10.1038, teaches the expression and use of the *E. coli* clpXP protease in the yeast *Saccharomyces cerevisiae*. Such approaches can be used to transfer the methodology for synthetic metabolic valves to any genetically tractable host.

VI.C Synthetic Metabolic Valve Control

In particular the invention describes the use of synthetic metabolic valves to control metabolic fluxes in multi-stage fermentation processes. There are numerous methodologies known in the art to induce expression that can be used at the transition between stages in multi-stage fermentations. These include but are not limited to artificial chemical inducers including: tetracycline, anhydrotetracycline, lactose, IPTG (isopropyl-beta-D-1-thiogalactopyranoside), arabinose, raffinose, tryptophan and numerous others. Systems linking the use of these well known inducers to the control of gene expression silencing and/or controlled proteolysis can be integrated into genetically modified microbial systems to control the transition between growth and production phases in multi-stage fermentation processes.

In addition, it may be desirable to control the transition between growth and production in multi-stage fermentations by the depletion of one or more limiting nutrients that are consumed during growth. Limiting nutrients can include but are not limited to: phosphate, nitrogen, sulfur and magnesium. Natural gene expression systems that respond to these nutrient limitations can be used to operably link the control of gene expression silencing and/or controlled proteolysis to the transition between growth and production phases in multi-stage fermentation processes.

VII. Pyruvate and Product Producing Strains

Referring now to FIG. 1: Enzymes/genes that are candidates to either "turned off" with metabolic valves or deleted as potentially overexpressed are shown: glucose-6-phosphate dehydrogenase (zwf-"Z"), lipoamide dehydrogenase (lpd-"L"), citrate synthase (gltA-"G"), pyruvate dehydrogenase complex subunit (aceEF, lpd-"L"), pyruvate kinase A (pykA-"A"), pyruvate kinase F (pykF-"F"), nox, methylglyoxal synthase (mgsA), multisubunit dihydroxyacetone kinase (dhaKLM), methylglyoxal reductase (mgr), aldehyde dehydrogenase (aldA), phosphoenolpyruvate carboxylase (ppc), phosphatase (phoA), malate dehydrogenase—NAD+ specific (maeA), malate dehydrogenase (maeB), glyoxylase I (gloA), glyoxylase II (gloB), phosphogluconate dehydratase (edd), multifunctional 2-keto-3-deoxygluconate 6-phosphate aldolase and 2-keto-4-hydroxyglutarate aldolase and oxaloacetate decarboxylase (eda), fructose-6-phosphate aldolase I (fsaA), fructose-6-phosphate aldolase II (fsaB), D-lactate dehydrogenase (dld), L-lactate dehydrogenase (lld).

In certain embodiments pyruvate production is greatly enhanced in strains engineered to reduce or eliminate flux through biochemical steps in pathways known to be responsible for pyruvate biosynthesis as illustrated in FIG. 1. In various embodiments, this can either be accomplished by gene deletions, in the case of non essential genes, or through the use of dynamic metabolic valves, as described above when a gene is essential and/or important for growth. In certain embodiments valves alone and or in the combination in the following genes can lead to enhanced pyruvate production: glucose-6-phosphate dehydrogenase (zwf-"Z"), lipoamide dehydrogenase (lpd-"L"), citrate synthase (ghA-"G"), pyruvate dehydrogenase complex subunit (aceEF, lpd-"L"), pyruvate kinase A (pykA-"A"), pyruvate kinase F (pykF-"F"), methylglyoxal synthase (mgsA), multisubunit dihydroxyacetone kinase (dhaKLM), methylglyoxal reductase (mgr), aldehyde dehydrogenase (aldA), phosphoenolpyruvate carboxylase (ppc), phosphatase (phoA), malate dehydrogenase—NAD+ specific (maeA), malate dehydrogenase (maeB), glyoxylase I (gloA), glyoxylase II (gloB), phosphogluconate dehydratase (edd), multifunctional 2-keto-3-deoxygluconate 6-phosphate aldolase and 2-keto-4-hydroxyglutarate aldolase and oxaloacetate decarboxylase (eda), fructose-6-phosphate aldolase I (fsaA), fructose-6-phosphate aldolase II (fsaB), D-lactate dehydrogenase (dld), L-lactate dehydrogenase (lld) or erythrose-4-phosphate dehydrogenase (epd). Pyruvate is then presumably synthesized through one or more uncharacterized routes or through rerouting flux through one or more alternative known pyruvate synthesis pathways. In additional embodiments, deletions of many of these potential alternative pathways alone and in combination does not eliminate pyruvate synthesis. In other embodiments, additionally overexpression an NADH oxidase enzyme capable of removing excess NADH formed as a byproduct of pyruvate synthesis can enhance pyruvate production. In still other embodiments strains engineered with one or more of the genetic modification discussed above can be grown in large scale fermentations enabling pyruvate production at high rates, titers and yields. Yet in still additional embodiments, biochemical pathways well known in the art capable of converting pyruvate into additional numerous chemicals can be incorporated into the above described strains to convert pyruvate into additional products.

The microbial strains are engineered for pyruvate product production. Pyruvate product refers to pyruvate, pyruvic acid, or any other form of pyruvate. However, the strains are also able to produce a variety of pyruvate derived products. The microorganisms may also comprise a pyruvate derived product production pathway or alternatively, the pyruvate product produced by the microorganism may be a source for pyruvate derived product production. In some cases, the pyruvate derived product is produced from pyruvate by an enzymatic pathway. The enzymatic pathway may comprise one or more than one enzymatic action. The pyruvate derived product production may also occur by chemical action on pyruvate.

Some exemplary pyruvate derived products include: an amino acid, alanine, valine, isoleucine, leucine, serine, cysteine, aspartate, acetylaldehyde, phosphoenolypyruvate, citrate, oxaloacetate, ethyl pyruvate, L-DOPA, N-acetyl-D-neuraminic acid, (R)-phenylacetylcarbinol, acetate, acetoin, acetone, acrylic, malate, fatty acid ethyl esters, acetylCoA, isoprenoids, glycerol, ethylene glycol, ethylene, propylene, butylene, isobutylene, ethyl acetate, vinyl acetate, 1,4-butanediol, 2,3-butanediol, butanol, isobutanol, sec-butanol, butyrate, isobutyrate, 2-OH-isobutryate, 3-OH-butyrate, ethanol, isopropanol, D-lactate, L-lactate, pyruvate, itaconate, levulinate, glucarate, glutarate, caprolactam, adipic acid, propanol, isopropanol, fusel alcohols, and 1,2-propanediol, 1,3-propanediol, formate, fumaric acid, propionic acid, succinic acid, valeric acid, maleic acid and poly-hydroxybutyrate. Of course, the microorgansims and methods described herein provide a source of pyruvate available for production of any product formed from pyruvate.

Within the scope of the invention are genetically modified microorganism, wherein the microorganism is capable of producing pyruvate or a pyruvate derived product at a specific rate selected from the rates of greater than 0.05 g/gDCW-hr, 0.08 g/gDCW-hr, greater than 0.1 g/gDCW-hr, greater than 0.13 g/gDCW-hr, greater than 0.15 g/gDCW-hr, greater than 0.175 g/gDCW-hr, greater than 0.2 g/gDCW-hr, greater than 0.25 g/gDCW-hr, greater than 0.3 g/gDCW-hr, greater than 0.35 g/gDCW-hr, greater than 0.4 g/gDCW-hr, greater than 0.45 g/gDCW-hr, or greater than 0.5 g/gDCW-hr.

Within the scope of the invention are genetically modified microorganism, wherein the microorganism is capable of producing a pyruvate product or a pyruvate derived product from a hexose sugar source at a yield greater than 0.5 g product/g hexose, greater than 0.6 g product/g hexose, greater than 0.7 g product/g hexose, greater than 0.8 g product/g hexose, greater than 0.9 g product/g hexose, greater than 0.95 g product/g hexose, or greater than 0.98 g product/g hexose.

In various embodiments, the invention includes a culture system comprising a carbon source in an aqueous medium and a genetically modified microorganism according to any one of claims herein, wherein said genetically modified organism is present in an amount selected from greater than 0.05 gDCW/L, 0.1 gDCW/L, greater than 1 gDCW/L, greater than 5 gDCW/L, greater than 10 gDCW/L, greater than 15 gDCW/L or greater than 20 gDCW/L, such as when the volume of the aqueous medium is selected from greater than 5 mL, greater than 100 mL, greater than 0.5 L, greater than 1 L, greater than 2 L, greater than 10 L, greater than 250 L, greater than 1000 L, greater than 10,000 L, greater than 50,000 L, greater than 100,000 L or greater than 200,000 L, and such as when the volume of the aqueous medium is greater than 250 L and contained within a steel vessel.

SUMMARY

Herein described is a genetically modified microorganism and biofermentation methods for producing a pyruvate product comprising use of a genetically modified microorganism having a combination of at least one of three types of modifications: a synthetic metabolic valve characterized by silencing gene expression of one or more genes encoding one or more enzymes; a synthetic metabolic valve characterized by inducing enzymatic degradation of one or more enzymes; and a chromosomal deletion of a gene encoding an enzyme of a pyruvate metabolism pathway.

A gene expression-silencing synthetic metabolic valve refers to a synthetic metabolic valve that is at least characterized by silencing gene expression of one or more genes encoding one or more enzymes. An enzymatic degradation synthetic metabolic valve refers to a synthetic metabolic valve characterized by at least inducing enzymatic degradation of one or more enzymes. In cases where there are more than one enzymes controlled by the gene silencing valve and the enzymatic valve, the gene groups of each valve may be the exactly the same, have some gene in common and some genes that are different or the two valves may regulate groups of genes with no overlap.

The gene expression-silencing synthetic metabolic valve and the enzymatic degradation synthetic metabolic valve are activated under conditions that are suitable for causing a transition in a biofermentation process. Such as chemical induction or nutrient depletion.

The one or more enzymes of each synthetic metabolic valve are the same or different. That is, the enzyme selection for silencing and enzymatic degradation may be the same enzyme or two enzymes may be subject to control by the synthetic metabolic valves of the microorganism.

The genetically modified microorganism may have a single modification or combination of modifications. For example, multiple metabolic valves directed to multiple enzymes may be used. A combination of two of the three modifications may be used, for example, a gene deletion combined with enzymatic degradation of one or more enzymes. In some cases a single valve may control expression of more than one enzyme simultaneously.

The genetically modified microorganism characterized by an increased production of pyruvate in a biofermentation process as compared to pyruvate produced from biofermentation of a non-genetically modified microorganism.

The genetically modified microorganism may be characterized in that the one or more enzymes are selected from the group consisting of: fabI, zwf, gltA, ppc, udhA, lpd, sucD, aceA, pfkA, ion, rpoS, pykA, pykF, tktA or tktB. The one or more enzymes is selected from the group consisting of:

citrate synthase (gltA), pyruvate dehydrogenase (lpd), and glucose-6-phosphate dehydrogenase (zwf). The one or more enzymes may be a pyruvate kinase. The one or more enzymes is a pyruvate kinase A (pykA) or pyruvate kinase F (pykF).

The chromosomal deletion of the genetically modified microorganism may be selected from the group consisting of: methylglyoxal synthase (mgsA), dihydroxyacetone kinase (dhaL), D-erythrose-4-phosphate dehydrogenase (epd), 2-keto-3-deoxygluconate 6-phosphate/2-keto-4-hydroxyglutarate aldolase (eda), and PTS multiphosphoryl transfer protein (ptsA).

In some cases, the genetically modified microorganism also expresses, or overexpresses a NADH oxidase.

Silencing of gene expression may occur via CRISPR interference and the genetically modified microorganism may also express a CASCADE guide array, the array comprising two or more genes encoding small guide RNAs each specific for targeting a different gene for simultaneous silencing of multiple genes.

In some cases, the genetically modified microorganism produces a pyruvate product titer of greater than 0.08 g/L at twenty four in a biofermentation process.

The genetically modified microorganism may also include a production pathway for producing a pyruvate derived product. That is, the genetically modified microorganism may express an enzyme for conversion of pyruvate to a derived product, such as an amino acid. This conversion of pyruvate to a pyruvate derived product may occur in one step or in multiple steps. The conversion may occur within the microorganism itself or within a reactor vessel containing the microorganism. The pyruvate derived product may be selected from the group consisting of: an amino acid, alanine, valine, isoleucine, leucine, serine, cysteine, aspartate, acetylaldehyde, phosphoenolypyruvate, citrate, oxaloacetate, ethyl pyruvate, L-DOPA, N-acetyl-D-neuraminic acid, (R)-phenylacetylcarbinol, acetate, acetoin, acetone, acrylic, malate, fatty acid ethyl esters, acetylCoA, isoprenoids, glycerol, ethylene glycol, ethylene, propylene, butylene, isobutylene, ethyl acetate, vinyl acetate, 1,4-butanediol, 2,3-butanediol, butanol, isobutanol, sec-butanol, butyrate, isobutyrate, 2-OH-isobutryate, 3-OH-butyrate, ethanol, isopropanol, D-lactate, L-lactate, pyruvate, itaconate, levulinate, glucarate, glutarate, caprolactam, adipic acid, propanol, isopropanol, fusel alcohols, and 1,2-propanediol, 1,3-propanediol, formate, fumaric acid, propionic acid, succinic acid, valeric acid, maleic acid and poly-hydroxybutyrate.

Exemplary methods for producing a pyruvate product from a genetically modified microorganism may comprise (a) in a first stage, growing a genetically modified microorganism, the genetically modified microorganism comprising a combination of at least one of: i. a synthetic metabolic valve characterized by silencing gene expression of one or more genes encoding one or more enzymes; ii. a synthetic metabolic valve characterized by inducing enzymatic degradation of one or more enzymes; and iii. a chromosomal deletion, wherein the one or more enzymes of each synthetic metabolic valve are the same or different. A second stage of the method may include: (i) inducing the synthetic metabolic valve(s) to slow or stop the growth of the microorganism and to change metabolism within the microorganism; and (ii) producing a pyruvate product.

The method may further include a step of (c) centrifugation to separate the genetically modified microorganism and the pyruvate product. The method may include a further step of formation of a pyruvate salt from the pyruvate product or formation of a pyruvate ester from the pyruvate product. The method may include a further step of producing a pyruvate derived product by biochemical conversion of the pyruvate product to a derived product selected from the group consisting of: an amino acid, alanine, valine, isoleucine, leucine, serine, cysteine, aspartate, acetylaldehyde, phosphoenolypyruvate, citrate, oxaloacetate, ethyl pyruvate, L-DOPA, N-acetyl-D-neuraminic acid, (R)-phenylacetylcarbinol, acetate, acetoin, acetone, acrylic, malate, fatty acid ethyl esters, acetylCoA, isoprenoids, glycerol, ethylene glycol, ethylene, propylene, butylene, isobutylene, ethyl acetate, vinyl acetate, 1,4-butanediol, 2,3-butanediol, butanol, isobutanol, sec-butanol, butyrate, isobutyrate, 2-OH-isobutryate, 3-OH-butyrate, ethanol, isopropanol, D-lactate, L-lactate, pyruvate, itaconate, levulinate, glucarate, glutarate, caprolactam, adipic acid, propanol, isopropanol, fusel alcohols, and 1,2-propanediol, 1,3-propanediol, formate, fumaric acid, propionic acid, succinic acid, valeric acid, maleic acid and poly-hydroxybutyrate.

Disclosed Embodiments are Non-Limiting

While various embodiments of the present invention have been shown and described herein, it is emphasized that such embodiments are provided by way of example only. Numerous variations, changes and substitutions may be made without departing from the invention herein in its various embodiments. Specifically, and for whatever reason, for any grouping of compounds, nucleic acid sequences, polypeptides including specific proteins including functional enzymes, metabolic pathway enzymes or intermediates, elements, or other compositions, or concentrations stated or otherwise presented herein in a list, table, or other grouping (such as metabolic pathway enzymes shown in a FIG. 1), unless clearly stated otherwise, it is intended that each such grouping provides the basis for and serves to identify various subset embodiments, the subset embodiments in their broadest scope comprising every subset of such grouping by exclusion of one or more members (or subsets) of the respective stated grouping. Moreover, when any range is described herein, unless clearly stated otherwise, that range includes all values therein and all sub-ranges therein.

Also, and more generally, in accordance with disclosures, discussions, examples and embodiments herein, there may be employed conventional molecular biology, cellular biology, microbiology, and recombinant DNA techniques within the skill of the art. Such techniques are explained fully in the literature. See, e.g., Sambrook and Russell, "Molecular Cloning: A Laboratory Manual," Third Edition 2001 (volumes 1-3), Cold Spring Harbor Laboratory Press, Cold Spring Harbor, N.Y.; Animal Cell Culture, R. I. Freshney, ed., 1986. These published resources are incorporated by reference herein.

The following published resources are incorporated by reference herein for description useful in conjunction with the invention described herein, for example, methods of industrial bio-production of chemical product(s) from sugar sources, and also industrial systems that may be used to achieve such conversion (Biochemical Engineering Fundamentals, $2^{nd}$ Ed. J. E. Bailey and D. F. 011 is, McGraw Hill, New York, 1986, e.g. Chapter 9, pages 533-657 for biological reactor design; Unit Operations of Chemical Engineering, $5^{th}$ Ed., W. L. McCabe et al., McGraw Hill, New York 1993, e.g., for process and separation technologies analyses; Equilibrium Staged Separations, P. C. Wankat, Prentice Hall, Englewood Cliffs, N.J. USA, 1988, e.g., for separation technologies teachings).

All publications, patents, and patent applications mentioned in this specification are entirely incorporated by reference herein, including U.S. Provisional Application Nos. 62/010,574, filed Jun. 11, 2014, and 62/461,436, filed Feb. 21, 2017, and PCT/US2015/035306 filed Jun. 11, 2015 and PCT/US2018/019040, filed February 21.

EXAMPLES

The examples herein provide some examples, not meant to be limiting. All reagents, unless otherwise indicated, are obtained commercially. Species and other phylogenic identifications are according to the classification known to a person skilled in the art of microbiology, molecular biology and biochemistry.

Example 1: Production of Pyruvate in Microfermentations Using *E. coli* Engineered with Metabolic Valves This example describes the increased production of pyruvate in *E. coli* using metabolic valves of several genes alone and in combination including pykA (encoding pyruvate kinase A), pykF (encoding pyruvate kinase B), gltA (encoding citrate synthase), zwf (encoding glucose-6-phosphate dehydrogenase), lpd (encoding a subunit of the pyruvate dehydrogenase multi-enzyme complex. Briefly, *E. coli* strain DLF 0025 (F−, $\lambda^-$, Δ(araD-araB)567, ΔlacZ4787(:rrnB-3), rph-1, Δ(rhaD-rhaB)568, hsdR514, ΔldhA::frt, ΔpoxB::frt, ΔpflB::frt, ΔackA-pta::frt, ΔadhE::frt, ΔiclR, ΔarcA, ΔsspB, Δcas3::ugpBp-sspB-proB) which is capable of dynamic metabolic control was further genetically modified to contain DAS+4 tags at the C-terminus of various enzymes as well as gene deletions. These strains were then transformed with pCASCADE plasmids expressing gRNA arrays capable of the silencing of several gene promoters, as well as optionally a plasmid allowing for the induction of NADH oxidase encoded by the nox gene which is under the control of the ugpB gene promoter and induced by phosphate depletion (Addgene Plasmid #1010894). The strains and plasmids were constructed as described in the common methods section. Following strain construction, strains were evaluated in standard microfermentations in microtiter plates in triplicate. Cells were harvested by centrifugation and pyruvate quantified in the supernatant by UPLC (Refer to Common methods Section). Results are given in Table 1 below as a function of strain, both with measured titers and biomass normalized titers.

TABLE 1

Pyruvate Production in MicroFermentations by engineered strains of *E. coli*.

| Strain # | Genes with Proteolysis Tags | Chromosomal Gene Deletions | Gene Silencing | NADH Oxidase Expression Vector | 24 hour Pryuvate Titer (g/L) | 24 Hour Normalized Pyruvate Titer (g/L- |
|---|---|---|---|---|---|---|
| 1 | gltA | None | pCASCADE-empty vector | None | 6.926334 | 3.103196 |
| 2 | gltA | None | pCASCADE-gltA1 | None | 2.435827 | 0.661909 |
| 3 | gltA | None | pCASCADE-gltA1-gltA2 | None | 1.644148 | 7.339948 |
| 4 | gltA | None | pCASCADE-gltA1-gltA2-pykA-pykF | None | 5.958417 | 3.252411 |
| 5 | gltA | None | pCASCADE-gltA1-gltA2-zwf | None | 2.087338 | 0.483628 |
| 6 | gltA | None | pCASCADE-gltA1-gltA2-zwf-pykA-pykF | None | 2.117973 | 3.601994 |
| 7 | gltA | None | pCASCADE-gltA1-pykA-pykF | None | 7.562506 | 3.322718 |
| 8 | gltA | None | pCASCADE-gltA1-zwf | None | 2.744115 | 2.858453 |
| 9 | gltA | None | pCASCADE-gltA1-zwf-pykA-pykF | None | 1.982524 | 0.496624 |
| 10 | gltA | None | pCASCADE-gltA2 | None | 1.839331 | 3.308149 |
| 11 | gltA | None | pCASCADE-gltA2-pykA-pykF | None | 3.377558 | 3.68729 |
| 12 | gltA | None | pCASCADE-gltA2-zwf | None | 1.862437 | 0.972044 |
| 13 | gltA | None | pCASCADE-gltA2-zwf-pykA-pykF | None | 2.173982 | 0.697683 |
| 14 | gltA | None | pCASCADE-pykA-pykF | None | 2.808667 | 0.794306 |
| 15 | gltA | None | pCASCADE-zwf | None | 7.906433 | 2.256402 |
| 16 | gltA | None | pCASCADE-zwf-pykA-pykF | None | 1.806812 | 0.460921 |
| 17 | gltA, pykA, pykF | None | pCASCADE-empty vector | None | 6.692441 | 4.61519 |
| 18 | gltA, pykA, pykF | None | pCASCADE-gltA1 | None | 2.033619 | 1.570556 |
| 19 | gltA, pykA, pykF | None | pCASCADE-gltA1-gltA2 | None | 1.03772 | 2.753742 |
| 20 | gltA, pykA, pykF | None | pCASCADE-gltA1-gltA2-pykA-pykF | None | 1.081247 | 2.936575 |
| 21 | gltA, pykA, pykF | None | pCASCADE-gltA1-gltA2-zwf | None | 1.409172 | 1.184098 |
| 22 | gltA, pykA, pykF | None | pCASCADE-gltA1-gltA2-zwf-pykA-pykF | None | 1.792465 | 2.4126 |
| 23 | gltA, pykA, pykF | None | pCASCADE-gltA1-pykA-pykF | None | 2.253633 | 2.611062 |
| 24 | gltA, pykA, pykF | None | pCASCADE-gltA1-zwf | None | 2.113928 | 2.554688 |
| 25 | gltA, pykA, pykF | None | pCASCADE-gltA1-zwf-pykA-pykF | None | 2.243429 | 3.99528 |
| 26 | gltA, pykA, pykF | None | pCASCADE-gltA2 | None | 1.442783 | 2.466254 |
| 27 | gltA, pykA, pykF | None | pCASCADE-gltA2-pykA-pykF | None | 1.381587 | 2.406065 |
| 28 | gltA, pykA, pykF | None | pCASCADE-gltA2-zwf | None | 1.382044 | 1.542374 |
| 29 | gltA, pykA, pykF | None | pCASCADE-gltA2-zwf-pykA-pykF | None | 1.183367 | 0.854238 |
| 30 | gltA, pykA, pykF | None | pCASCADE-pykA-pykF | None | 5.914064 | 5.735963 |
| 31 | gltA, pykA, pykF | None | pCASCADE-zwf | None | 0.668855 | 0.476328 |
| 32 | gltA, pykA, pykF | None | pCASCADE-zwf-pykA-pykF | None | 7.186233 | 5.833313 |
| 33 | gltA, zwf | None | pCASCADE-empty vector | None | 6.481895 | 4.151521 |
| 34 | gltA, zwf | None | pCASCADE-gltA1 | None | 1.805899 | 1.140859 |
| 35 | gltA, zwf | None | pCASCADE-gltA1-gltA2 | None | 1.363764 | 3.535358 |
| 36 | gltA, zwf | None | pCASCADE-gltA1-gltA2-pykA-pykF | None | 1.773825 | 3.693546 |
| 37 | gltA, zwf | None | pCASCADE-gltA1-gltA2-zwf | None | 2.907301 | 3.041142 |
| 38 | gltA, zwf | None | pCASCADE-gltA1-gltA2-zwf-pykA-pykF | None | 6.768355 | 4.839656 |
| 39 | gltA, zwf | None | pCASCADE-gltA1-pykA-pykF | None | 2.627482 | 2.937604 |

TABLE 1-continued

| Strain # | Genes with Proteolysis Tags | Chromosomal Gene Deletions | Gene Silencing | NADH Oxidase Expression Vector | 24 hour Pryuvate Titer (g/L) | 24 Hour Normalized Pyruvate Titer (g/L- |
|---|---|---|---|---|---|---|
| Pyruvate Production in MicroFermentations by engineered strains of *E. coli*. | | | | | | |
| 40 | gltA, zwf | None | pCASCADE-gltA1-zwf | None | 2.214957 | 2.763343 |
| 41 | gltA, zwf | None | pCASCADE-gltA1-zwf-pykA-pykF | None | 3.132929 | 7.155092 |
| 42 | gltA, zwf | None | pCASCADE-gltA2 | None | 1.69175 | 2.680298 |
| 43 | gltA, zwf | None | pCASCADE-gltA2-pykA-pykF | None | 1.828265 | 2.751795 |
| 44 | gltA, zwf | None | pCASCADE-gltA2-zwf | None | 1.451611 | 1.626382 |
| 45 | gltA, zwf | None | pCASCADE-gltA2-zwf-pykA-pykF | None | 1.717691 | 2.611901 |
| 46 | gltA, zwf | None | pCASCADE-pykA-pykF | None | 5.561404 | 3.495474 |
| 47 | gltA, zwf | None | pCASCADE-zwf | None | 0.248783 | 0.121037 |
| 48 | gltA, zwf | None | pCASCADE-zwf-pykA-pykF | None | 5.219484 | 5.439796 |
| 49 | gltA, zwf, pykA, pykF | None | pCASCADE-empty vector | None | 5.772126 | 3.779944 |
| 50 | gltA, zwf, pykA, pykF | None | pCASCADE-gltA1 | None | 3.206812 | 2.3104 |
| 51 | gltA, zwf, pykA, pykF | None | pCASCADE-gltA1-gltA2 | None | 1.63791 | 3.639719 |
| 52 | gltA, zwf, pykA, pykF | None | pCASCADE-gltA1-gltA2-pykA-pykF | None | 1.511753 | 3.482661 |
| 53 | gltA, zwf, pykA, pykF | None | pCASCADE-gltA1-gltA2-zwf | None | 1.814503 | 2.026223 |
| 54 | gltA, zwf, pykA, pykF | None | pCASCADE-gltA1-gltA2-zwf-pykA-pykF | None | | 0 |
| 55 | gltA, zwf, pykA, pykF | None | pCASCADE-gltA1-pykA-pykF | None | 3.211797 | 3.542762 |
| 56 | gltA, zwf, pykA, pykF | None | pCASCADE-gltA1-zwf | None | 2.880992 | 3.144158 |
| 57 | gltA, zwf, pykA, pykF | None | pCASCADE-gltA1-zwf-pykA-pykF | None | 4.107069 | 4.565642 |
| 58 | gltA, zwf, pykA, pykF | None | pCASCADE-gltA2 | None | 1.643419 | 2.548133 |
| 59 | gltA, zwf, pykA, pykF | None | pCASCADE-gltA2-pykA-pykF | None | 1.265883 | 1.936015 |
| 60 | gltA, zwf, pykA, pykF | None | pCASCADE-gltA2-zwf | None | 1.778775 | 2.016111 |
| 61 | gltA, zwf, pykA, pykF | None | pCASCADE-gltA2-zwf-pykA-pykF | None | 1.715338 | 2.722327 |
| 62 | gltA, zwf, pykA, pykF | None | pCASCADE-zwf | None | 8.480922 | 5.741642 |
| 63 | gltA, zwf, pykA, pykF | None | pCASCADE-zwf-pykA-pykF | None | 7.410325 | 14.25967 |
| 64 | lpd | None | pCASCADE-empty vector | None | 1.626551 | 0.412412 |
| 65 | lpd | None | pCASCADE-gltA1 | None | 2.128559 | 4.257117 |
| 66 | lpd | None | pCASCADE-gltA1-gltA2 | None | 2.070359 | 3.175397 |
| 67 | lpd | None | pCASCADE-gltA1-gltA2-pykA-pykF | None | 1.054934 | 0.332158 |
| 68 | lpd | None | pCASCADE-gltA1-gltA2-zwf | None | 2.263284 | 2.707277 |
| 69 | lpd | None | pCASCADE-gltA1-gltA2-zwf-pykA-pykF | None | 1.334917 | 0.975817 |
| 70 | lpd | None | pCASCADE-gltA1-pykA-pykF | None | 1.087234 | 0.269651 |
| 71 | lpd | None | pCASCADE-gltA1-zwf | None | 2.451736 | 0.832791 |
| 72 | lpd | None | pCASCADE-gltA1-zwf-pykA-pykF | None | 0.876629 | 1.274169 |
| 73 | lpd | None | pCASCADE-gltA2 | None | 1.14362 | 0.746488 |
| 74 | lpd | None | pCASCADE-gltA2-pykA-pykF | None | 3.374363 | 0.833588 |
| 75 | lpd | None | pCASCADE-gltA2-zwf | None | 1.071412 | 3.151213 |
| 76 | lpd | None | pCASCADE-gltA2-zwf-pykA-pykF | None | 1.383387 | 1.801285 |
| 77 | lpd | None | pCASCADE-pykA-pykF | None | 1.348538 | 0.54028 |
| 78 | lpd | None | pCASCADE-zwf | None | 1.439127 | 0.922517 |
| 79 | lpd | None | pCASCADE-zwf-pykA-pykF | None | 1.669276 | 0.925319 |
| 80 | lpd, gltA | None | pCASCADE-empty vector | None | 5.590723 | 3.831887 |
| 81 | lpd, gltA | None | pCASCADE-gltA1 | None | 6.355754 | 6.76144 |
| 82 | lpd, gltA | None | pCASCADE-gltA1-gltA2 | None | 1.650923 | 1.727412 |
| 83 | lpd, gltA | None | pCASCADE-gltA1-gltA2-pykA-pykF | None | 8.728136 | 3.565415 |
| 84 | lpd, gltA | None | pCASCADE-gltA1-gltA2-zwf | None | 2.35574 | 1.335454 |
| 85 | lpd, gltA | None | pCASCADE-gltA1-gltA2-zwf-pykA-pykF | None | 2.344075 | 2.675885 |
| 86 | lpd, gltA | None | pCASCADE-gltA1-pykA-pykF | None | 7.569212 | 2.045733 |
| 87 | lpd, gltA | None | pCASCADE-gltA1-zwf | None | 6.968887 | 4.45581 |
| 88 | lpd, gltA | None | pCASCADE-gltA1-zwf-pykA-pykF | None | 2.368826 | 2.322378 |
| 89 | lpd, gltA | None | pCASCADE-gltA2 | None | 2.416623 | 3.082428 |
| 90 | lpd, gltA | None | pCASCADE-gltA2-pykA-pykF | None | 7.801392 | 4.88809 |
| 91 | lpd, gltA | None | pCASCADE-gltA2-zwf | None | 2.344589 | 3.733422 |
| 92 | lpd, gltA | None | pCASCADE-gltA2-zwf-pykA-pykF | None | 1.924203 | 1.444597 |
| 93 | lpd, gltA | None | pCASCADE-pykA-pykF | None | 7.148925 | 1.946875 |
| 94 | lpd, gltA | None | pCASCADE-zwf | None | 7.49176 | 2.051413 |
| 95 | lpd, gltA | None | pCASCADE-zwf-pykA-pykF | None | 2.144874 | 0.624963 |

TABLE 1-continued

| Pyruvate Production in MicroFermentations by engineered strains of *E. coli*. | | | | | | |
|---|---|---|---|---|---|---|
| Strain # | Genes with Proteolysis Tags | Chromosomal Gene Deletions | Gene Silencing | NADH Oxidase Expression Vector | 24 hour Pryuvate Titer (g/L) | 24 Hour Normalized Pyruvate Titer (g/L- |
| 96 | lpd, gltA, pykA, pykF | None | pCASCADE-empty vector | None | | 0 |
| 97 | lpd, gltA, pykA, pykF | None | pCASCADE-gltA1 | None | | 0 |
| 98 | lpd, gltA, pykA, pykF | None | pCASCADE-gltA1-gltA2 | None | | 0 |
| 99 | lpd, gltA, pykA, pykF | None | pCASCADE-gltA1-gltA2-pykA-pykF | None | | 0 |
| 100 | lpd, gltA, pykA, pykF | None | pCASCADE-gltA1-gltA2-zwf | None | 1.887489 | 1.815906 |
| 101 | lpd, gltA, pykA, pykF | None | pCASCADE-gltA1-gltA2-zwf-pykA-pykF | None | | 0 |
| 102 | lpd, gltA, pykA, pykF | None | pCASCADE-gltA1-pykA-pykF | None | | 0 |
| 103 | lpd, gltA, pykA, pykF | None | pCASCADE-gltA1-zwf | None | | 0 |
| 104 | lpd, gltA, pykA, pykF | None | pCASCADE-gltA2 | None | | 0 |
| 105 | lpd, gltA, pykA, pykF | None | pCASCADE-gltA2-pykA-pykF | None | | 0 |
| 106 | lpd, gltA, pykA, pykF | None | pCASCADE-gltA2-zwf | None | 2.507271 | 3.663619 |
| 107 | lpd, gltA, pykA, pykF | None | pCASCADE-gltA2-zwf-pykA-pykF | None | | 0 |
| 108 | lpd, gltA, pykA, pykF | None | pCASCADE-pykA-pykF | None | | 0 |
| 109 | lpd, gltA, pykA, pykF | None | pCASCADE-zwf | None | 0.412556 | 0.266492 |
| 110 | lpd, gltA, pykA, pykF | None | pCASCADE-zwf-pykA-pykF | None | | 0 |
| 111 | lpd, gltA, zwf | None | pCASCADE-empty vector | None | 4.163291 | 4.756634 |
| 112 | lpd, gltA, zwf | None | pCASCADE-gltA1 | None | 3.90461 | 2.297046 |
| 113 | lpd, gltA, zwf | None | pCASCADE-gltA1-gltA2 | None | 1.815815 | 2.846417 |
| 114 | lpd, gltA, zwf | None | pCASCADE-gltA1-gltA2-pykA-pykF | None | 1.351396 | 3.223518 |
| 115 | lpd, gltA, zwf | None | pCASCADE-gltA1-gltA2-zwf | None | 2.495417 | 1.969081 |
| 116 | lpd, gltA, zwf | None | pCASCADE-gltA1-gltA2-zwf-pykA-pykF | None | 4.065545 | 4.626404 |
| 117 | lpd, gltA, zwf | None | pCASCADE-gltA1-pykA-pykF | None | 4.617462 | 4.703824 |
| 118 | lpd, gltA, zwf | None | pCASCADE-gltA1-zwf | None | 3.555241 | 4.097316 |
| 119 | lpd, gltA, zwf | None | pCASCADE-gltA1-zwf-pykA-pykF | None | 4.5642 | 3.105891 |
| 120 | lpd, gltA, zwf | None | pCASCADE-gltA2 | None | 2.208222 | 2.828299 |
| 121 | lpd, gltA, zwf | None | pCASCADE-gltA2-pykA-pykF | None | 1.770202 | 2.686235 |
| 122 | lpd, gltA, zwf | None | pCASCADE-gltA2-zwf | None | 1.806209 | 2.062353 |
| 123 | lpd, gltA, zwf | None | pCASCADE-gltA2-zwf-pykA-pykF | None | 2.224844 | 1.363429 |
| 124 | lpd, gltA, zwf | None | pCASCADE-pykA-pykF | None | 6.923406 | 4.839343 |
| 125 | lpd, gltA, zwf | None | pCASCADE-zwf | None | 0.190025 | 0.11843 |
| 126 | lpd, gltA, zwf | None | pCASCADE-zwf-pykA-pykF | None | 7.182654 | 4.351277 |
| 127 | lpd, gltA, zwf, pykA, pykF | None | pCASCADE-empty vector | None | 4.242052 | 4.090736 |
| 128 | lpd, gltA, zwf, pykA, pykF | None | pCASCADE-gltA1 | None | | 0 |
| 129 | lpd, gltA, zwf, pykA, pykF | None | pCASCADE-gltA1-gltA2 | None | 3.324025 | 3.839208 |
| 130 | lpd, gltA, zwf, pykA, pykF | None | pCASCADE-gltA1-gltA2-pykA-pykF | None | 1.319675 | 3.166208 |
| 131 | lpd, gltA, zwf, pykA, pykF | None | pCASCADE-gltA1-gltA2-zwf-pykA-pykF | None | 4.420189 | 5.357545 |
| 132 | lpd, gltA, zwf, pykA, pykF | None | pCASCADE-gltA1-pykA-pykF | None | 1.782848 | 3.78251 |
| 133 | lpd, gltA, zwf, pykA, pykF | None | pCASCADE-gltA1-zwf | None | | 0 |
| 134 | lpd, gltA, zwf, pykA, pykF | None | pCASCADE-gltA2 | None | | 0 |
| 135 | lpd, gltA, zwf, pykA, pykF | None | pCASCADE-gltA2-pykA-pykF | None | 2.478112 | 4.155466 |
| 136 | lpd, gltA, zwf, pykA, pykF | None | pCASCADE-gltA2-zwf-pykA-pykF | None | | 0 |
| 137 | lpd, gltA, zwf, pykA, pykF | None | pCASCADE-pykA-pykF | None | | 0 |
| 138 | lpd, gltA, zwf, pykA, pykF | None | pCASCADE-zwf | None | | 0 |
| 139 | lpd, gltA, zwf, pykA, pykF | None | pCASCADE-zwf-pykA-pykF | None | 3.693888 | 7.828024 |

TABLE 1-continued

Pyruvate Production in MicroFermentations by engineered strains of *E. coli*.

| Strain # | Genes with Proteolysis Tags | Chromosomal Gene Deletions | Gene Silencing | NADH Oxidase Expression Vector | 24 hour Pryuvate Titer (g/L) | 24 Hour Normalized Pyruvate Titer (g/L- |
|---|---|---|---|---|---|---|
| 140 | lpd, zwf | None | pCASCADE-empty vector | None | 2.195519 | 0.782995 |
| 141 | lpd, zwf | None | pCASCADE-gltA1 | None | 1.87622 | 2.132068 |
| 142 | lpd, zwf | None | pCASCADE-gltA1-gltA2 | None | 1.964431 | 2.698394 |
| 143 | lpd, zwf | None | pCASCADE-gltA1-gltA2-pykA-pykF | None | 1.418538 | 0.604147 |
| 144 | lpd, zwf | None | pCASCADE-gltA1-gltA2-zwf | None | 1.9114 | 1.137738 |
| 145 | lpd, zwf | None | pCASCADE-gltA1-gltA2-zwf-pykA-pykF | None | 1.105357 | 0.714055 |
| 146 | lpd, zwf | None | pCASCADE-gltA1-pykA-pykF | None | 2.218935 | 0.645039 |
| 147 | lpd, zwf | None | pCASCADE-gltA1-zwf | None | 2.43108 | 0.724398 |
| 148 | lpd, zwf | None | pCASCADE-gltA1-zwf-pykA-pykF | None | 1.202002 | 0.805632 |
| 149 | lpd, zwf | None | pCASCADE-gltA2 | None | 1.188285 | 0.83447 |
| 150 | lpd, zwf | None | pCASCADE-gltA2-pykA-pykF | None | 2.268933 | 0.57763 |
| 151 | lpd, zwf | None | pCASCADE-gltA2-zwf | None | 1.075495 | 0.759531 |
| 152 | lpd, zwf | None | pCASCADE-gltA2-zwf-pykA-pykF | None | 1.609353 | 1.146263 |
| 153 | lpd, zwf | None | pCASCADE-pykA-pykF | None | 2.55484 | 0.716042 |
| 154 | lpd, zwf | None | pCASCADE-zwf | None | 2.692122 | 0.964227 |
| 155 | lpd, zwf | None | pCASCADE-zwf-pykA-pykF | None | 1.66086 | 0.542765 |
| 156 | None | None | pCASCADE-empty vector | None | | 0 |
| 157 | None | None | pCASCADE-gltA1 | None | | 0 |
| 158 | None | None | pCASCADE-gltA1-gltA2 | None | 1.935203 | 2.658246 |
| 159 | None | None | pCASCADE-gltA1-gltA2-pykA-pykF | None | | 0 |
| 160 | None | None | pCASCADE-gltA1-gltA2-zwf | None | 1.220768 | 0.678204 |
| 161 | None | None | pCASCADE-gltA1-gltA2-zwf-pykA-pykF | None | | 0 |
| 162 | None | None | pCASCADE-gltA1-pykA-pykF | None | | 0 |
| 163 | None | None | pCASCADE-gltA1-zwf | None | | 0 |
| 164 | None | None | pCASCADE-gltA1-zwf-pykA-pykF | None | | 0 |
| 165 | None | None | pCASCADE-gltA2 | None | | 0 |
| 166 | None | None | pCASCADE-gltA2-pykA-pykF | None | | 0 |
| 167 | None | None | pCASCADE-gltA2-zwf | None | | 0 |
| 168 | None | None | pCASCADE-gltA2-zwf-pykA-pykF | None | | 0 |
| 169 | None | None | pCASCADE-pykA-pykF | None | | 0 |
| 170 | None | None | pCASCADE-zwf | None | | 0 |
| 171 | None | None | pCASCADE-zwf-pykA-pykF | None | 1.531818 | 0.479893 |
| 172 | pykA, pykF | None | pCASCADE-empty vector | None | | 0 |
| 173 | pykA, pykF | None | pCASCADE-gltA1 | None | | 0 |
| 174 | pykA, pykF | None | pCASCADE-gltA1-gltA2 | None | 0.994998 | 2.381061 |
| 175 | pykA, pykF | None | pCASCADE-gltA1-gltA2-pykA-pykF | None | | 0 |
| 176 | pykA, pykF | None | pCASCADE-gltA1-gltA2-zwf | None | 0.743998 | 0.868244 |
| 177 | pykA, pykF | None | pCASCADE-gltA1-gltA2-zwf-pykA-pykF | None | | 0 |
| 178 | pykA, pykF | None | pCASCADE-gltA1-pykA-pykF | None | | 0 |
| 179 | pykA, pykF | None | pCASCADE-gltA1-zwf | None | | 0 |
| 180 | pykA, pykF | None | pCASCADE-gltA1-zwf-pykA-pykF | None | | 0 |
| 181 | pykA, pykF | None | pCASCADE-gltA2 | None | | 0 |
| 182 | pykA, pykF | None | pCASCADE-gltA2-pykA-pykF | None | | 0 |
| 183 | pykA, pykF | None | pCASCADE-gltA2-zwf | None | | 0 |
| 184 | pykA, pykF | None | pCASCADE-gltA2-zwf-pykA-pykF | None | | 0 |
| 185 | pykA, pykF | None | pCASCADE-pykA-pykF | None | | 0 |
| 186 | pykA, pykF | None | pCASCADE-zwf | None | | 0 |
| 187 | pykA, pykF | None | pCASCADE-zwf-pykA-pykF | None | | 0 |
| 188 | zwf | None | pCASCADE-empty vector | None | 0.48452 | 0.140359 |
| 189 | zwf | None | pCASCADE-gltA1 | None | 1.677519 | 3.584443 |
| 190 | zwf | None | pCASCADE-gltA1-gltA2 | None | 2.44634 | 0.798414 |
| 191 | zwf | None | pCASCADE-gltA1-gltA2-pykA-pykF | None | 0.733646 | 0.264663 |
| 192 | zwf | None | pCASCADE-gltA1-gltA2-zwf | None | 1.983733 | 2.637943 |
| 193 | zwf | None | pCASCADE-gltA1-gltA2-zwf-pykA-pykF | None | 2.266191 | 0.565417 |
| 194 | zwf | None | pCASCADE-gltA1-pykA-pykF | None | 1.001772 | 0.30654 |
| 195 | zwf | None | pCASCADE-gltA1-zwf | None | 1.552254 | 0.437008 |
| 196 | zwf | None | pCASCADE-gltA1-zwf-pykA-pykF | None | 1.932433 | 3.378379 |
| 197 | zwf | None | pCASCADE-gltA2 | None | 2.215242 | 0.575089 |
| 198 | zwf | None | pCASCADE-gltA2-pykA-pykF | None | 1.848844 | 0.461749 |
| 199 | zwf | None | pCASCADE-gltA2-zwf | None | 1.899225 | 2.472949 |
| 200 | zwf | None | pCASCADE-gltA2-zwf-pykA-pykF | None | 1.37267 | 2.660213 |
| 201 | zwf | None | pCASCADE-pykA-pykF | None | 0.948317 | 0.487817 |
| 202 | zwf | None | pCASCADE-zwf | None | 0.774174 | 0.875763 |
| 203 | zwf | None | pCASCADE-zwf-pykA-pykF | None | 4.251237 | 4.251237 |
| 204 | gltA | None | pCASCADE-empty vector | pCDF-nox | 2.994474 | 3.771425 |
| 205 | gltA | None | pCASCADE-gltA1 | pCDF-nox | 1.862628 | 2.593756 |
| 206 | gltA | None | pCASCADE-gltA1-gltA2 | pCDF-nox | 1.007197 | 3.14877 |
| 207 | gltA | None | pCASCADE-gltA1-gltA2-pykA-pykF | pCDF-nox | 1.169942 | 3.316068 |
| 208 | gltA | None | pCASCADE-gltA1-gltA2-zwf | pCDF-nox | 1.148563 | 1.754416 |

TABLE 1-continued

Pyruvate Production in MicroFermentations by engineered strains of *E. coli*.

| Strain # | Genes with Proteolysis Tags | Chromosomal Gene Deletions | Gene Silencing | NADH Oxidase Expression Vector | 24 hour Pryuvate Titer (g/L) | 24 Hour Normalized Pyruvate Titer (g/L- |
|---|---|---|---|---|---|---|
| 209 | gltA | None | pCASCADE-gltA1-gltA2-zwf-pykA-pykF | pCDF-nox | 1.756779 | 5.076515 |
| 210 | gltA | None | pCASCADE-gltA1-pykA-pykF | pCDF-nox | 1.862411 | 3.223726 |
| 211 | gltA | None | pCASCADE-gltA1-zwf | pCDF-nox | 1.725361 | 3.059423 |
| 212 | gltA | None | pCASCADE-gltA1-zwf-pykA-pykF | pCDF-nox | 1.678689 | 2.667593 |
| 213 | gltA | None | pCASCADE-gltA2 | pCDF-nox | 1.683244 | 4.230319 |
| 214 | gltA | None | pCASCADE-gltA2-pykA-pykF | pCDF-nox | 1.269628 | 3.680294 |
| 215 | gltA | None | pCASCADE-gltA2-zwf | pCDF-nox | 1.685963 | 1.992629 |
| 216 | gltA | None | pCASCADE-gltA2-zwf-pykA-pykF | pCDF-nox | 1.5489 | 3.475285 |
| 217 | gltA | None | pCASCADE-pykA-pykF | pCDF-nox | 3.401353 | 4.661111 |
| 218 | gltA | None | pCASCADE-zwf | pCDF-nox | 3.478002 | 4.920911 |
| 219 | gltA | None | pCASCADE-zwf-pykA-pykF | pCDF-nox | 3.925427 | 7.573365 |
| 220 | gltA, pykA, pykF | None | pCASCADE-empty vector | pCDF-nox | 5.787515 | 5.907134 |
| 221 | gltA, pykA, pykF | None | pCASCADE-gltA1 | pCDF-nox | 3.815812 | 3.654957 |
| 222 | gltA, pykA, pykF | None | pCASCADE-gltA1-gltA2 | pCDF-nox | 1.405854 | 3.85493 |
| 223 | gltA, pykA, pykF | None | pCASCADE-gltA1-gltA2-pykA-pykF | pCDF-nox | 1.562872 | 3.857133 |
| 224 | gltA, pykA, pykF | None | pCASCADE-gltA1-gltA2-zwf-pykA-pykF | pCDF-nox | 1.077614 | 3.094636 |
| 225 | gltA, pykA, pykF | None | pCASCADE-gltA1-pykA-pykF | pCDF-nox | 2.690626 | 3.65202 |
| 226 | gltA, pykA, pykF | None | pCASCADE-gltA1-zwf | pCDF-nox | 2.114894 | 2.897114 |
| 227 | gltA, pykA, pykF | None | pCASCADE-gltA1-zwf-pykA-pykF | pCDF-nox | 2.200602 | 2.049016 |
| 228 | gltA, pykA, pykF | None | pCASCADE-gltA2 | pCDF-nox | 1.637188 | 3.391869 |
| 229 | gltA, pykA, pykF | None | pCASCADE-gltA2-pykA-pykF | pCDF-nox | 1.581651 | 3.579125 |
| 230 | gltA, pykA, pykF | None | pCASCADE-gltA2-zwf | pCDF-nox | 1.395467 | 1.661488 |
| 231 | gltA, pykA, pykF | None | pCASCADE-gltA2-zwf-pykA-pykF | pCDF-nox | | 0 |
| 232 | gltA, pykA, pykF | None | pCASCADE-pykA-pykF | pCDF-nox | 4.943349 | 5.012369 |
| 233 | gltA, pykA, pykF | None | pCASCADE-zwf | pCDF-nox | 5.154877 | 5.303808 |
| 234 | gltA, pykA, pykF | None | pCASCADE-zwf-pykA-pykF | pCDF-nox | 7.308858 | 7.275463 |
| 235 | gltA, zwf | None | pCASCADE-empty vector | pCDF-nox | 6.068373 | 5.302436 |
| 236 | gltA, zwf | None | pCASCADE-gltA1 | pCDF-nox | 2.906389 | 4.428513 |
| 237 | gltA, zwf | None | pCASCADE-gltA1-gltA2 | pCDF-nox | 1.891147 | 6.640964 |
| 238 | gltA, zwf | None | pCASCADE-gltA1-gltA2-pykA-pykF | pCDF-nox | 1.216316 | 2.779578 |
| 239 | gltA, zwf | None | pCASCADE-gltA1-pykA-pykF | pCDF-nox | 3.218554 | 4.248692 |
| 240 | gltA, zwf | None | pCASCADE-gltA1-zwf | pCDF-nox | 2.049991 | 2.791686 |
| 241 | gltA, zwf | None | pCASCADE-gltA2 | pCDF-nox | | 0 |
| 242 | gltA, zwf | None | pCASCADE-gltA2-pykA-pykF | pCDF-nox | 1.667479 | 3.308424 |
| 243 | gltA, zwf | None | pCASCADE-gltA2-zwf | pCDF-nox | 0.940073 | 1.907074 |
| 244 | gltA, zwf | None | pCASCADE-gltA2-zwf-pykA-pykF | pCDF-nox | 1.309984 | 2.897104 |
| 245 | gltA, zwf | None | pCASCADE-pykA-pykF | pCDF-nox | 6.668118 | 313.7938 |
| 246 | gltA, zwf | None | pCASCADE-zwf | pCDF-nox | 0.169753 | 8.091173 |
| 247 | gltA, zwf | None | pCASCADE-zwf-pykA-pykF | pCDF-nox | 6.250439 | 7.890972 |
| 248 | gltA, zwf, pykA, pykF | None | pCASCADE-empty vector | pCDF-nox | | 0 |
| 249 | gltA, zwf, pykA, pykF | None | pCASCADE-gltA1-gltA2 | pCDF-nox | 2.074567 | 4.761458 |
| 250 | gltA, zwf, pykA, pykF | None | pCASCADE-gltA1-gltA2-pykA-pykF | pCDF-nox | 1.545728 | 3.583217 |
| 251 | gltA, zwf, pykA, pykF | None | pCASCADE-gltA1-gltA2-zwf-pykA-pykF | pCDF-nox | 0.175741 | 7.421514 |
| 252 | gltA, zwf, pykA, pykF | None | pCASCADE-gltA1-pykA-pykF | pCDF-nox | 2.715614 | 3.702218 |
| 253 | gltA, zwf, pykA, pykF | None | pCASCADE-gltA1-zwf | pCDF-nox | 2.613912 | 3.338671 |
| 254 | gltA, zwf, pykA, pykF | None | pCASCADE-gltA2 | pCDF-nox | 1.712319 | 3.201853 |
| 255 | gltA, zwf, pykA, pykF | None | pCASCADE-gltA2-pykA-pykF | pCDF-nox | 1.849683 | 3.629106 |
| 256 | gltA, zwf, pykA, pykF | None | pCASCADE-gltA2-zwf | pCDF-nox | 1.154281 | 2.364942 |
| 257 | gltA, zwf, pykA, pykF | None | pCASCADE-gltA2-zwf-pykA-pykF | pCDF-nox | 1.240534 | 2.982126 |
| 258 | gltA, zwf, pykA, pykF | None | pCASCADE-pykA-pykF | pCDF-nox | | 0 |
| 259 | gltA, zwf, pykA, pykF | None | pCASCADE-zwf | pCDF-nox | 0.234393 | 0.186545 |
| 260 | gltA, zwf, pykA, pykF | None | pCASCADE-zwf-pykA-pykF | pCDF-nox | 0.16027 | 0.256555 |
| 261 | lpd | None | pCASCADE-empty vector | pCDF-nox | 4.376713 | 3.361195 |
| 262 | lpd | None | pCASCADE-gltA1 | pCDF-nox | 2.04663 | 2.057742 |
| 263 | lpd | None | pCASCADE-gltA1-gltA2 | pCDF-nox | 2.184127 | 6.115776 |
| 264 | lpd | None | pCASCADE-gltA1-gltA2-pykA-pykF | pCDF-nox | 1.803429 | 5.178993 |
| 265 | lpd | None | pCASCADE-gltA1-gltA2-zwf | pCDF-nox | 1.867143 | 2.835664 |

TABLE 1-continued

Pyruvate Production in MicroFermentations by engineered strains of *E. coli*.

| Strain # | Genes with Proteolysis Tags | Chromosomal Gene Deletions | Gene Silencing | NADH Oxidase Expression Vector | 24 hour Pryuvate Titer (g/L) | 24 Hour Normalized Pyruvate Titer (g/L- |
|---|---|---|---|---|---|---|
| 266 | lpd | None | pCASCADE-gltA1-gltA2-zwf-pykA-pykF | pCDF-nox | 1.673461 | 5.99592 |
| 267 | lpd | None | pCASCADE-gltA1-pykA-pykF | pCDF-nox | 0.547288 | 27.50189 |
| 268 | lpd | None | pCASCADE-gltA1-zwf | pCDF-nox | 2.375918 | 3.533016 |
| 269 | lpd | None | pCASCADE-gltA1-zwf-pykA-pykF | pCDF-nox | | 0 |
| 270 | lpd | None | pCASCADE-gltA2 | pCDF-nox | 2.528549 | 4.302375 |
| 271 | lpd | None | pCASCADE-gltA2-pykA-pykF | pCDF-nox | 1.380511 | 2.352209 |
| 272 | lpd | None | pCASCADE-gltA2-zwf | pCDF-nox | 1.425502 | 2.860501 |
| 273 | lpd | None | pCASCADE-gltA2-zwf-pykA-pykF | pCDF-nox | 0.228188 | 0.553209 |
| 274 | lpd | None | pCASCADE-pykA-pykF | pCDF-nox | 3.595425 | 4.370753 |
| 275 | lpd | None | pCASCADE-zwf | pCDF-nox | | 0 |
| 276 | lpd | None | pCASCADE-zwf-pykA-pykF | pCDF-nox | 3.542121 | 5.410545 |
| 277 | lpd, gltA | None | pCASCADE-empty vector | pCDF-nox | 5.179109 | 5.445217 |
| 278 | lpd, gltA | None | pCASCADE-gltA1 | pCDF-nox | 2.894256 | 2.311374 |
| 279 | lpd, gltA | None | pCASCADE-gltA1-gltA2 | pCDF-nox | 1.204914 | 3.415192 |
| 280 | lpd, gltA | None | pCASCADE-gltA1-gltA2-pykA-pykF | pCDF-nox | 1.827513 | 4.462683 |
| 281 | lpd, gltA | None | pCASCADE-gltA1-gltA2-zwf-pykA-pykF | pCDF-nox | 3.199911 | 3.929936 |
| 282 | lpd, gltA | None | pCASCADE-gltA1-pykA-pykF | pCDF-nox | 4.093769 | 6.196953 |
| 283 | lpd, gltA | None | pCASCADE-gltA1-zwf | pCDF-nox | 3.36976 | 5.852004 |
| 284 | lpd, gltA | None | pCASCADE-gltA2 | pCDF-nox | 2.939899 | 6.572397 |
| 285 | lpd, gltA | None | pCASCADE-gltA2-pykA-pykF | pCDF-nox | 2.278146 | 4.946683 |
| 286 | lpd, gltA | None | pCASCADE-gltA2-zwf-pykA-pykF | pCDF-nox | 2.820681 | 5.358233 |
| 287 | lpd, gltA | None | pCASCADE-zwf | pCDF-nox | 3.233077 | 2.87451 |
| 288 | lpd, gltA | None | pCASCADE-zwf-pykA-pykF | pCDF-nox | 6.800414 | 9.71446 |
| 289 | lpd, gltA, pykA, pykF | None | pCASCADE-empty vector | pCDF-nox | | 0 |
| 290 | lpd, gltA, pykA, pykF | None | pCASCADE-gltA1 | pCDF-nox | 8.03826 | 8.340001 |
| 291 | lpd, gltA, pykA, pykF | None | pCASCADE-gltA1-gltA2-pykA-pykF | pCDF-nox | 1.552227 | 4.725054 |
| 292 | lpd, gltA, pykA, pykF | None | pCASCADE-gltA1-gltA2-zwf | pCDF-nox | 2.185541 | 6.115112 |
| 293 | lpd, gltA, pykA, pykF | None | pCASCADE-gltA1-gltA2-zwf-pykA-pykF | pCDF-nox | | 0 |
| 294 | lpd, gltA, pykA, pykF | None | pCASCADE-gltA1-pykA-pykF | pCDF-nox | 4.280626 | 6.225369 |
| 295 | lpd, gltA, pykA, pykF | None | pCASCADE-gltA2-pykA-pykF | pCDF-nox | 4.26763 | 8.841531 |
| 296 | lpd, gltA, pykA, pykF | None | pCASCADE-gltA2-zwf | pCDF-nox | 3.855886 | 8.57874 |
| 297 | lpd, gltA, pykA, pykF | None | pCASCADE-pykA-pykF | pCDF-nox | | 0 |
| 298 | lpd, gltA, pykA, pykF | None | pCASCADE-zwf | pCDF-nox | 8.447011 | 7.519215 |
| 299 | lpd, gltA, zwf | None | pCASCADE-empty vector | pCDF-nox | 4.822733 | 4.659195 |
| 300 | lpd, gltA, zwf | None | pCASCADE-gltA1-gltA2 | pCDF-nox | 2.158706 | 5.196068 |
| 301 | lpd, gltA, zwf | None | pCASCADE-gltA1-gltA2-pykA-pykF | pCDF-nox | 1.604957 | 3.843196 |
| 302 | lpd, gltA, zwf | None | pCASCADE-gltA1-gltA2-zwf | pCDF-nox | 2.101259 | 2.026306 |
| 303 | lpd, gltA, zwf | None | pCASCADE-gltA1-gltA2-zwf-pykA-pykF | pCDF-nox | 1.141694 | 4.03982 |
| 304 | lpd, gltA, zwf | None | pCASCADE-gltA1-pykA-pykF | pCDF-nox | 2.991522 | 3.936369 |
| 305 | lpd, gltA, zwf | None | pCASCADE-gltA1-zwf | pCDF-nox | 2.303922 | 3.215522 |
| 306 | lpd, gltA, zwf | None | pCASCADE-gltA2 | pCDF-nox | 2.227893 | 4.514656 |
| 307 | lpd, gltA, zwf | None | pCASCADE-gltA2-pykA-pykF | pCDF-nox | 2.153473 | 3.78413 |
| 308 | lpd, gltA, zwf | None | pCASCADE-gltA2-zwf | pCDF-nox | 1.858938 | 3.720182 |
| 309 | lpd, gltA, zwf | None | pCASCADE-gltA2-zwf-pykA-pykF | pCDF-nox | 2.062681 | 4.223776 |
| 310 | lpd, gltA, zwf | None | pCASCADE-pykA-pykF | pCDF-nox | | 0 |
| 311 | lpd, gltA, zwf | None | pCASCADE-zwf-pykA-pykF | pCDF-nox | 5.10091 | 7.184178 |
| 312 | lpd, gltA, zwf, pykA, pykF | None | pCASCADE-gltA1 | pCDF-nox | | 0 |
| 313 | lpd, gltA, zwf, pykA, pykF | None | pCASCADE-gltA2 | pCDF-nox | | 0 |
| 314 | lpd, gltA, zwf, pykA, pykF | None | pCASCADE-zwf | pCDF-nox | | 0 |
| 315 | lpd, zwf | None | pCASCADE-empty vector | pCDF-nox | 3.295953 | 2.717124 |
| 316 | lpd, zwf | None | pCASCADE-gltA1 | pCDF-nox | 2.004334 | 1.737009 |
| 317 | lpd, zwf | None | pCASCADE-gltA1-gltA2 | pCDF-nox | 2.14836 | 5.742128 |
| 318 | lpd, zwf | None | pCASCADE-gltA1-gltA2-pykA-pykF | pCDF-nox | 1.615304 | 4.175747 |
| 319 | lpd, zwf | None | pCASCADE-gltA1-gltA2-zwf | pCDF-nox | 1.646336 | 2.637682 |
| 320 | lpd, zwf | None | pCASCADE-gltA1-gltA2-zwf-pykA-pykF | pCDF-nox | 1.959566 | 6.973794 |
| 321 | lpd, zwf | None | pCASCADE-gltA1-pykA-pykF | pCDF-nox | 3.382341 | 3.928615 |

TABLE 1-continued

Pyruvate Production in MicroFermentations by engineered strains of *E. coli*.

| Strain # | Genes with Proteolysis Tags | Chromosomal Gene Deletions | Gene Silencing | NADH Oxidase Expression Vector | 24 hour Pryuvate Titer (g/L) | 24 Hour Normalized Pyruvate Titer (g/L- |
|---|---|---|---|---|---|---|
| 322 | lpd, zwf | None | pCASCADE-gltA1-zwf | pCDF-nox | 3.418304 | 4.087022 |
| 323 | lpd, zwf | None | pCASCADE-gltA1-zwf-pykA-pykF | pCDF-nox | 1.429885 | 3.883446 |
| 324 | lpd, zwf | None | pCASCADE-gltA2 | pCDF-nox | 1.17526 | 2.278122 |
| 325 | lpd, zwf | None | pCASCADE-gltA2-pykA-pykF | pCDF-nox | 0.99175 | 1.730411 |
| 326 | lpd, zwf | None | pCASCADE-gltA2-zwf | pCDF-nox | 1.303131 | 2.203132 |
| 327 | lpd, zwf | None | pCASCADE-gltA2-zwf-pykA-pykF | pCDF-nox | 1.476491 | 2.806216 |
| 328 | lpd, zwf | None | pCASCADE-pykA-pykF | pCDF-nox | 3.372472 | 3.379772 |
| 329 | lpd, zwf | None | pCASCADE-zwf | pCDF-nox | 3.362499 | 3.15467 |
| 330 | lpd, zwf | None | pCASCADE-zwf-pykA-pykF | pCDF-nox | 3.89799 | 6.046395 |
| 331 | None | None | pCASCADE-empty vector | pCDF-nox | | 0 |
| 332 | None | None | pCASCADE-gltA1 | pCDF-nox | | 0 |
| 333 | None | None | pCASCADE-gltA1-gltA2 | pCDF-nox | 1.550647 | 3.857811 |
| 334 | None | None | pCASCADE-gltA1-gltA2-pykA-pykF | pCDF-nox | 1.626857 | 3.941507 |
| 335 | None | None | pCASCADE-gltA1-gltA2-zwf | pCDF-nox | 2.067611 | 2.753914 |
| 336 | None | None | pCASCADE-gltA1-gltA2-zwf-pykA-pykF | pCDF-nox | | 0 |
| 337 | None | None | pCASCADE-gltA1-pykA-pykF | pCDF-nox | | 0 |
| 338 | None | None | pCASCADE-gltA1-zwf | pCDF-nox | | 0 |
| 339 | None | None | pCASCADE-gltA1-zwf-pykA-pykF | pCDF-nox | | 0 |
| 340 | None | None | pCASCADE-gltA2 | pCDF-nox | 0.47467 | 0.945332 |
| 341 | None | None | pCASCADE-gltA2-pykA-pykF | pCDF-nox | 0.505176 | 0.87895 |
| 342 | None | None | pCASCADE-gltA2-zwf | pCDF-nox | 0.690594 | 1.171828 |
| 343 | None | None | pCASCADE-gltA2-zwf-pykA-pykF | pCDF-nox | 0.326887 | 0.602724 |
| 344 | None | None | pCASCADE-pykA-pykF | pCDF-nox | | 0 |
| 345 | None | None | pCASCADE-zwf | pCDF-nox | | 0 |
| 346 | None | None | pCASCADE-zwf-pykA-pykF | pCDF-nox | | 0 |
| 347 | pykA, pykF | None | pCASCADE-empty vector | pCDF-nox | | 0 |
| 348 | pykA, pykF | None | pCASCADE-gltA1 | pCDF-nox | | 0 |
| 349 | pykA, pykF | None | pCASCADE-gltA1-gltA2 | pCDF-nox | | 0 |
| 350 | pykA, pykF | None | pCASCADE-gltA1-gltA2-pykA-pykF | pCDF-nox | | 0 |
| 351 | pykA, pykF | None | pCASCADE-gltA1-gltA2-zwf | pCDF-nox | | 0 |
| 352 | pykA, pykF | None | pCASCADE-gltA1-gltA2-zwf-pykA-pykF | pCDF-nox | 2.045377 | 4.620023 |
| 353 | pykA, pykF | None | pCASCADE-gltA1-pykA-pykF | pCDF-nox | | 0 |
| 354 | pykA, pykF | None | pCASCADE-gltA1-zwf | pCDF-nox | | 0 |
| 355 | pykA, pykF | None | pCASCADE-gltA1-zwf-pykA-pykF | pCDF-nox | | 0 |
| 356 | pykA, pykF | None | pCASCADE-gltA2 | pCDF-nox | 1.118483 | 1.983301 |
| 357 | pykA, pykF | None | pCASCADE-gltA2-pykA-pykF | pCDF-nox | | 0 |
| 358 | pykA, pykF | None | pCASCADE-gltA2-zwf | pCDF-nox | | 0 |
| 359 | pykA, pykF | None | pCASCADE-gltA2-zwf-pykA-pykF | pCDF-nox | | 0 |
| 360 | pykA, pykF | None | pCASCADE-pykA-pykF | pCDF-nox | | 0 |
| 361 | pykA, pykF | None | pCASCADE-zwf | pCDF-nox | | 0 |
| 362 | pykA, pykF | None | pCASCADE-zwf-pykA-pykF | pCDF-nox | | 0 |
| 363 | zwf | None | pCASCADE-empty vector | pCDF-nox | | 0 |
| 364 | zwf | None | pCASCADE-gltA1 | pCDF-nox | | 0 |
| 365 | zwf | None | pCASCADE-gltA1-gltA2 | pCDF-nox | 1.776522 | 2.064739 |
| 366 | zwf | None | pCASCADE-gltA1-gltA2-pykA-pykF | pCDF-nox | 0.459614 | 0.565033 |
| 367 | zwf | None | pCASCADE-gltA1-gltA2-zwf | pCDF-nox | | 0 |
| 368 | zwf | None | pCASCADE-gltA1-pykA-pykF | pCDF-nox | 0.607424 | 0.776648 |
| 369 | zwf | None | pCASCADE-gltA1-zwf | pCDF-nox | 0.344144 | 0.527415 |
| 370 | zwf | None | pCASCADE-gltA1-zwf-pykA-pykF | pCDF-nox | | 0 |
| 371 | zwf | None | pCASCADE-gltA2 | pCDF-nox | 0.50789 | 0.668066 |
| 372 | zwf | None | pCASCADE-gltA2-pykA-pykF | pCDF-nox | 0.513826 | 0.584531 |
| 373 | zwf | None | pCASCADE-gltA2-zwf | pCDF-nox | 1.142363 | 2.518881 |
| 374 | zwf | None | pCASCADE-gltA2-zwf-pykA-pykF | pCDF-nox | 0.586813 | 1.446314 |
| 375 | zwf | None | pCASCADE-pykA-pykF | pCDF-nox | | 0 |
| 376 | zwf | None | pCASCADE-zwf | pCDF-nox | | 0 |
| 377 | zwf | None | pCASCADE-zwf-pykA-pykF | pCDF-nox | | 0 |
| 378 | gltA, zwf, pykA, pykF | ΔdhaL | pCASCADE-gltA2-zwf-pykA-pykF | pCDF-nox | 3.492333 | 3.415342 |
| 379 | gltA, zwf, pykA, pykF | Δepd | pCASCADE-gltA2-zwf-pykA-pykF | pCDF-nox | 4.262333 | 3.280439 |
| 380 | gltA, zwf, pykA, pykF | ΔptsA | pCASCADE-gltA2-zwf-pykA-pykF | pCDF-nox | 3.902 | 3.753735 |
| 381 | gltA, zwf, pykA, pykF | ΔmgsA | pCASCADE-gltA2-zwf-pykA-pykF | pCDF-nox | 3.657667 | 3.569623 |
| 382 | gltA, zwf, pykA, pykF | Δeda | pCASCADE-gltA2-zwf-pykA-pykF | pCDF-nox | 3.542 | 3.76073 |
| 383 | gltA, zwf, pykA, pykF | ΔdhaL, ΔptsA | pCASCADE-gltA2-zwf-pykA-pykF | pCDF-nox | 3.966333 | 3.411112 |
| 384 | gltA, zwf, pykA, pykF | ΔdhaL, ΔmgsA | pCASCADE-gltA2-zwf-pykA-pykF | pCDF-nox | 3.551667 | 3.371653 |

TABLE 1-continued

Pyruvate Production in MicroFermentations by engineered strains of *E. coli*.

| Strain # | Genes with Proteolysis Tags | Chromosomal Gene Deletions | Gene Silencing | NADH Oxidase Expression Vector | 24 hour Pryuvate Titer (g/L) | 24 Hour Normalized Pyruvate Titer (g/L- |
|---|---|---|---|---|---|---|
| 385 | gltA, zwf, pykA, pykF | Δepd, ΔptsA | pCASCADE-gltA2-zwf-pykA-pykF | pCDF-nox | 3.804667 | 3.356804 |
| 386 | gltA, zwf, pykA, pykF | Δepd, ΔmgsA | pCASCADE-gltA2-zwf-pykA-pykF | pCDF-nox | 3.742333 | 3.491614 |
| 387 | gltA, zwf, pykA, pykF | Δepd, Δeda | pCASCADE-gltA2-zwf-pykA-pykF | pCDF-nox | 3.356333 | 3.354152 |
| 388 | gltA, zwf, pykA, pykF | ΔmgsA, ΔptsA | pCASCADE-gltA2-zwf-pykA-pykF | pCDF-nox | 3.457 | 3.303145 |
| 389 | gltA, zwf, pykA, pykF | ΔptsA, Δeda | pCASCADE-gltA2-zwf-pykA-pykF | pCDF-nox | 4.002 | 3.158236 |
| 390 | gltA, zwf, pykA, pykF | ΔmgsA, Δeda | pCASCADE-gltA2-zwf-pykA-pykF | pCDF-nox | 3.788 | 3.836733 |
| 391 | gltA, zwf, pykA, pykF | ΔdhaL, Δepd, ΔptsA | pCASCADE-gltA2-zwf-pykA-pykF | pCDF-nox | 3.559667 | 3.613042 |
| 392 | gltA, zwf, pykA, pykF | ΔdhaL, Δepd, ΔmgsΔ_0% | pCASCADE-gltA2-zwf-pykA-pykF | pCDF-nox | 4.545333 | 2.131413 |
| 393 | gltA, zwf, pykA, pykF | ΔdhaL, Δepd, Δeda | pCASCADE-gltA2-zwf-pykA-pykF | pCDF-nox | 3.779 | 3.88175 |
| 394 | gltA, zwf, pykA, pykF | ΔdhaL, ΔmgsA, ΔptsA | pCASCADE-gltA2-zwf-pykA-pykF | pCDF-nox | 3.673 | 3.374992 |
| 395 | gltA, zwf, pykA, pykF | ΔdhaL, ΔptsA, Δeda | pCASCADE-gltA2-zwf-pykA-pykF | pCDF-nox | 4.133 | 3.408303 |
| 396 | gltA, zwf, pykA, pykF | ΔdhaL, ΔmgsA, Δeda | pCASCADE-gltA2-zwf-pykA-pykF | pCDF-nox | 3.637 | 2.858076 |
| 397 | gltA, zwf, pykA, pykF | Δepd, ΔmgsA, ΔptsA | pCASCADE-gltA2-zwf-pykA-pykF | pCDF-nox | 3.959667 | 3.664137 |
| 398 | gltA, zwf, pykA, pykF | Δepd, ΔptsA, Δeda | pCASCADE-gltA2-zwf-pykA-pykF | pCDF-nox | 4.402333 | 3.479784 |
| 399 | gltA, zwf, pykA, pykF | Δepd, ΔmgsA, Δeda | pCASCADE-gltA2-zwf-pykA-pykF | pCDF-nox | 3.770333 | 3.760646 |
| 400 | gltA, zwf, pykA, pykF | ΔptsA, ΔmgsA, Δeda | pCASCADE-gltA2-zwf-pykA-pykF | pCDF-nox | 3.573667 | 3.245052 |
| 401 | gltA, zwf, pykA, pykF | ΔdhaL, Δepd, ΔmgsA, ΔptsA | pCASCADE-gltA2-zwf-pykA-pykF | pCDF-nox | 3.398667 | 3.787656 |
| 402 | gltA, zwf, pykA, pykF | ΔdhaL, ΔmgsA, ΔptsA, Δeda | pCASCADE-gltA2-zwf-pykA-pykF | pCDF-nox | 3.482333 | 2.642224 |

Example 2: Production of Pyruvate in Fermentations Using Engineered *E. coli* Strain DLF_01542 Containing Plasmids pCASCADE-gltA2-Zf-pykA-pykF and pCDF-Nox

Figure 2:
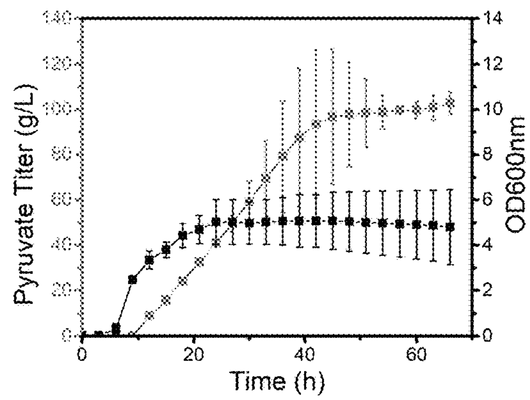
FIG. 2 depicts the production of pyruvate at the L fermentation scale in *E. coli* strain DLF 01542. (Genotype: (F−, Δ(araD-araB)567, ΔlacZ4787(::rrnB-3), rph-1, Δ(rhaD-rhaB)568, hsdR514, ΔldhA::frt, ΔpoxB::frt, ΔpflB::frt, ΔackA-pta::frt, ΔadhE::frt, ΔiclR, ΔarcA, ΔsspB, Δcas3::ugpBp-sspB-proB, lpd-DAS+4, gltA-DAS+4, zwf-DAS+4, pykA-DAS+4, pykF-DAS+4) containing plasmids pCASCADE-gltA2-zf-pykA-pykF and pCDF-nox. Biomass and pyruvate titers are plotted as a function of time.

*E. coli* strain DLF 01542 (Genotype: (F−, $\lambda^-$, Δ(araD-araB)567, ΔlacZ4787(:rrnB-3), rph-1, Δ(rhaD-rhaB)568, hsdR514, ΔldhA::frt, ΔpoxB::frt, ΔpflB::frt, ΔackA-pta::frt, ΔadhE::frt, ΔiclR, ΔarcA, ΔsspB, Δcas3::ugpBp-sspB-proB, lpd-DAS+4, gltA-DAS+4, zwf-DAS+4, pykA-DAS+4, pykF-DAS+4) containing plasmids pCASCADE-gltA2-zf-pykA-pykF and pCDF-nox, was used to produce pyruvate in fully instrumented lab scale fermentations (Refer to Common Methods Section for methods). Biomass levels and pyruvate were measured as a function of time. Pyruvate was quantified using UPLC (Refer to Common Methods Section). Results are given in FIG. 2.

Example 3: Purification of Pyruvic Acid and Salts Thereof from Fermentation Broth There are several well known methods for the purification of pyruvic acid and or its salts from aqueous broth. First broth may be clarified (removal of cells) by either centrifugation or filtration, such as ultrafiltration. Following clarification additional purification may include ion exchange chromatography (U.S. Pat. No. 4,918,013), such as a weakly-basic anion-exchange resin, which adsorbs the pyruvate anion. After rinsing out contaminants, the pyruvate can be eluted with a strong mineral acid such as sulfuric or hydrochloric acid (Japanese patent H06345683A). Alternatively, pyruvate in its acid form can be extracted into ether, the ether removed by vacuum evaporation and subsequently crystalized by addition of a miscible liquid. (U.S. Pat. No. 3,993,543). Yet another alternative purification involves complex-formation extraction using Tri-n-octanylamine (TOA) as an extractant. (Ma, C. Q., Li, J. C., Qiu, J. H., Wang, M., & Xu, P. (2005). *Recovery of pyruvic acid from biotransformation solutions. Applied Microbiology and Biotechnology,* 70(3), 308-314. doi:10.1007/s00253-005-0072-0).

Example 4: Production of Pyruvate Salts

Salts of pyruvate can be produced from clarified broth by extraction into an organic ester solvent such as tributyl phosphate, and then removed by addition of base to produce the metal pyruvate salts, which can be back-extraction into aqueous solution. (Chinese patent CN1103331C). Specifically, the addition of sodium hydroxide would lead to production of sodium pyruvate, the addition of magnesium hydroxide would lead to production of magnesium pyruvate, the addition of potassium hydroxide would lead to production of potassium pyruvate, addition of calcium hydroxide would lead to production of calcium pyruvate, and the addition of alternative hydroxides would lead to production of additional salts of pyruvate.

Example 5: Conversion of Pyruvic Acid to Pyruvic Acid Esters

Pyruvic acid, once produced, may be converted to the corresponding ester by reaction with an alcohol. For example, the addition of methanol to a mixture of pyruvic acid in the presence of an acid catalyst will result in the production of methyl pyruvate. As another example, the addition of ethanol to a mixture of pyruvic acid in the presence of an acid catalyst will result in the production of ethyl pyruvate. For example, Japanese Patent JPH1180088A teaches a method for the production of ethyl pyruvate by adding ethanol to pyruvic acid and heating in the presence of an acid catalyst. Since water reduces the yield of the reaction, 1,2-dichloroethane is added to enhance water removal. One skilled in the art may conduct this reaction with any alcohol and suitable catalyst to produce pyruvic acid esters Esters of pyruvate may include for example polyol-pyruvate esters, pyruvate thioesters, glycerol-pyruvate esters or dihydroxyacetone-pyruvate esters. In vitro, a Fisher or Fischer-Speier esterification may be performed to produce a pyruvate ester from pyruvate. Methods of preparing a pyruvate ester by oxidation with hydrogen peroxide in the presence of a Ti—Si catalyst have been described (U.S. Pat. No. 8,877,959; and Lopalco et al "Mechanism of Decarboxylation of pyruvic acid in the presence of hydrogen peroxide" J. Pharm Sci 2016 February; 105(2): 705-713. Doi:10.1002/jps.24653). Preparation of other pyruvate thiolesters has also been described (U.S. Pat. No. 5,968,727).

Common Methods Section

All methods in this Section are provided for incorporation into the Examples where so referenced. The names and city addresses of major suppliers are provided herein.

Subsection I. Microorganism Species and Strains, Cultures, and Growth Media

Microbial species, that may be used as needed, are as follows: *Escherichia coli* strain BW25113 is obtained from the Yale Genetic Stock Center (www.cgsc.biology.yale.edu) and is obtained as an actively growing culture. Serial dilutions of the actively growing *E. coli* K12 culture are made into Luria Broth (RPI Corp, Mt. Prospect, Ill., USA) and are allowed to grow for aerobically for 24 hours at 37° C. at 250 rpm until saturated..

*Escherichia coli* strain BWapldf was a generous gift from George Chen from Tsinghua University in China. Serial dilutions of the actively growing *E. coli* BWapldf is culture are made into Luria Broth (RPI Corp, Mt. Prospect, Ill., USA) and are allowed to grow for aerobically for 24 hours at 37° C. at 250 rpm until saturated.

Unless otherwise stated, all materials and reagents were of the highest grade possible and purchased from Sigma (St. Louis, Mo.). C13 labeled Alanine (2,3-13C2, 99%) (Item #CLM-2734-PK) was purchased from Cambridge Isotope Laboratories, Inc. (Tewksbury, Mass.). Luria Broth was used for routine strain and plasmid propagation and construction. Working antibiotic concentrations were as follows: ampicillin (100 μg/mL), kanamycin (35 μg/mL), chloramphenicol (35 μg/mL), spectinomycin (100 μg/mL), zeocin (50 μg/mL), gentamicin (10 μg/mL), blasticidin (100 μg/mL), puromycin (150 μg/mL), tetracycline (5 μg/mL). Luria broth with low salt (Lennox formulation) was used to select for zeocin, blasticidin and puromycin resistant clones. In addition, for puromycin selection, phosphate buffer (pH=8.0) was added to LB Lennox to a final concentration of 50 mM. Media formulations including stock solutions are described in the Tables below.

Stock Solutions are prepared as follows.

10× concentrated Ammonium-Citrate 30 salts (1 L), mix 30 g of $(NH_4)_2SO_4$ and 1.5 g citric acid in water with stirring, adjust pH to 7.5 with 10 M NaOH. Autoclave and store at room temperature (RT).

10× concentrated Ammonium-Citrate 90 salts (1 L), mix 90 g of $(NH_4)_2SO_4$ and 2.5 g citric acid in water with stirring, adjust pH to 7.5 with 10 M NaOH. Autoclave and store at RT.

10× concentrated Ammonium-Citrate 90 salts (1 L), mix 90 g of $(NH_4)_2SO_4$ and 2.5 g citric acid in water with stirring, adjust pH to 7.5 with 10 M NaOH. Autoclave and store at RT.

1 M Potassium 3-(N-morpholino) propanesulfonic Acid (MOPS), adjust to pH 7.4 with 50% KOH. Filter sterilize (0.2 μm) and store at RT.

0.5 M potassium phosphate buffer, pH 6.8, mix 248.5 mL of 1.0 M $K_2HPO_4$ and 251.5 mL of 1.0 M $KH_2PO_4$ and adjust to a final volume of 1000 mL with ultrapure water. Filter sterilize (0.2 μm) and store at RT.

2 M $MgSO_4$ and 10 mM $CaSO_4$ solutions. Filter sterilize (0.2 μm) and store at RT.

50 g/L solution of thiamine-HCl. Filter sterilize (0.2 μm) and store at 4° C.

500 g/L solution of glucose, dissolve by stirring with heat. Cool, filter sterilize (0.2 μm), and store at RT.

100 g/L yeast extract, autoclave, and store at RT.

100 g/L casamino acid, autoclave, and store at RT.

500× Trace Metal Stock: Prepare a solution of micronutrients in 1000 mL of water containing 10 mL of concentrated $H_2SO_4$. 0.6 g $CoSO_4.7H_2O$, 5.0 g $CuSO_4.5H_2O$, 0.6 g $ZnSO_4.H_2O$, 0.2 g $Na_2MoO_4.2H_2O$, 0.1 g $H_3BO_3$, and 0.3 g $MnSO_4.H_2O$. Filter sterilize (0.2 nm) and store at RT in the dark.

Prepare a fresh solution of 40 mM ferric sulfate heptahydrate in water, filter sterilize (0.2 μm) before preparing media each time.

TABLE CM1

| Seed Media, pH 6.8: | | | |
|---|---|---|---|
| Ingredient | Unit | SM10 | SM10++ |
| $(NH_4)_2SO_4$ | g/L | 9 | 9 |
| Citric Acid | g/L | 0.25 | 0.25 |
| Potassium Phosphate | mM | 5 | 5 |
| $CoSO_4 \cdot 7H_2O$ | g/L | 0.0048 | 0.0048 |
| $CuSO_4 \cdot 5H_2O$ | g/L | 0.04 | 0.04 |
| $ZnSO_4 \cdot H_2O$ | g/L | 0.0048 | 0.0048 |
| $Na_2MoO_4 \cdot 2H_2O$ | g/L | 0.0016 | 0.0016 |
| $H_3BO_3$ | g/L | 0.0008 | 0.0008 |
| $MnSO_4 \cdot H_2O$ | g/L | 0.0024 | 0.0024 |
| $FeSO_4 \cdot 7H_2O$ | g/L | 0.044 | 0.044 |
| $MgSO_4$ | mM | 2.5 | 2.5 |
| $CaSO_4$ | mM | 0.06 | 0.06 |
| Glucose | g/L | 45 | 45 |
| MOPS | mM | 200 | 200 |
| Thiamine-HCl | g/L | 0.01 | 0.01 |
| Yeast Extract | g/L | 1 | 2.5 |
| Casamino Acids | g/L | 0 | 2.5 |

TABLE CM2

| Production/Wash Media, pH 6.8: | | | | | | |
|---|---|---|---|---|---|---|
| Ingredient | Unit | FGM3 | FGM3 No Phosphate | FGM3 Wash | FGM3 + 40 mM phosphate | FGM10 |
| $(NH_4)_2SO_4$ | g/L | 3 | 3 | 3 | 3 | 9 |
| Citric Acid | g/L | 0.15 | 0.15 | 0.15 | 0.15 | 0.25 |
| Potassium Phosphate | mM | 1.8 | 0 | 0 | 40 | 5 |
| $CoSO_4$•$7H_2O$ | g/L | 0.0024 | 0.0024 | 0 | 0.0024 | 0.0048 |
| $CuSO_4$•$5H_2O$ | g/L | 0.02 | 0.02 | 0.00 | 0.02 | 0.04 |
| $ZnSO_4$•$H_2O$ | g/L | 0.0024 | 0.0024 | 0 | 0.0024 | 0.0048 |
| $Na_2MoO_4$•$2H_2O$ | g/L | 0.0008 | 0.0008 | 0 | 0.0008 | 0.0016 |
| $H_3BO_3$ | g/L | 0.0004 | 0.0004 | 0 | 0.0004 | 0.0008 |
| $MnSO_4$•$H_2O$ | g/L | 0.0012 | 0.0012 | 0 | 0.0012 | 0.0024 |
| $FeSO_4$•$7H_2O$ | g/L | 0.022 | 0.022 | 0 | 0.022 | 0.044 |
| $MgSO_4$ | mM | 2 | 2 | 0 | 2 | 2.5 |
| $CaSO_4$ | mM | 0.05 | 0.05 | 0 | 0.05 | 0.06 |
| Glucose | g/L | 45 | 25 | 0 | 45 | 25 |
| MOPS | mM | 200 | 200 | 0 | 200 | 0 |
| Thiamine-HCl | g/L | 0.01 | 0.01 | 0 | 0.01 | 0.01 |

TABLE CM3

| Fermentation Media, pH 6.8: | | | | |
|---|---|---|---|---|
| Ingredient | FLNM10 | FLNM10_S | FLNM10_P | Unit |
| NH4Cl | 2 | 2 | 2.486 | g/L |
| Citric Acid | 1.7 | 1.7 | 1.7 | g/L |
| (NH4)2HPO4 | 1 | 1 | 0.4 | g/L |
| CoSO4•7H2O | 0.002 | 0.002 | 0.002 | g/L |
| CuSO4•5H2O | 0.002 | 0.002 | 0.002 | g/L |
| ZnSO4•7H2O | 0.0137 | 0.0137 | 0.0137 | g/L |
| Na2MoO4•2H2O | 0.012 | 0.012 | 0.012 | g/L |
| H3BO3 | 0.003 | 0.003 | 0.003 | g/L |
| MnSO4•H2O | 0.0038 | 0.0038 | 0.0038 | g/L |
| FeSO4•7H2O | 0.3 | 0.3 | 0.3 | g/L |
| MgSO4 7H2O | 1.4 | 1.4 | 1.4 | g/L |
| CaCl2 2H2O | 0.02 | 0.02 | 0.02 | g/L |
| glucose | 25 | 25 | 25 | g/L |
| Thiamine-HCl | 0.01 | 0.01 | 0.01 | g/L |
| H2SO4 | | 0.384 | | mL |

Subsection II. Strain Construction

Oligonucleotides and synthetic linear DNA (G-Blocks™) used for strain construction and confirmation are all given in Tables CM4-CM8 below. and they were obtained from Integrated DNA Technologies (IDT, Coralville, Iowa). Strain BW25113 was obtained from the Yale Genetic Stock Center (CGSC http://cgsc.biology.yale.edu/). Strain BWapldf was a kind gift from George Chen (Tsinghua University). Chromosomal modifications were made using standard recombineering methodologies either with direct antibiotic cassette integration in the case of C-terminal DAS+4 tags carrying antibiotic resistance cassettes, or through scarless tet-sacB selection and counterselection. The recombineering plasmid pSIM5 and the tet-sacB selection/counterselection marker cassette were kind gifts from Donald Court (NCI, https://redrecombineering.ncifcrf.gov/court-lab.html). Briefly, the tet-sacB selection/counterselection cassette was amplified using the appropriate oligos supplying ~50 bp flanking homology sequences using Econotaq (Lucigen Middleton, Wis.) according to manufacturer's instructions, with an initial 10 minutes denaturation at 94° C., followed by 35 cycles of 94° C., for 15 seconds, 52° C. for 15 seconds, and 72° C. for 5 minutes. Cassettes used for "curing" of the tet-sacB cassette or direct integration (when an antibiotic marker is present) were obtained as G-Blocks™ from IDT. In the case of the sspB gene deletion, the open reading frame deletion replaced with a kanamycin resistance was amplified from the Keio Collection strain, JW3197-1 (the keio Collection), and moved to the appropriate background strain using standard methodologies. The kanamycin resistance cassette was cured using the pCP20 plasmid, leaving an frt scar. Chromosomal modifications were confirmed by PCR amplification and sequencing (Eton Biosciences) using paired oligonucleotides, either flanking the entire region, or in the case of DAS+4 tag insertions an oligo 5' of the insertion and one internal to the resistance cassette. Oligos and DNA sequences for DAS+4 tagging and tet-secB based genome engineering are given in Tables CM4 and CM5.

TABLE CM4

| Oligonucleotides used for strain construction. | | |
|---|---|---|
| Oligo | Sequence | SEQ ID NO |
| ilcR_tetA_F | TAACAATAAAAATGAAAATGATTTCCACGATACAGAAAAAAGAGACTG TCATCCTAATTTTTGTTGACACTCTATC | 1 |
| ilcR_sacB_R | TGCCACTCAGGTATGATGGGCAGAATATTGCCTCTGCCCGCCAGAAAAA GATCAAAGGGAAAACTGTCCATATGC | 2 |
| iclR_500up | CCGACAGGGATTCCATCTG | 3 |
| iclR_500dn | TATGACGACCATTTTGTCTACAGTTC | 4 |
| arcA_tetA_F | GGACTTTTGTACTTCCTGTTTCGATTTAGTTGGCAATTTAGGTAGCAAAC TCCTAATTTTTGTTGACACTCTATC | 5 |

TABLE CM4-continued

Oligonucleotides used for strain construction.

| Oligo | Sequence | SEQ ID NO |
|---|---|---|
| arcA_sacB_R | ATAAAAACGGCGCTAAAAAGCGCCGTTTTTTTTGACGGTGGTAAAGCCG AATCAAAGGGAAAACTGTCCATATGC | 6 |
| arcA_500up | CCTGACTGTACTAACGGTTGAG | 7 |
| arcA_500dn | TGACTTTTATGGCGTTCTTTGTTTTTG | 8 |
| sspB_kan_F | CTGGTACACGCTGATGAACACC | 9 |
| sspB_kan_R | CTGGTCATTGCCATTTGTGCC | 10 |
| sspB_conf_F | GAATCAGAGCGTTCCGACCC | 11 |
| sspB_conf_R | GTACGCAGTTTGCCAACGTG | 12 |
| cas3_tetA_F | AATAGCCCGCTGATATCATCGATAATACTAAAAAAACAGGGAGGCTAT TATCCTAATTTTTGTTGACACTCTATC | 13 |
| cas3_sacB_R | TACAGGGATCCAGTTATCAATAAGCAAATTCATTTGTTCTCCTTCATATG ATCAAAGGGAAAACTGTCCATATGC | 14 |
| cas3_conf_F | CAAGACATGTGTATATCACTGTAATTC | 15 |
| cas3_500dn | GCGATTGCAGATTTATGATTTGG | 16 |
| gltA_conf_F | TATCATCCTGAAAGCGATGG | 17 |
| lpd_conf_F | ATCTCACCGTGTGATCGG | 18 |
| udhA_conf_F | CAAAAGAGATTCTGGGTATTCACT | 19 |
| zwf_conf_F | CTGCTGGAAACCATGCG | 20 |
| zwf_500dn | AGAGCATGTCGTTATAGGAGGTGAT | 21 |
| ampR_intR | AGTACTCAACCAAGTCATTCTG | 22 |
| bsdR_intR | GAGCATGGTGATCTTCTCAGT | 23 |
| gentR_intR | GCGATGAATGTCTTACTACGGA | 24 |
| purR_intR | GTCGCTGGGTAATCTGCAA | 25 |
| tetA_intR | ATCAACGCATATAGCGCTAGCAG | 26 |
| zeoR_intR | ACTGAAGCCCAGACGATC | 27 |
| tetR_intR | ATCAACGCATATAGCGCTAGCAG | 28 |
| specR_intR | CACTGTGTGGCTTCAGGC | 29 |
| ampR_intR | AGTACTCAACCAAGTCATTCTG | 30 |
| purR_intR | GTCGCTGGGTAATCTGCAA | 31 |
| PykA-FOR1 | CCTGACTGCTCTCTATCG | 32 |
| PykA-FOR2 | CGAAGCGGTTAATCTGCTG | 33 |
| PykF-FOR1 | CGGCTCATCAGTTGGTACTG | 34 |
| PykF-FOR2 | GGGTAAAGAACTGGCTCTGC | 35 |

TABLE CM5

| Synthetic DNA used for strain construction. |
|---|
| tetA-sacB Cassette SEQ ID NO 36<br>TCCTAATTTTTGTTGACACTCTATCATTGATAGAGTTATTTTACCACTCCCTATCAGTGATAGAGAA<br>AAGTGAAATGAATAGTTCGACAAAGATCGCATTGGTAATTACGTTACTCGATGCCATGGGGATTG<br>GCCTTATCATGCCAGTCTTGCCAACGTTATTACGTGAATTTATTGCTTCGGAAGATATCGCTAACC |

TABLE CM5-continued

| Synthetic DNA used for strain construction. |
|---|
| ACTTTGGCGTATTGCTTGCACTTTATGCGTTAATGCAGGTTATCTTTGCTCCTTGGCTTGGAAAAAT GTCTGACCGATTTGGTCGGCGCCCAGTGCTGTTGTTGTCATTAATAGGCGCATCGCTGGATTACTT ATTGCTGGCTTTTTCAAGTGCGCTTTGGATGCTGTATTTAGGCCGTTTGCTTTCAGGGATCACAGGA GCTACTGGGGCTGTCGCGGCATCGGTCATTGCCGATACCACCTCAGCTTCTCAACGCGTGAAGTGG TTCGGTTGGTTAGGGGCAAGTTTTGGGCTTGGTTTAATAGCGGGGCCTATTATTGGTGGTTTTGCA GGAGAGATTTCACCGCATAGTCCCTTTTTTATCGCTGCGTTGCTAAATATTGTCACTTTCCTTGTGG TTATGTTTTGGTTCCGTGAAACCAAAAATACACGTGATAATACAGATACCGAAGTAGGGGTTGAG ACGCAATCGAATTCGGTATACATCACTTTATTTAAAACGATGCCCATTTTGTTGATTATTTATTTTT CAGCGCAATTGATAGGCCAAATTCCCGCAACGGTGTGGGTGCTATTTACCGAAAATCGTTTTGGAT GGAATAGCATGATGGTTGGCTTTTCATTAGCGGGTCTTGGTCTTTTACACTCAGTATTCCAAGCCTT TGTGGCAGGAAGAATAGCCACTAAATGGGGCGAAAAAACGGCAGTACTGCTCGGATTTATTGCAG ATAGTAGTGCATTTGCCTTTTTAGCGTTTATATCTGAAGGTTGGTTAGTTTTCCCTGTTTTAATTTTA TTGGCTGGTGGTGGGATCGCTTTACCTGCATTACAGGGAGTGATGTCTATCCAAACAAAGAGTCAT CAGCAAGGTGCTTTACAGGGATTATTGGTGAGCCTTACCAATGCAACCGGTGTTATTGGCCCATTA CTGTTTGCTGTTATTTATAATCATTCACTACCAATTTGGGATGGCTGGATTTGGATTATTGGTTTAG CGTTTTACTGTATTATTATCCTGCTATCGATGACCTTCATGTTAACCCCTCAAGCTCAGGGGAGTAA ACAGGAGACAAGTGCTTAGTTATTTCGTCACCAAATGATGTTATTCCGCGAAATATAATGACCCTC TTGATAACCCAAGAGCATCACATATACCTGCCGTTCACTATTATTTAGTGAAATGAGATATTATGA TATTTTCTGAATTGTGATTAAAAAGGCAACTTTATGCCCATGCAACAGAAACTATAAAAAATACAG AGAATGAAAAGAAACAGATAGATTTTTTAGTTCTTTAGGCCCGTAGTCTGCAAATCCTTTTATGAT TTTCTATCAAACAAAAGAGGAAAATAGACCAGTTGCAATCCAAACGAGAGTCTAATAGAATGAGG TCGAAAAGTAAATCGCGCGGGTTTGTTACTGATAAAGCAGGCAAGACCTAAAATGTGTAAAGGGC AAAGTGTATACTTTGGCGTCACCCCTTACATATTTTAGGTCTTTTTTTATTGTGCGTAACTAACTTG CCATCTTCAAACAGGAGGGCTGGAAGAAGCAGACCGCTAACACAGTACATAAAAAAGGAGACAT GAACGATGAACATCAAAAAGTTTGCAAAACAAGCAACAGTATTAACCTTTACTACCGCACTGCTG GCAGGAGGCGCAACTCAAGCGTTTGCGAAAGAAACGAACCAAAAGCCATATAAGGAAACATACG GCATTTCCCATATTACACGCCATGATATGCTGCAAATCCCTGAACAGCAAAAAAATGAAAAATAT CAAGTTCCTGAGTTCGATTCGTCCACAATTAAAAATATCTCTTCTGCAAAAGGCCTGGACGTTTGG GACAGCTGGCCATTACAAAACGCTGACGGCACTGTCGCAAACTATCACGGCTACCACATCGTCTTT GCATTAGCCGGAGATCCTAAAAATGCGGATGACACATCGATTTACATGTTCTATCAAAAAGTCGG CGAAACTTCTATTGACAGCTGGAAAAACGCTGGCCGCGTCTTTAAAGACAGCGACAAATTCGATG CAAATGATTCTATCCTAAAAGACCAAACACAAGAATGGTCAGGTTCAGCCACATTTACATCTGAC GGAAAAATCCGTTTATTCTACACTGATTTCTCCGGTAAACATTACGGCAAACAAACACTGACAACT GCACAAGTTAACGTATCAGCATCAGACAGCTCTTTGAACATCAACGGTGTAGAGGATTATAAATC AATCTTTGACGGTGACGGAAAAACGTATCAAAATGTACAGCAGTTCATCGATGAAGGCAACTACA GCTCAGGCGACAACCATACGCTGAGAGATCCTCACTACGTAGAAGATAAAGGCCACAAATACTTA GTATTTGAAGCAAACACTGGAACTGAAGATGGCTACCAAGGCGAAGAATCTTTATTTAACAAAGC ATACTATGGCAAAAGCACATCATTCTTCCGTCAAGAAAGTCAAAAACTTCTGCAAAGCGATAAAA AACGCACGGCTGAGTTAGCAAACGGCGCTCTCGGTATGATTGAGCTAAACGATGATTACACACTG AAAAAAGTGATGAAACCGCTGATTGCATCTAACACAGTAACAGATGAAATTGAACGCGCGAACGT CTTTAAAATGAACGGCAAATGGTACCTGTTCACTGACTCCCGCGGATCAAAAATGACGATTGACG GCATTACGTCTAACGATATTTACATGCTTGGTTATGTTTCTAATTCTTTAACTGGCCCATACAAGCC GCTGAACAAAACTGGCCTTGTGTTAAAAATGGATCTTGATCCTAACGATGTAACCTTTACTTACTC ACACTTCGCTGTACCTCAAGCGAAAGGAAACAATGTCGTGATTACAAGCTATATGACAAACAGAG GATTCTACGCAGACAAACAATCAACGTTTGCGCCAAGCTTCCTGCTGAACATCAAAGGCAAGAAA ACATCTGTTGTCAAAGACAGCATCCTTGAACAAGGACAATTAACAGTTAACAAATAAAAACGCAA AAGAAAATGCCGATATTGACTACCGGAAGCAGTGTGACCGTGTGCTTCTCAAATGCCTGATTCAG GCTGTCTATGTGTGACTGTTGAGCTGTAACAAGTTGTCTCAGGTGTTCAATTTCATGTTCTAGTTGC TTTGTTTTACTGGTTTCACCTGTTCTATTAGGTGTTACATGCTGTTCATCTGTTACATTGTCGATCTG TTCATGGTGAACAGCTTTAAATGCACCAAAAACTCGTAAAAGCTCTGATGTATCTATCTTTTTTAC ACCGTTTTCATCTGTGCATATGGACAGTTTTCCCTTTGAT |
| ΔiclR-cure SEQ ID NO 37<br>AAATGATTTCCACGATACAGAAAAAAGAGACTGTCATGGGCAGAATATTGCCTCTGCCCGCCAGA AAAAG |
| ΔarcA-cure SEQ ID NO 38<br>CTGTTTCGATTTAGTTGGCAATTTAGGTAGCAAACTCGGCTTTACCACCGTCAAAAAAAACGGCGC TTTT |
| Δcas3::ugBp-sspB-pro-casA SEQ ID NO 39<br>CAAGACATGTGTATATCACTGTAATTCGATATTTATGAGCAGCATCGAAAAATAGCCCGCTGATAT CATCGATAATACTAAAAAAACAGGGAGGCTATTACCAGGCATCAAATAAAACGAAAGGCTCAGTC GAAAGACTGGGCCTTTCGTTTTATCTGTTGTTTGTCGGTGAACGCTCTCTACTAGAGTCACACTGGC TCACCTTCGGGTGGGCCTTTCTGCGTTTATATCTTTCTGACACCTTACTATCTTACAAATGTAACAA AAAAGTTATTTTTCTGTAATTCGAGCATGTCATGTTACCCCGCGAGCATAAAACGCGTGTGTAGGA GGATAATCTATGGATTTGTCACAGCTAACACCACGTCGTCCCTATCTGCTGCGTGCATTCTATGAG TGGTTGCTGGATAACCAGCTCACGCCGCACCTGGTGGTGGATGTGACGCTCCCTGGCGTGCAGGTT CCTATGGAATATGCGCGTGACGGGCAAATCGTACTCAACATTGCGCCGCGTGCTGTCGGCAATCTG GAACTGGCGAATGATGAGGTGCGCTTTAACGCGCGCTTTGGTGGCATTCCGCGTCAGGTTTCTGTG CCGCTGGCTGCCGTGCTGGCTATCTACGCCCGTGAAAATGGCGCAGGCACGATGTTTGAGCCTGA AGCTGCCTACGATGAAGATACCAGCATCATGAATGATGAAGAGGCATCGGCAGACAACGAAACC GTTATGTCGGTTATTGATGGCGACAAGCCAGATCACGATGATGACACTCATCCTGACGATGAACCT CCGCAGCCACCACGCGGTGGTCGACCGGCATTACGCGTTGTGAAGTAATTGACGGCTAGCTCAGT CCTAGGTACAGTGCTAGCCATATGAAGGAGAACAAATGAATTTGCTTATTGATAACTGGATCCCTG TACGCCCGCGAAACGGGGGGAAAGTCCAAATCATAAATCTGCAATCGCTATAC |

TABLE CM5-continued

| Synthetic DNA used for strain construction. |
| --- |

gltA-DAS + 4-ampR SEQ ID NO 40
GTATTCCGTCTTCCATGTTCACCGTCATTTTCGCAATGGCACGTACCGTTGGCTGGATCGCCCACTG
GAGCGAAATGCACAGTGACGGTATGAAGATTGCCCGTCCGCGTCAGCTGTATACAGGATATGAAA
AACGCGACTTTAAAAGCGATATCAAGCGTGCGGCCAACGATGAAAACTATTCTGAAAACTATGCG
GATGCGTCTTAATAGTCCTGACGGATGGCCTTTTTGCGTTTCTACAAACTCTTTTTGTTTATTTTTCT
AAATACATTCAAATATGTATCCGCTCATGAGACAATAACCCTGATAAATGCTTCAATAATATTGAA
AAAGGAAGAGTATGAGTATTCAACATTTCCGTGTCGCCCTTATTCCCTTTTTTGCGGCATTTTGCCT
TCCTGTTTTTGCTCACCCAGAAACGCTGGTGAAAGTAAAAGATGCTGAAGATCAGTTGGGTGCAC
GAGTGGGTTACATCGAACTGGATCTCAACAGCGGTAAGATCCTTGAGAGTTTTCGCCCCGAAGAA
CGTTTTCCAATGATGAGCACTTTTAAAGTTCTGCTATGTGGCGCGGTATTATCCCGTGTTGACGCCG
GGCAAGAGCAACTCGGTCGCCGCATACACTATTCTCAGAATGACTTGGTTGAGTACTCACCAGTCA
CAGAAAAGCATCTTACGGATGGCATGACAGTAAGAGAATTATGCAGTGCTGCCATAACCATGAGT
GATAACACTGCGGCCAACTTACTTCTGACAACGATCGGAGGACCGAAGGAGCTAACCGCTTTTTT
GCACAACATGGGGGATCATGTAACTCGCCTTGATCGTTGGGAACCGGAGCTGAATGAAGCCATAC
CAAACGACGAGCGTGACACCACGATGCCTACAGCAATGGCAACAACGTTGCGCAAACTATTAACT
GGCGAACTACTTACTCTAGCTTCCCGGCAACAATTAATAGACTGGATGGAGGCGGATAAAGTTGC
AGGACCACTTCTGCGCTCGGCCCTTCCGGCTGGCTGGTTTATTGCTGATAAATCTGGAGCCGGTGA
GCGTGGGTCTCGCGGTATCATTGCAGCACTGGGGCCAGATGGTAAGCCCTCCCGTATCGTAGTTAT
CTACACGACGGGGAGTCAGGCAACTATGGATGAACGAAATAGACAGATCGCTGAGATAGGTGCCT
CACTGATTAAGCATTGGTAACTGTCAGACTAATGGTTGATTGCTAAGTTGTAAATATTTTAACCCG
CCGTTCATATGGCGGGTTGATTTTTATATGCCTAAACACAAAAAATTGTAAAAATAAAATCCATTA
ACAGACCTATATAGATATTTAAAAAGAATAGAACAGCTCAAATTATCAGCAACCCAATACTTTCA
ATTAAAAACTTCATGGTAGTCGCATTTATAACCCTATGAAA gltA-DAS + 4-purR SEQ ID NO 41
ACCGTCATTTTCGCAATGGCACGTACCGTTGGCTGGATCGCCCACTGGAGCGAAATGCACAGTGA
CGGTATGAAGATTGCCCGTCCGCGTCAGCTGTATACAGGATATGAAAAACGCGACTTTAAAAGCG
ATATCAAGCGTGCGGCCAACGATGAAAACTATTCTGAAAACTATGCGGATGCGTCTTAATCCTGA
CGGATGGCCTTTTTGCGTTTCTACAAACTCTTTTTGTTTATTTTTCTAAATACATTCAAATATGTATC
CGCTCATGAGACAATAACCCTGATAAATGCTTCAATAATATTGAAAAAGGAAGAGTATGACTGAA
TACAAGCCCACGGTACGCTTGGCGACGCGCGACGATGTTCCCCGCGCTGTTCGTACATTAGCTGCG
GCCTTTGCAGATTACCCAGCGACGCGCCATACGGTCGATCCGGACCGCCATATCGAGCGTGTCAC
AGAATTGCAGGAACTTTTCTTAACTCGCGTGGGCCTTGACATCGGAAAGGTCTGGGTGGCTGACG
ATGGCGCTGCAGTGGCTGTTTGGACCACTCCGGAGAGTGTAGAGGCTGGTGCAGTGTTCGCCGAA
ATTGGTCCTCGTATGGCCGAATTAAGTGGAAGTCGTCTGGCAGCCCAACAACAAATGGAAGGGTT
GCTTGCGCCCCACCGTCCGAAAGAACCCGCGTGGTTCCTTGCCACCGTTGGAGTAAGCCCAGATC
ACCAGGGGAAGGGTTTAGGATCTGCCGTAGTTTTACCAGGTGTGGAGGCAGCAGAACGTGCGGGA
GTTCCGGCCTTCCTTGAGACGTCGGCGCCGCGCAATTTACCGTTTTACGAACGTCTTGGATTCACC
GTTACGGCGGACGTGGAGGTGCCGGAGGGACCCCGTACTTGGTGTATGACTCGTAAACCGGGAGC
CTGATAATGGTTGATTGCTAAGTTGTAAATATTTTAACCCGCCGTTCATATGGCGGGTTGATTTTTA
TATGCCTAAACACAAAAAATTGTAAAAATAAAATCCATTAACAGACCTATATAGATATTTAAAAA
GAATAGAACAGCTCAAATTATCAGCAACCCA gltA-DAS + 4-zeoR SEQ ID NO 42
GTATTCCGTCTTCCATGTTCACCGTCATTTTCGCAATGGCACGTACCGTTGGCTGGATCGCCCACTG
GAGCGAAATGCACAGTGACGGTATGAAGATTGCCCGTCCGCGTCAGCTGTATACAGGATATGAAA
AACGCGACTTTAAAAGCGATATCAAGCGTGCGGCCAACGATGAAAACTATTCTGAAAACTATGCG
GATGCGTCTTAATAGTTGACAATTAATCATCGGCATAGTATATCGGCATAGTATAATACGACTCAC
TATAGGAGGGCCATCATGGCCAAGTTGACCAGTGCCGTTCCGGTGCTCACCGCGCGCGACGTCGC
CGGAGCGGTCGAGTTCTGGACCGACCGGCTCGGGTTCTCCCGGGACTTCGTGGAGGACGACTTCG
CCGGTGTGGTCCGGGACGACGTGACCCTGTTCATCAGCGCGGTCCAGGACCAGGTGGTGCCGGAC
AACACCCTGGCCTGGGTGTGGGTGCGCGGCCTGGACGAGCTGTACGCCGAGTGGTCGGAGGTCGT
GTCCACGAACTTCCGGGACGCCTCCGGGCCGGCCATGACCGAGATCGGCGAGCAGCCGTGGGGGC
GGGAGTTCGCCCTGCGCGACCCGGCCGGCAACTGCGTGCACTTTGTGGCAGAGGAGCAGGACTGA
GGATAAGTAATGGTTGATTGCTAAGTTGTAAATATTTTAACCCGCCGTTCATATGGCGGGTTGATT
TTTATATGCCTAAACACAAAAAATTGTAAAAATAAAATCCATTAACAGACCTATATAGATATTTAA
AAAGAATAGAACAGCTCAAATTATCAGCAACCCAATACTTTCAATTAAAAACTTCATGGTAGTCG
CATTTATAACCCTATGAAA lpd-DAS + 4-gentR SEQ ID NO 43
GCGGCGAGCTGCTGGGTGAAATCGGCCTGGCAATCGAAATGGGTTGTGATGCTGAAGACATCGCA
CTGACCATCCACGCGCACCCGACTCTGCACGAGTCTGTGGGCCTGGCGGCAGAAGTGTTCGAAGG
TAGCATTACCGACCTGCCGAACCCGAAAGCGAAGAAGAAGGCGGCCAACGATGAAAACTATTCT
GAAAACTATGCGGATGCGTCTTAATAGCGAATCCATGTGGGAGTTTATTCTTGACACAGATATTTA
TGATATAATAACTGAGTAAGCTTAACATAAGGAGGAAAAACATATGTTACGCAGCAGCAACGATG
TTACGCAGCAGGGCAGTCGCCCTAAAACAAAGTTAGGTGGCTCAAGTATGGGCATCATTCGCACA
TGTAGGCTCGGCCCTGACCAAGTCAAATCCATGCGGGCTGCTCTTGATCTTTTCGGTCGTGAGTTC
GGAGACGTAGCCACCTACTCCCAACATCAGCCGGACTCCGATTACCTCGGGAACTTGCTCCGTAGT
AAGACATTCATCGCGCTTGCTGCCTTCGACCAAGAAGCGGTTGTTGGCGCTCTCGCGGCTTACGTT
CTGCCCAAGTTTGAGCAGCCGCGTAGTGAGATCTATATCTATGATCTCGCAGTCTCCGGCGAGCAC
CGGAGGCAGGGCATTGCCACCGCGCTCATCAATCTCCTCAAGCATGAGGCCAACGCGCTTGGTGC
TTATGTGATCTACGTGCAAGCAGATTACGGTGACGATCCCGCAGTGGCTCTCTATACAAAGTTGGG
CATACGGGAAGAAGTGATGCACTTTGATATCGACCCAAGTACCGCCACCTAATTTTTCGTTTGCCG
GAACATCCGGCAATTAAAAAAGCGGCTAACCACGCCGCTTTTTTTACGTCTGCAATTTACCTTTCC
AGTCTTCTTGCTCCACGTTCAGAGAGACGTTCGCATACTGCTGACCGTTGCTCGTTATTCAGCCTGA
CAGTATGGTTACTGTC TABLE CM5-continued

| Synthetic DNA used for strain construction. |
|---|
| zwf-DAS + 4-bsdR SEQ ID NO 44<br>GAAGTGGAAGAAGCCTGGAAATGGGTAGACTCCATTACTGAGGCGTGGGCGATGGACAATGATG<br>CGCCGAAACCGTATCAGGCCGGAACCTGGGGACCCGTTGCCTCGGTGGCGATGATTACCCGTGAT<br>GGTCGTTCCTGGAATGAGTTTGAGGCGGCCAACGATGAAAACTATTCTGAAAACTATGCGGATGC<br>GTCTTAATAGTTGACAATTAATCATCGGCATAGTATATCGGCATAGTATAATACGACTCACTATAG<br>GAGGGCCATCATGAAGACCTTCAACATCTCTCAGCAGGATCTGGAGCTGGTGGAGGTCGCCACTG<br>AGAAGATCACCATGCTCTATGAGGACAACAAGCACCATGTCGGGGCGGCCATCAGGACCAAGACT<br>GGGGAGATCATCTCTGCTGTCCACATTGAGGCCTACATTGGCAGGGTCACTGTCTGTGCTGAAGCC<br>ATTGCCATTGGGTCTGCTGTGAGCAACGGGCAGAAGGACTTTGACACCATTGTGGCTGTCAGGCA<br>CCCCTACTCTGATGAGGTGGACAGATCCATCAGGGTGGTCAGCCCCTGTGGCATGTGCAGAGAGC<br>TCATCTCTGACTATGCTCCTGACTGCTTTGTGCTCATTGAGATGAATGGCAAGCTGGTCAAAACCA<br>CCATTGAGGAACTCATCCCCCTCAAGTACACCAGGAACTAAAGTAATATCTGCGCTTATCCTTTAT<br>GGTTATTTTACCGGTAACATGATCTTGCGCAGATTGTAGAACAATTTTTACACTTTCAGGCCTCGTG<br>CGGATTCACCCACGAGGCTTTTTTTATTACACTGACTGAAACGTTTTTGCCCTATGAGCTCCGGTTA<br>CAGGCGTTTCAGTCATAAATCCTCTGAATGAAACGCGTTGTGAATC |
| pykA-DAS + 4:ampR SEQ ID NO 45<br>TGAACCTGACTGCTCTCTATCGTGGCGTTACGCCGGTGCACTTTGATAGCGCTAATGACGGCGTAG<br>CAGCTGCCAGCGAAGCGGTTAATCTGCTGCGCGATAAAGGTTACTTGATGTCTGGTGACCTGGTGA<br>TTGTCACCCAGGGCGACGTGATGAGTACCGTGGGTTCTACTAATACCACGCGTATTTTAACGGTAG<br>AGGCGGCCAACGATGAAAACTATTCTGAAAACTATGCGGATGCGTCTTAATAGTCCTGACGGATG<br>GCCTTTTTGCGTTTCTACAAACTCTTTTTGTTTATTTTTCTAAATACATTCAAATATGTATCCGCTCA<br>TGAGACAATAACCCTGATAAATGCTTCAATAATATTGAAAAAGGAAGAGTATGAGTATTCAACAT<br>TTCCGTGTCGCCCTTATTCCCTTTTTTGCGGCATTTTGCCTTCCTGTTTTTGCTCACCCAGAAACGCT<br>GGTGAAAGTAAAAGATGCTGAAGATCAGTTGGGTGCACGAGTGGGTTACATCGAACTGGATCTCA<br>ACAGCGGTAAGATCCTTGAGAGTTTTCGCCCCGAAGAACGTTTTCCAATGATGAGCACTTTTAAAG<br>TTCTGCTATGTGGCGCGGTATTATCCCGTGTTGACGCCGGGCAAGAGCAACTCGGTCGCCGCATAC<br>ACTATTCTCAGAATGACTTGGTTGAGTACTCACCAGTCACAGAAAAGCATCTTACGGATGGCATGA<br>CAGTAAGAGAATTATGCAGTGCTGCCATAACCATGAGTGATAACACTGCGGCCAACTTACTTCTG<br>ACAACGATCGGAGGACCGAAGGAGCTAACCGCTTTTTTGCACAACATGGGGGATCATGTAACTCG<br>CCTTGATCGTTGGGAACCGGAGCTGAATGAAGCCATACCAAACGACGAGCGTGACACCACGATGC<br>CTACAGCAATGGCAACAACGTTGCGCAAACTATTAACTGGCGAACTACTTACTCTAGCTTCCCGGC<br>AACAATTAATAGACTGGATGGAGGCGGATAAAGTTGCAGGACCACTTCTGCGCTCGGCCCTTCCG<br>GCTGGCTGGTTTATTGCTGATAAATCTGGAGCCGGTGAGCGTGGGTCTCGCGGTATCATTGCAGCA<br>CTGGGGCCAGATGGTAAGCCCTCCCGTATCGTAGTTATCTACACGACGGGGAGTCAGGCAACTAT<br>GGATGAACGAAATAGACAGATCGCTGAGATAGGTGCCTCACTGATTAAGCATTGGTAACTGTCAG<br>ACTAAGTACGTTGCCGGATGCGGCGAAAACGCCACATCCGGCCTACAGTTCAATGATAGTTCAAC<br>AGATTTCGAATATTCTGAAGCAAACTTGAACTTATCATCAGGCGAAGGCCTCTCCTCGCGAGAGGC<br>TTTTTATTTGATGGGATAAAGATCTTTGCGCTTATACGGCTGGATTTCGCCCGGTTTGCGAGTTTT<br>CAGCAAT |
| pykF-DAS + 4:purr SEQ ID NO 46<br>AAACGGCTCATCAGTTGGTACTGAGCAAAGGCGTTGTGCCGCAGCTTGTTAAAGAGATCACTTCTA<br>CTGATGATTTCTACCGTCTGGGTAAAGAACTGGCTCTGCAGAGCGGTCTGGCACACAAAGGTGAC<br>GTTGTAGTTATGGTTTCTGGTGCACTGGTACCGAGCGGCACTACTAACACCGCATCTGTTCACGTC<br>CTGGCGGCCAACGATGAAAACTATTCTGAAAACTATGCGGATGCGTCTTAATCCTGACGGATGGC<br>CTTTTTGCGTTTCTACAAACTCTTTTTGTTTATTTTTCTAAATACATTCAAATATGTATCCGCTCATG<br>AGACAATAACCCTGATAAATGCTTCAATAATATTGAAAAAGGAAGAGTATGACTGAATACAAGCC<br>CACGGTACGCTTGGCGACGCGCGACGATGTTCCCCGCGCTGTTCGTACATTAGCTGCGGCCTTTGC<br>AGATTACCCAGCGACGCGCCATACGGTCGATCCGGACCGCCATATCGAGCGTGTCACAGAATTGC<br>AGGAACTTTTCTTAACTCGCGTGGGCCTTGACATCGGAAAGGTCTGGGTGGCTGACGATGGCGCTG<br>CAGTGGCTGTTTGGACCACTCCGGAGAGTGTAGAGGCTGGTGCAGTGTTCGCCGAAATTGGTCCTC<br>GTATGGCCGAATTAAGTGGAAGTCGTCTGGCAGCCCAACAACAAATGGAAGGGTTGCTTGCGCCC<br>CACCGTCCGAAAGAACCCGCGTGGTTCCTTGCCACCGTTGGAGTAAGCCCAGATCACCAGGGGAA<br>GGGTTTAGGATCTGCCGTAGTTTTACCAGGTGTGGAGGCAGCAGAACGTGCGGGAGTTCCGGCCT<br>TCCTTGAGACGTCGGCGCCGCGCAATTTACCGTTTTACGAACGTCTTGGATTCACCGTTACGGCGG<br>ACGTGGAGGTGCCGGAGGGACCCCGTACTTGGTGTATGACTCGTAAACCGGGAGCCTGATAATAT<br>TGCTTTTGTGAATTAATTTGTATATCGAAGCGCCCTGATGGGCGCTTTTTTTATTTAATCGATAACC<br>AGAAGCAATAAAAAATCAAATCGGATTTCACTATATAATCTCACTTTATCTAAGATGAATCCGATG<br>GAAGCATCCTGTTTTCTCTCAATTTTTTTATCTAAAACCCAGCGTTCGATGCTTCTTTGAGCGAACG<br>ATCAAAAATAAGTGCCTTCCCATCAAAAAAATATTCTCAACATAAAAAACTTTGTGTAATACTTGT<br>AACGCTACATGGAGATTAACTCAATCTAGAGGGTATTAATAATGAAAGCTACTAAACTGG |

In the case of deletions for the following genes: mgsA, ptsA, epd, dhaL, and eda, lambda red recombineering along with a CRISPR-cas based gene deletion methodology was used as recently described by Moreb et al, 2017 (doi: 10.1021/acssynbio.7b00174). Briefly, gRNA expression plasmids were constructed to express gRNAs to target a given locus, donor DNA ordered to delete genes using recombineering, and primer s for locus confirmation by PCR and sequencing. These sequences are given in Table CM6, CM7 and CM8.

TABLE CM6

Primers to construct gRNA Cas9 cutting plasmids.

| Name | Sequence | SEQ ID NO |
|---|---|---|
| AM512_gRNAmgsA | CTGTATGCAACAGGCACTACGTTTTAGAGCTAGAAATAGCAAG | 47 |
| AM225_sgRNA_F3 | GTGCTCAGTATCTCTATCACTGA | 48 |
| AM514_gRNAptsA | ATGTGTTCTGATTTGCTGTGGTTTTAGAGCTAGAAATAGCAAG | 49 |
| AM225_sgRNA_F3 | GTGCTCAGTATCTCTATCACTGA | 50 |
| AM536_gRNAepd | TAAATGGCTTCGGTCGCATCGTTTTAGAGCTAGAAATAGCAAG | 51 |
| AM225_sgRNA_F3 | GTGCTCAGTATCTCTATCACTGA | 52 |
| AM537_gRNAdhaL | CTTTATCAGATGTTCCGCGAGTTTTAGAGCTAGAAATAGCAAG | 53 |
| AM225_sgRNA_F3 | GTGCTCAGTATCTCTATCACTGA | 54 |
| AM550_gRNAeda | GGTGCTGAATCCACAGCAGCGTTTTAGAGCTAGAAATAGCAA G | 55 |
| AM225_sgRNA_F3 | GTGCTCAGTATCTCTATCACTGA | 56 |

TABLE CM7

Donor DNA sequences to delete genes.

| Name | Sequence | SEQ ID NO: |
|---|---|---|
| AM519_ DONmgsA | GCAGCATAAGTGCTTACAGTAATCTGTAGGAAAGTTAACTACGGATCCCCG ATTATCAGCGTTATCTCGCGGACCGTCTGAAGTAA | 57 |
| AM549_ DONPtsA2 | CCTTTTACAGTTCCAGTTCATGTTGCAGCAGGCTGGCGATAGCGTTTTGCGG CATGCTTCCGGTTTATCGCAAGTTATGAGGCGGATCGC | 58 |
| AM538_ DONepd | ACGCATCATCTAACAATTTGATGACGGGAATTATGCAATTCGTGGAATTGTC GAACATTTAATCGACTGAAACGCTTCAGCTAGGATAAG | 59 |
| AM539_ DONdhaL | GATTGACTATCGAACGTAATTTAATTGGCGCGTACTGCACCTCACGACTGGG AGAAGGTGTCGGTGAATTAGCCCGTCAGATGTTAATGA | 60 |
| AM551_ DONeda | GCCTTCTACAGCTTCACGCGCCAGCTTAGTAATGCGGTCGTAATCGCCTGAT TACAAATTTGTCGTCTTAAAAAGTGATACAGGTTGCGC | 61 |

TABLE CM8

Primers to confirm gene deletions.

| Name | Sequence | SEQ ID NO |
|---|---|---|
| AM525_byemgsA_F | CTGACCCACAAACGCGAAAT | 62 |
| AM526_byemgsA_R | GGTGGCGAGAAAACCGTAAG | 63 |
| AM547_byeptsA_F2 | CGCCCGTCATTAAATGCTGA | 64 |
| AM548_byeptsA_R2 | GGCTAATAACCCTTGTGCGG | 65 |
| AM540_byeEpd_F | TTCGGCTGGACAAACATTCC | 66 |
| AM541_byeEpd_R | AACCTGTTGATCGTGCATGG | 67 |
| AM542_byeDhaL_F | CGTCTATAACCGCCTGACCA | 68 |
| AM543_byeDhaL_R | TTGTGGATCGTCAATTCCCG | 69 |
| AM552_byeEda_F | CTGGTAGACGAAGCGGAACT | 70 |
| AM553_byeEda_R | CCTCGATCGGGCATTTTGAC | 71 |

Subsection III. Plasmid Construction pCASCADE Plasmid Construction

Gene silencing guide arrays were expressed from a series of pCASCADE plasmids. The pCASCADE-control plasmid was prepared by swapping the pTet promoter in perRNA.Tet (Luo et al, 2015, NAR. doi: 10.1093/nar/gku971) with an insulated low phosphate induced ugpB gene promoter. Promoter sequences for all genes were obtained from EcoCyc database (https://ecocyc.org/). In order to design CASCADE guide array, CASCADE PAM sites near the −35 or −10 box of the promoter of interest were identified, 30 bp at the 3' end of PAM site was selected as the guide sequence and cloned into pCASCADE plasmid using Q5 site-directed mutagenesis (NEB, MA) following manufacturer's protocol, with the modification that 5% v/v DMSO was added to the Q5 PCR reaction. PCR cycles were as follows: amplification involved an initial denaturation step at 98° C. for 30 second followed by cycling at 98° C. for 10 second, 72° C. for 30 second, and 72° C. for 1.5 min (the extension rate was 30 second/kb) for 25 cycles, then a final extension for 2 min at 72° C. 2 μL of PCR mixture was used for 104 KLD reaction, which proceeded under room temperature for 1 hour, after which, 14 KLD mixture was used for electroporation.

The pCASCADE guide array plasmids were prepared by sequentially amplifying complementary halves of each smaller guide plasmid by PCR, followed by subsequent DNA assembly. The pCASCADE-control vector was used as template. pCASCADE plasmids with arrays of two or more guides were prepared using Q5 High-Fidelity 2× Master Mix (NEB, MA). PCR cycles were as follows: amplification involved an initial denaturation step at 98° C. for 30 second followed by cycling at 98° C. for 10 second, 66° C. for 30 second, and 72° C. for 45 second (the extension rate was 30 second/kb) for 35 cycles, then a final extension for 2 min at 72° C. PCR product was purified by gel-extraction, 20 µL ultrapure water was used to elute 50 µL PCR reaction purification. 14 of each eluted PCR product was used for 104 of Gibson Assembly (NEB, MA), which was completed by incubation at 50° C. for 15 min. 14 Gibson Assembly mix was used for electroporation. Sequence information for silencing guides is given in Table CM9 and CM10.

TABLE CM9

List of pCASCADE plasmids used in this study. Sequences available in Addgene where submitted.

| Silencing Plasmid | Promoter(s) Silenced | Addgene # |
|---|---|---|
| pCASCADE-control | none | 65821 |
| pCASCADE-gltAl | gltAp1 | 71334 |
| pCASCADE-gltA2 | gltAp2 | 65817 |
| pCASCADE-zwf | zwf | 65825 |
| pCASCADE-gltA1-gltA2 | gltAp1, gltAp2 | 71348 |
| pCASCADE-gltA1-zwf | gltAp1, zwf | 71337 |
| pCASCADE-gltA2-zwf | gltAp2, zwf | 71338 |
| pCASCADE-pykA-pykF | pykA, pykF | NA |
| pCASCADE-gltA1-pykA-pykF | gltAp1, pykA, pykF | NA |
| pCASCADE-gltA2-pykA-pykF | gltAp2, pykA, pykF | NA |
| pCASCADE-gltA1-gltA2-pykA-pykF | gltAp1, gltAp2, pykA, pykF | NA |
| pCASCADE-gltA1-gltA2-zwf-pykA-pykF | gltAp1, gltAp2, zwf, pykA, pykF | NA |
| pCASCADE-gltA1-zwf-pykA-pykF | gltAp1, zwf, pykA, pykF | NA |
| pCASCADE-gltA2-zwf-pykA-pykF | gltAp2, zwf, pykA, pykF | NA |

TABLE CM10

List of sgRNA guide array sequences and primers used to construct them from given templates. Sequences for guide arrays containing guides with pykA or pykF gRNAs are given. Spacers are italicized.

| sgRNA/Primer Name | Sequence | SEQ ID NO | Template |
|---|---|---|---|
| PYkA | *TCGAGTTCCCCGCGCCAGCGGGGATAAACCG*TGACGATCGCTAAAAACGACTGTCACTGTC*TCGAGTTCCCCGCGCCAGCGGGGATAAACCG* | 72 | |
| pykA-sgRNA-FOR | ACGACTGTCACTGTCTCGAGTTCCCCGCGCCAGCGGGGATAAACCGAAAAAAAAACCCC | 73 | pCASCADE control |
| pykA-sgRNA-REV | TTTTAGCGATCGTCACGGTTTATCCCCGCTGGCGCGGGGAACTCGAGGTGGTACCAGATC | 74 | |
| pykF | *TCGAGTTCCCCGCGCCAGCGGGGATAAACCG*CACCACCACTTTCGTAATACCGGATTCGCT*TCGAGTTCCCCGCGCCAGCGGGGATAAACCG* | 75 | |
| pykF-sgRNA-FOR | AATACCGGATTCGCTTCGAGTTCCCCGCGCCAGCGGGGATAAACCGAAAAAAAAACCCC | 76 | pCASCADE control |
| pykF-sgRNA-REV | ACGAAAGTGGTGGTGCGGTTTATCCCCGCTGGCGCGGGGAACTCGAGGTGGTACCAGATC | 77 | |
| PYkA-pykF | *TCGAGTTCCCCGCGCCAGCGGGGATAAACCG*TGACGATCGCTAAAAACGACTGTCACTGTC*TCGAGTTCCCCGCGCCAGCGGGGATAAACCG*CACCACCACTTTCGTAATACCGGATTCGCT*TCGAGTTCCCCGCGCCAGCGGGGATAAACCG* | 78 | |
| pykF-FOR | AATACCGGATTCGCTTCGAGTTCCCCGCGCCAGCGGGGATAAACCGAAAAAAAAACCCC | 79 | pCASCADE-pykF |
| pCASCADE-REV | CTTGCCCGCCTGATGAATGCTCATCCGG | 80 | |

TABLE CM10-continued

List of sgRNA guide array sequences and primers used to construct them from given templates. Sequences for guide arrays containing guides with pykA or pykF gRNAs are given. Spacers are italicized.

| sgRNA/Primer Name | Sequence | SEQ ID NO | Template |
| --- | --- | --- | --- |
| pCASCADE-FOR | CCGGATGAGCATTCATCAGGCGGGCAAG | 81 | pCASCADE-pykA |
| pykA-REV | ACGAAAGTGGTGGTGCGGTTTATCCCCG CTGGCGCGGGGAACTCGAGGTGGTACCA GATC | 82 | |
| gltA1-pykA-pykF | *TCGAGTTCCCCGCGCCAGCGGGGATAAAC CG*AAAAGCATATAATGCGTAAAAGTTAT GAAGT*TCGAGTTCCCCGCGCCAGCGGGGA TAAACCG*TGACGATCGCTAAAAACGACTG TCACTGTC*TCGAGTTCCCCGCGCCAGCGG GGATAAACCG*CACCACCACTTTCGTAATA CCGGATTCGCT*TCGAGTTCCCCGCGCCAG CGGGGATAAACCG* | 83 | |
| pykA-FOR | GCGCCAGCGGGGATAAACCGTGACGATC GCTAAAAAC | 84 | pCASCADE-pykA-PYkF |
| pCASCADE-REV | CTTGCCCGCCTGATGAATGCTCATCCGG | 80 | |
| pCASCADE-FOR | CCGGATGAGCATTCATCAGGCGGGCAAG | 81 | pCASCADE-gltA1 |
| gltA1-REV | CGGTTTATCCCCGCTGGCGCGGGGAACT CGAACTTCATAACTTTTAC | 85 | |
| gltA2-pykA-pykF | *TCGAGTTCCCCGCGCCAGCGGGGATAAAC CG*TATTGACCAATTCATTCGGGACAGTTA TTAGT*TCGAGTTCCCCGCGCCAGCGGGGA TAAACCG*TGACGATCGCTAAAAACGACTG TCACTGTC*TCGAGTTCCCCGCGCCAGCGG GGATAAACCG*CACCACCACTTTCGTAATA CCGGATTCGCT*TCGAGTTCCCCGCGCCAG CGGGGATAAACCG* | 86 | |
| pykA-FOR | GCGCCAGCGGGGATAAACCGTGACGATC GCTAAAAAC | 87 | pCASCADE-pykA-PYkF |
| pCASCADE-REV | CTTGCCCGCCTGATGAATGCTCATCCGG | 80 | |
| pCASCADE-FOR | CCGGATGAGCATTCATCAGGCGGGCAAG | 81 | pCASCADE-gltA2 |
| gltA2-REV | CGGTTTATCCCCGCTGGCGCGGGGAACT CGAACTAATAACTGTC | 88 | |
| zwf-pykA-pykF | *TCGAGTTCCCCGCGCCAGCGGGGATAAAC CG*CTCGTAAAAGCAGTACAGTGCACCGT AAGA*TCGAGTTCCCCGCGCCAGCGGGGAT AAACCG*TGACGATCGCTAAAAACGACTG TCACTGTC*TCGAGTTCCCCGCGCCAGCGG GGATAAACCG*CACCACCACTTTCGTAATA CCGGATTCGCT*TCGAGTTCCCCGCGCCAG CGGGGATAAACCG* | 89 | |
| pykA-FOR | GCGCCAGCGGGGATAAACCGTGACGATC GCTAAAAAC | 90 | pCASCADE-pykA-PYkF |
| pCASCADE-REV | CTTGCCCGCCTGATGAATGCTCATCCGG | 80 | |
| pCASCADE-FOR | CCGGATGAGCATTCATCAGGCGGGCAAG | 81 | pCASCADE-zwf |
| zwf-REV | CGGTTTATCCCCGCTGGCGCGGGGAACT CGATCTTACGGTGCACTGTAC | 91 | |
| gltA1-gltA2-pykA-pykF | *TCGAGTTCCCCGCGCCAGCGGGGATAAAC CG*AAAAGCATATAATGCGTAAAAGTTAT GAAGT*TCGAGTTCCCCGCGCCAGCGGGGA TAAACCG*TATTGACCAATTCATTCGGGAC AGTTATTAGT*TCGAGTTCCCCGCGCCAGC GGGGATAAACCG*TGACGATCGCTAAAAA CGACTGTCACTGTC*TCGAGTTCCCCGCGC CAGCGGGGATAAACCG*CACCACCACTTTC GTAATACCGGATTCGCT*TCGAGTTCCCCG CGCCAGCGGGGATAAACCG* | 92 | |

TABLE CM10-continued

List of sgRNA guide array sequences and primers used to construct them from given templates. Sequences for guide arrays containing guides with pykA or pykF gRNAs are given. Spacers are italicized.

| sgRNA/Primer Name | Sequence | SEQ ID NO | Template |
|---|---|---|---|
| pykA-FOR | GCGCCAGCGGGGATAAACCGTGACGATC GCTAAAAAC | 93 | pCASCADE-pykA-PYkF |
| pCASCADE-REV | CTTGCCCGCCTGATGAATGCTCATCCGG | 80 | |
| pCASCADE-FOR | CCGGATGAGCATTCATCAGGCGGGCAAG | 81 | pCASCADE-gltA1-gltA2 |
| gltA2-REV | CGGTTTATCCCCGCTGGCGCGGGGAACT CGAACTAATAACTGTC | 94 | |
| gltA1-zwf-pykA-pykF | *TCGAGTTCCCCGCGCCAGCGGGGATAAAC CG*AAAAGCATATAATGCGTAAAAGTTAT GAAGT*TCGAGTTCCCCGCGCCAGCGGGGA TAAACCG*CTCGTAAAAGCAGTACAGTGCA CCGTAAGA*TCGAGTTCCCCGCGCCAGCGG GGATAAACCG*TGACGATCGCTAAAAACG ACTGTCACTGTC*TCGAGTTCCCCGCGCCA GCGGGGATAAACCG*CACCACCACTTTCGT AATACCGGATTCGCT*TCGAGTTCCCCGCG CCAGCGGGGATAAACCG* | 95 | |
| pykA-FOR | GCGCCAGCGGGGATAAACCGTGACGATC GCTAAAAAC | 96 | pCASCADE-pykA-PYkF |
| pCASCADE-REV | CTTGCCCGCCTGATGAATGCTCATCCGG | 80 | |
| pCASCADE-FOR | CCGGATGAGCATTCATCAGGCGGGCAAG | 81 | pCASCADE-gltA1-zwf |
| zwf-REV | CGGTTTATCCCCGCTGGCGCGGGGAACT CGATCTTACGGTGCACTGTAC | 97 | |
| gltA2-zwf-pykA-pykF | *TCGAGTTCCCCGCGCCAGCGGGGATAAAC CG*TATTGACCAATTCATTCGGGACAGTTA TTAGT*TCGAGTTCCCCGCGCCAGCGGGGA TAAACCG*CTCGTAAAAGCAGTACAGTGCA CCGTAAGA*TCGAGTTCCCCGCGCCAGCGG GGATAAACCG*TGACGATCGCTAAAAACG ACTGTCACTGTC*TCGAGTTCCCCGCGCCA GCGGGGATAAACCG*CACCACCACTTTCGT AATACCGGATTCGCT*TCGAGTTCCCCGCG CCAGCGGGGATAAACCG* | 98 | |
| pykA-FOR | GCGCCAGCGGGGATAAACCGTGACGATC GCTAAAAAC | 99 | pCASCADE-pykA-PYkF |
| pCASCADE-REV | CTTGCCCGCCTGATGAATGCTCATCCGG | 80 | |
| pCASCADE-FOR | CCGGATGAGCATTCATCAGGCGGGCAAG | 81 | pCASCADE-gltA2-zwf |
| zwf-REV | CGGTTTATCCCCGCTGGCGCGGGGAACT CGATCTTACGGTGCACTGTAC | 100 | |
| gltA1-gltA2-zwf-pykA-pykF | *TCGAGTTCCCCGCGCCAGCGGGGATAAAC CG*AAAAGCATATAATGCGTAAAAGTTAT GAAGT*TCGAGTTCCCCGCGCCAGCGGGGA TAAACCG*TATTGACCAATTCATTCGGGAC AGTTATTAGT*TCGAGTTCCCCGCGCCAGC GGGGATAAACCG*CTCGTAAAAGCAGTAC AGTGCACCGTAAGA*TCGAGTTCCCCGCGC CAGCGGGGATAAACCG*TGACGATCGCTAA AAACGACTGTCACTGTC*TCGAGTTCCCCG CGCCAGCGGGGATAAACCG*CACCACCACT TTCGTAATACCGGATTCGCT*TCGAGTTCC CCGCGCCAGCGGGGATAAACCG* | 101 | |
| pykA-FOR | GCGCCAGCGGGGATAAACCGTGACGATC GCTAAAAAC | 102 | pCASCADE-pykA-PYkF |
| pCASCADE-REV | CTTGCCCGCCTGATGAATGCTCATCCGG | 80 | |
| pCASCADE-FOR | CCGGATGAGCATTCATCAGGCGGGCAAG | 81 | pCASCADE-gltA1-gltA2-zwf |
| zwf-REV | CGGTTTATCCCCGCTGGCGCGGGGAA CTCGATCTTACGGTGCACTGTAC | 103 | |

pCDF-Nox Plasmid Construction

NADH oxidase from *Streptococcus mutans* (UniProt Q54453) was codon optimized using the Codon Optimization Tool from the IDT website, phosphorylated G-Blocks™ were designed and purchased from IDT. pCDF-nox was assembled using NEBuilder® HiFi DNA Assembly Master Mix following manufacturer's protocol (NEB, MA) with the G-Blocks™ and a PCR product of pCDF-1b containing only the origin and spectinomycin resistance marker. Plasmid sequence was confirmed by DNA sequencing (Eton Bioscience, NC).

Subsection IV. Microfermentations

Plasmids were transformed into host strains by electroporation using ECM 630 High Throughput Electroporation System (Harvard Apparatus, Inc. Holliston, Mass.) following manufacturer's protocol or using individual electroporation cuvettes. Glycerol stocks were prepared for each transformation plate by adding equal volume of sterile 20% glycerol, and 3 μL were used to inoculate overnight culture in 150 μL SM10++ medium with appropriate antibiotics. Plates were covered with sandwich covers (Model #CR1596 obtained from EnzyScreen, Haarlam, The Netherlands). These covers ensured minimal evaporative loss during incubation. Unless otherwise stated, 96 well plates were cultured at 37° C., 400 rpm for 16 hours, shaker orbit is 25 mm. This combination of orbit and minimal shaking speed is required to obtain needed mass transfer coefficient and provide adequate culture oxygenation.

After 16 hours of growth, cells were pelleted by centrifugation, excess media was removed and cells were resuspended in 150 μL of FGM3 Wash solution. Subsequently cells were once again pelleted and again excess media was removed, pellet was resuspended in 50 μL FGM3 No Phosphate media containing appropriate antibiotics. 5 μL of the resuspended culture was added to 195 μL of water for OD600 measurement using standard flat bottom 96 well plate. OD600 for production was normalized to OD600=1, using FGM3 No Phosphate media containing appropriate antibiotics, in a total volume of 150 μL using standard 96 well plate. Plates were covered with sandwich covers (Model #CR1596 obtained from EnzyScreen, Haarlam, The Netherlands) and 96 well plate cultures were incubated at 37° C., 400 rpm for 24 hours. After 24 hours of production, all samples from each well were pelleted by centrifugation and the supernatant collected for subsequent analytical measurement. Triplicate microfermentations were performed for each strain.

Subsection V. Lab Scale Fermentations

1 L Fermentation Seeds: Single colony from transformation plate was inoculated into 5 mL LB with appropriate antibiotics and cultured at 37° C., 220 rpm for 16 hours. 500 μL of the LB culture was inoculated into 50 mL FLNM10 media supplemented with 200 mM MOPS buffer pH=7.4, with appropriate antibiotics in square shake flask (CAT #: 25-214, Genesee Scientific, Inc. San Diego, Calif.), the culture was incubated at 37° C. with a shaking speed of 220 rpm for 24 hours, at which time OD600 is usually between 3 and 10, the culture was harvested by centrifugation at 4000 rpm for 15 min, supernatant was discarded and cell culture was normalized to OD600=10 using SM10 media. For 1 L fermentation seed, 6 mL of normalized OD600=10 culture was added to 1.5 mL of 50% glycerol in cryovials, and stored at −80° C.

1 L Fermentations: An Infors-HT Multifors (Laurel, Md., USA) parallel bioreactor system was used to perform 1 L fermentations, including three gas connection mass flow controllers configured for air, oxygen and nitrogen gases. Vessels used had a total volume of 1400 mL and a working volume of up to 1 L. Online pH and pO2 monitoring and control were accomplished with Hamilton probes. Offgas analysis was accomplished with a multiplexed Blue-in-One BlueSens gas analyzer (BlueSens. Northbrook, Ill., USA). Culture densities were continually monitored using Optek 225 mm OD probes, (Optek, Germantown, Wis., USA). The system used was running IrisV6.0 command and control software and integrated with a Seg-flow automated sampling system (Flownamics, Rodeo, Calif., USA), including FISP cell free sampling probes, a Segmod 4800 and FlowFraction 96 well plate fraction collector.

For the standardized 2-stage process with ~10 gcdw/L biomass, tanks were filled with 800 mL of FLNM10 medium (Table CM3). Antibiotics were added as appropriate. Frozen seed vials were thawed on ice and 7.5 mL of seed culture was used to inoculate the tanks. After inoculation, tanks were controlled at 37° C. and pH 6.8 using 5 M ammonium hydroxide and 1 M hydrochloric acid as titrants. 10 M ammonium hydroxide was used as the base fermentation run. The following oxygen control scheme was used to maintain the desired dissolved oxygen set point. First gas flow rate was increased from a minimum of 0.3 L/min of air to 0.8 L/min of air, subsequently, if more aeration was needed, agitation was increased from a minimum of 300 rpm to a maximum of 1000 rpm. Finally, if more oxygen was required to achieve the set point, oxygen supplementation was included using the integrated mass flow controllers. Starting glucose concentration was 25 g/L. A constant concentrated sterile filtered glucose feed (500 g/L) was added to the tanks at specified rate, i.e. 2 g/h, once agitation reached 800 rpm. In cases where feed rate or dissolved oxygen content needed to be varied for robustness study, changes were made after cells entered stationary phase. Fermentation runs were extended for up to ~50 hours after entry into stationary phase and samples automatically withdrawn every 3 hours. Samples were saved for subsequent analytical measurement.

Subsection VI: Determination of Strain Dry Weight

Culture samples (5 ml, n=3) were taken and washed 2× with deionized water via centrifugation and resuspension. After wash steps the OD of the samples were determined at 600 nm. Subsequently, samples were filtered over pre-weighed nitrocellulose filters (pore size, 0.45 μm). Filters were washed extensively with demineralized water and dried in a microwave oven for 2 min and weighed to determine correlation of OD600 and gDCW, which was 0.5.

Subsection VII: Analytical Methods

Figure 3:
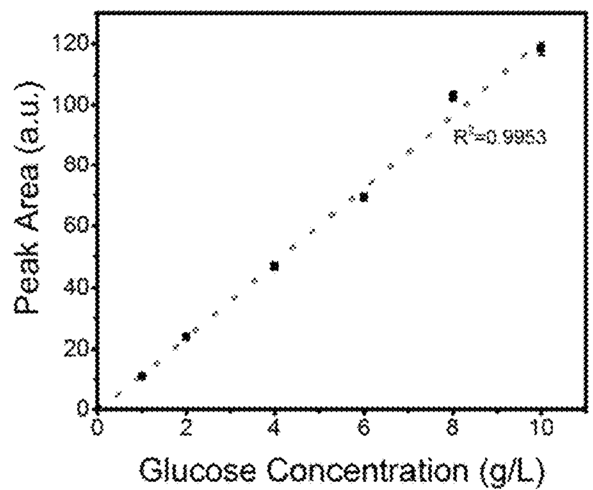
FIG. 3 depicts an example standard curve for the quantification of glucose.

Glucose Quantification: A UPLC-RI method was developed for the quantification of glucose concentrations, using an Acquity H-Class UPLC integrated with a Waters 2414 Refractive Index (RI) detector (Waters Corp., Milford, Mass. USA). Chromatographic separation was performed using a Bio-Rad Fast Acid Analysis HPLC Column (100×7.8 mm, 9 μm particle size; CAT #: #1250100, Bio-Rad Laboratories, Inc., Hercules, Calif.) at 65° C. 5 mM sulfuric acid was used as the eluent. The isocratic elution was as follows: 0-0.1 min, flow rate increased from 0.4 mL/min to 0.42 mL/min, 0.1-12 min flow rate at 0.48 mL/min. Sample injection volume was 10 μL. UPLC method development was carried out using standard aqueous stock solutions of analytes. Peak integration and further analysis was performed using MassLynx v4.1 software. The linear range used for glucose was 1-10 g/L. Samples were diluted as needed to be within the accurate linear range. Dilution was performed using ultrapure water. A sample standard curve is shown in FIG. 3.

Figure 4:
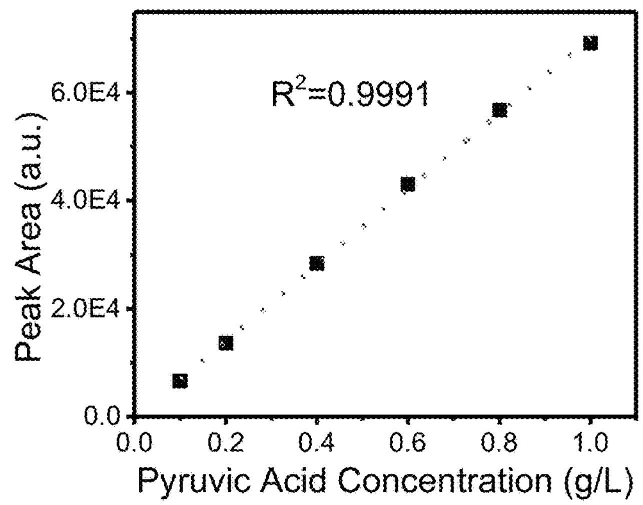
FIG. 4 depicts an example standard curve for the quantification of pyruvate.

Pyruvate Quantification: A reverse phase UPLC-TUV method was developed for the quantification of pyruvic acid. Chromatographic separation was performed using a Restek Ultra AQ C18 column (150 mm×2.1 i.d., 3 μm; CAT #: 9178362, Restek Corporation, Bellefonte, Pa.) at 30° C. 20 mM phosphoric acid was used as the eluent. The isocratic elution was as follows: 0-3 min isocratic at 0.8 mL/min. Sample injection volume was 10 μL. Absorbance was monitored at 210 nm. UPLC method development was carried out using standard aqueous stock solution of analyte. Separations were performed using an Acquity H-Class UPLC (Waters Corp., Milford, Mass. USA). Peak integration and further analysis was performed using MassLynx v4.1 software. The linear range for pyruvic acid was 0.1-1 g/L. Samples were diluted as needed to be within the accurate linear range. Dilution was performed using ultrapure water. A sample standard curve is shown in FIG. 4.

The invention claimed is:

1. A genetically modified *E. coli* microorganism for production of pyruvate, the microorganism comprising, i. an inducible gene expression-silencing synthetic metabolic valve silencing gene expression of pyruvate kinase A (pykA) or pyruvate kinase F (pykF) gene(s); an enzymatic degradation synthetic metabolic valve inducing enzymatic degradation of pyruvate kinase A (pykA) or pyruvate kinase F (pykF) enzyme(s) or a combination thereof, and one or more of:

ii. an inducible gene expression-silencing synthetic metabolic valve comprising silencing gene expression of citrate synthase (gltA), pyruvate dehydrogenase (lpd), or glucose-6-phosphate dehydrogenase (zwf) gene(s); and iii. an inducible enzymatic degradation synthetic metabolic valve comprising inducing enzymatic degradation of citrate synthase (gltA), pyruvate dehydrogenase (lpd), or glucose-6-phosphate dehydrogenase (zwf) enzyme(s); and wherein the microorganism produces a titer of pyruvate or pyruvic acid of greater than 0.08 g/gDCW-hr in a stationary, non-growth, phase of a biofermentation process.

2. The genetically modified microorganism of claim 1, wherein the gene expression-silencing synthetic metabolic valve and the enzymatic degradation synthetic metabolic valve are induced under conditions of a transition phrase of a multi-stage biofermentation process.

3. The genetically modified microorganism of claim 1, wherein the one or more enzymes of the gene expression-silencing synthetic metabolic valve and of the enzymatic degradation synthetic metabolic valve are one of: fabI, zwf, gltA, ppc, udhA, lpd, sucD, aceA, pfkA, ion, rpoS, pykA, pykF, tktA or tktB.

4. The genetically modified microorganism of claim 1, wherein the genetically modified microorganism further comprises overexpression of a NADH oxidase.

5. The genetically modified microorganism of claim 1, wherein the silencing of gene expression comprises CRISPR interference and the genetically modified microorganism also expresses a CASCADE guide array, the array comprising two or more genes encoding small guide RNAs each specific for targeting a different gene for simultaneous silencing of multiple genes.

6. A multi-stage fermentation bioprocess for producing a pyruvate product from a genetically modified microorganism, comprising:

(a) growing a genetically modified microorganism, the genetically modified *E. coli* microorganism comprising, i. a gene expression-silencing synthetic metabolic valve silencing gene expression of pyruvate kinase A (pykA) or pyruvate kinase F (pykF) gene(s); an enzymatic degradation synthetic metabolic valve inducing enzymatic degradation of pyruvate kinase A (pykA) or pyruvate kinase F (pykF) enzyme(s) or a combination thereof, and one or more of:

ii. a gene expression-silencing synthetic metabolic valve comprising silencing gene expression of citrate synthase (gltA), pyruvate dehydrogenase (lpd), or glucose-6-phosphate dehydrogenase (zwf) gene(s);

iii. an enzymatic degradation synthetic metabolic valve comprising inducing enzymatic degradation of citrate synthase (gltA), pyruvate dehydrogenase (lpd), or glucose-6-phosphate dehydrogenase (zwf) enzyme(s); and (b)

(i) inducing the synthetic metabolic valve(s) to slow or stop the growth of the microorganism and to change metabolism within the microorganism; and (ii) producing a pyruvate titer of greater than 0.08 g/gDCW-hr.

7. The multi-stage fermentation bioprocess of claim 6, further comprising:

a centrifugation to separate the genetically modified microorganism and the pyruvate or pyruvic acid.

8. The multi-stage fermentation bioprocess of claim 6, further comprising formation of a pyruvate salt from the pyruvate or pyruvic acid.

9. The multi-stage fermentation bioprocess of claim 6, further comprising formation of a pyruvate ester from the pyruvate or pyruvic acid.

10. The multi-stage fermentation bioprocess of claim 6 wherein the genetically modified microorganism further comprises overexpression of a NADH oxidase.

* * * * *

UNITED STATES PATENT AND TRADEMARK OFFICE

CERTIFICATE OF CORRECTION

PATENT NO. : 11,203,744 B2
APPLICATION NO. : 16/448292
DATED : December 21, 2021
INVENTOR(S) : Lynch et al.

It is certified that error appears in the above-identified patent and that said Letters Patent is hereby corrected as shown below:

In the Specification

Column 1 Line 16-23 please replace paragraph entitled "FEDERALLY SPONSORED RESEARCH OR DEVELOPMENT" as shown below:
FEDERALLY SPONSORED RESEARCH OR DEVELOPMENT
This invention was made with government support under Federal Grant No. MCB-1445726 awarded by the National Science Foundation and Federal Contract No. HR0011-14-C-0075 awarded by the United States Department of Defense and Federal Grant No. ONR YIP 12043956 awarded by the United States Department of Defense, N00014-16-1-2558 awarded by NAVY/ONR and DE-EE0007563 awarded by DOE. The government has certain rights in the invention.

Signed and Sealed this
Tenth Day of May, 2022

Katherine Kelly Vidal

Katherine Kelly Vidal
*Director of the United States Patent and Trademark Office*